United States Patent
Glimcher et al.

(10) Patent No.: US 9,956,236 B2
(45) Date of Patent: May 1, 2018

(54) METHODS FOR INCREASING IMMUNE RESPONSES USING AGENTS THAT DIRECTLY BIND TO AND ACTIVATE IRE-1

(75) Inventors: Laurie H. Glimcher, New York, NY (US); Sarah Bettigole, New York, NY (US); Fabio Martinon, Lausanne (CH)

(73) Assignee: Cornell University, Ithaca, NY (US)

( * ) Notice: Subject to any disclaimer, the term of this patent is extended or adjusted under 35 U.S.C. 154(b) by 0 days. days.

(21) Appl. No.: 13/983,180

(22) PCT Filed: Feb. 7, 2012

(86) PCT No.: PCT/US2012/024140
§ 371 (c)(1),
(2), (4) Date: Oct. 15, 2013

(87) PCT Pub. No.: WO2012/109238
PCT Pub. Date: Aug. 16, 2012

(65) Prior Publication Data
US 2014/0030294 A1    Jan. 30, 2014

Related U.S. Application Data

(60) Provisional application No. 61/440,224, filed on Feb. 7, 2011.

(51) Int. Cl.
*A61K 31/675* (2006.01)
*A61K 31/427* (2006.01)
*A61K 31/44* (2006.01)
*A61K 31/472* (2006.01)
*A61K 45/06* (2006.01)
*A61K 31/513* (2006.01)

(52) U.S. Cl.
CPC .......... *A61K 31/675* (2013.01); *A61K 31/427* (2013.01); *A61K 31/44* (2013.01); *A61K 31/472* (2013.01); *A61K 31/513* (2013.01); *A61K 45/06* (2013.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 4,683,194 A | 7/1987 | Saiki et al. |
| 4,683,195 A | 7/1987 | Mullis et al. |
| 4,683,202 A | 7/1987 | Mullis |
| 4,812,128 A | 3/1989 | Mikelsaar |

(Continued)

FOREIGN PATENT DOCUMENTS

| | | |
|---|---|---|
| EP | 0857780 A1 | 8/1998 |
| EP | 1669067 A2 | 6/2000 |

(Continued)

OTHER PUBLICATIONS

Hetz and Glimcher, Fine-Tuning of the Unfolded Protein Response: Assembling the IRE1 α Interactome. Mol. Cell, 2009; 35: 551-561.*

(Continued)

*Primary Examiner* — Janet L Andres
*Assistant Examiner* — Stuart W Snyder
(74) *Attorney, Agent, or Firm* — Schwegman Lundberg & Woessner, P.A.

(57) ABSTRACT

The invention provides, e.g., compositions and methods for increasing activation of immune cells.

10 Claims, 5 Drawing Sheets

(56) References Cited

U.S. PATENT DOCUMENTS

Figure 1D:
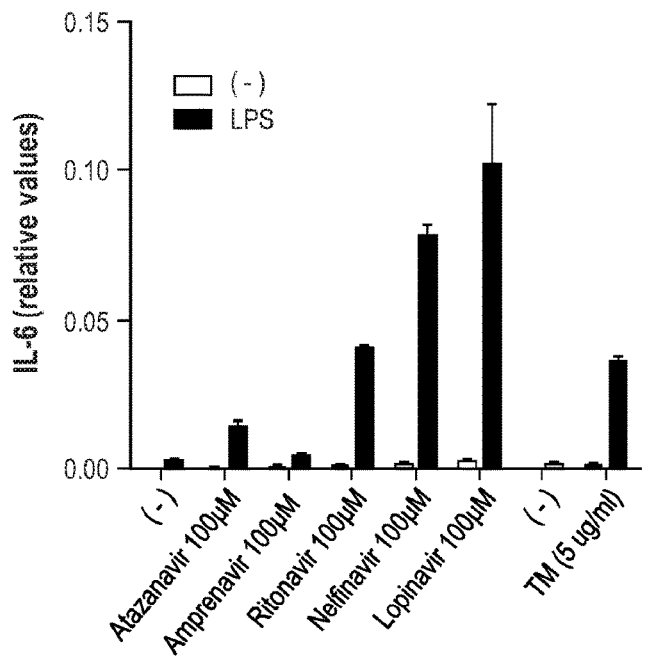

| | | |
|---|---|---|
| 4,868,116 A | 9/1989 | Morgan et al. |
| 4,873,316 A | 10/1989 | Meade et al. |
| 4,879,214 A | 11/1989 | Kornher et al. |
| 4,879,215 A | 11/1989 | Weng et al. |
| 4,906,122 A | 3/1990 | Barrett et al. |
| 4,980,286 A | 12/1990 | Morgan et al. |
| 4,987,071 A | 1/1991 | Cech et al. |
| 5,030,103 A | 7/1991 | Buist et al. |
| 5,116,742 A | 5/1992 | Cech et al. |
| 5,166,320 A | 11/1992 | Wu et al. |
| 5,223,409 A | 6/1993 | Ladner et al. |
| 5,233,409 A | 8/1993 | Schwab |
| 5,283,317 A | 2/1994 | Sailer et al. |
| 5,399,346 A | 3/1995 | Anderson et al. |
| 5,491,084 A | 2/1996 | Chalfie et al. |
| 5,498,531 A | 3/1996 | Jarrell |
| 5,583,973 A | 12/1996 | DeLisi et al. |
| 5,589,369 A | 12/1996 | Seidman et al. |
| 5,591,669 A | 1/1997 | Krimpenfort et al. |
| 5,612,894 A | 3/1997 | Wertz |
| 5,650,298 A | 7/1997 | Bujard et al. |
| 5,658,570 A | 8/1997 | Newman et al. |
| 5,693,780 A | 12/1997 | Newman et al. |
| 5,730,975 A | 3/1998 | Hotamisligil et al. |
| 5,756,096 A | 5/1998 | Newman et al. |
| 5,811,524 A | 9/1998 | Brams et al. |
| 5,908,762 A | 6/1999 | Ono et al. |
| 5,939,598 A | 8/1999 | Kucherlapati et al. |
| 5,945,307 A | 8/1999 | Glucksmann et al. |
| 6,037,148 A | 3/2000 | Khodadoust |
| 6,075,181 A | 6/2000 | Kucherlapati et al. |
| 6,080,576 A | 6/2000 | Zambrowicz et al. |
| 6,093,573 A | 7/2000 | Beamer et al. |
| 6,329,422 B1 | 12/2001 | Fischer et al. |
| 6,400,487 B1 | 6/2002 | Harris et al. |
| 6,410,516 B1 | 6/2002 | Baltimore et al. |
| 6,413,735 B1 | 7/2002 | Lau |
| 6,630,312 B2 | 10/2003 | Shoelson |
| 6,632,608 B2 | 10/2003 | Glimcher et al. |
| 6,632,641 B1 | 10/2003 | Brennan et al. |
| 7,220,539 B1 | 5/2007 | Du et al. |
| 7,306,905 B2 | 12/2007 | Ron et al. |
| 7,358,415 B2 | 4/2008 | Glimcher et al. |
| 8,227,184 B2 | 7/2012 | Glimcher et al. |
| 8,434,740 B2 | 5/2013 | Logtenberg |
| 8,765,932 B2 | 7/2014 | Fitzgerald et al. |
| 8,940,479 B2 | 1/2015 | Lee et al. |
| 2002/0059652 A1 | 5/2002 | Glimcher et al. |
| 2003/0096762 A1 | 5/2003 | Fischer et al. |
| 2003/0224428 A1 | 12/2003 | Ron et al. |
| 2004/0077020 A1 | 4/2004 | Mannick et al. |
| 2004/0110236 A1 | 6/2004 | Glimcher et al. |
| 2004/0170622 A1* | 9/2004 | Glimcher et al. ......... 424/130.1 |
| 2004/0197272 A1 | 10/2004 | Fischer et al. |
| 2005/0059052 A1 | 3/2005 | Kaufman et al. |
| 2005/0059652 A1 | 3/2005 | Hamann et al. |
| 2005/0250182 A1 | 11/2005 | Kaufman et al. |
| 2006/0057104 A1 | 3/2006 | Cheng et al. |
| 2006/0063187 A1 | 3/2006 | Hotamisligil |
| 2006/0073213 A1 | 4/2006 | Hotamisligil et al. |
| 2006/0148739 A1 | 7/2006 | Kotani et al. |
| 2007/0141074 A1 | 6/2007 | Schubert |
| 2007/0196335 A1 | 8/2007 | Pardoll et al. |
| 2008/0241114 A1 | 10/2008 | Glimcher et al. |
| 2009/0186893 A1 | 7/2009 | Patterson et al. |
| 2009/0232738 A1 | 9/2009 | Glimcher et al. |
| 2009/0275638 A1 | 11/2009 | Fitzgerald et al. |
| 2009/0291857 A1 | 11/2009 | Koong et al. |
| 2010/0075894 A1 | 3/2010 | Hotamisligil et al. |
| 2010/0266618 A1 | 10/2010 | Stojdl et al. |
| 2011/0052669 A1 | 3/2011 | Lee et al. |
| 2011/0142799 A1 | 6/2011 | Glimcher et al. |
| 2012/0141539 A1 | 6/2012 | Glimcher |
| 2012/0270877 A1 | 10/2012 | Zeng et al. |
| 2012/0322814 A1 | 12/2012 | Korennykh et al. |
| 2014/0030294 A1 | 1/2014 | Glimcher |
| 2014/0088148 A1 | 3/2014 | Dakshanamurthy et al. |
| 2014/0170622 A1 | 6/2014 | Pastrick et al. |
| 2015/0018406 A1 | 1/2015 | Glimcher |
| 2016/0237429 A1 | 8/2016 | Cubillos-Ruiz et al. |

FOREIGN PATENT DOCUMENTS

| | | |
|---|---|---|
| WO | 99/002468 A1 | 3/1989 |
| WO | 89/005345 A1 | 6/1989 |
| WO | 89/007136 A2 | 8/1989 |
| WO | 90/11345 A1 | 10/1990 |
| WO | 91/01140 A1 | 2/1991 |
| WO | 91/17271 A1 | 11/1991 |
| WO | 92/01047 A1 | 1/1992 |
| WO | 92/007573 A1 | 5/1992 |
| WO | 92/09680 A1 | 6/1992 |
| WO | 92/09690 A2 | 6/1992 |
| WO | 92/15679 A1 | 9/1992 |
| WO | 92/18619 A1 | 10/1992 |
| WO | 92/20791 A1 | 11/1992 |
| WO | 93/01288 A1 | 1/1993 |
| WO | 93/04169 A1 | 3/1993 |
| WO | 93/23431 A1 | 11/1993 |
| WO | 94/02610 A1 | 2/1994 |
| WO | 94/10300 A1 | 5/1994 |
| WO | 94/16101 A2 | 7/1994 |
| WO | 94/18317 A1 | 8/1994 |
| WO | 94/29442 A2 | 12/1994 |
| WO | 9503832 A1 | 2/1995 |
| WO | 96/01313 A1 | 1/1996 |
| WO | 96/23898 A1 | 8/1996 |
| WO | 97/39721 A2 | 10/1997 |
| WO | 99/18953 A1 | 4/1999 |
| WO | 01/49717 A2 | 7/2001 |
| WO | 01/72783 A2 | 10/2001 |
| WO | 02/085396 A1 | 10/2002 |
| WO | 03/089622 A2 | 10/2003 |
| WO | 2004020610 A2 | 3/2004 |
| WO | 04/037373 A2 | 5/2004 |
| WO | 05/034737 A2 | 4/2005 |
| WO | 06/031931 A2 | 3/2006 |
| WO | 2006/031930 A2 | 3/2006 |
| WO | 07/041282 A2 | 4/2007 |
| WO | 07/053747 A2 | 5/2007 |
| WO | 2007/101224 A2 | 9/2007 |
| WO | 2008039445 A2 | 4/2008 |
| WO | 08/143876 A2 | 11/2008 |
| WO | 2008/141129 A1 | 11/2008 |
| WO | 2009/091815 A2 | 7/2009 |
| WO | 2009/129465 A2 | 10/2009 |
| WO | 2010/008860 A1 | 1/2010 |
| WO | 2010014905 A2 | 2/2010 |
| WO | 2010/031056 A2 | 3/2010 |
| WO | 2010/088498 A1 | 8/2010 |
| WO | 2010/141619 A1 | 12/2010 |
| WO | 2010/151827 A1 | 12/2010 |
| WO | 2011/022316 A1 | 2/2011 |
| WO | 2012/109238 A2 | 8/2012 |
| WO | 2012/138715 A2 | 10/2012 |
| WO | 2013/134774 A1 | 9/2013 |
| WO | 2013/142571 A2 | 9/2013 |
| WO | 2015/048331 A1 | 4/2015 |

OTHER PUBLICATIONS

Zhou, et al. HIV Protease Inhibitors Activate the Unfolded Protein Response in Macrophages: Implication for Atherosclerosis and Cardiovascular Disease. Mol. Pharmacol. 2005; 68(3): 690-700.*

Han, et al. IRE1α Kinase Activation Modes Control Alternate Endoribonuclease Outputs to Determine Divergent Cell Fates. Cell 138, 562-575 and supplemental data pp. 1-21.*

Calfon, et al. IRE1 couples endoplasmic reticulum load to secretory capacity by processing the XBP-1 mRNA. Nature, 2002; 92-96.*

Engel and Barton Unfolding new roles for XBP1 in immunity. Nature Immunology. 2010; 11(5): 365-367.*

Xu and Song The Role of CD40-CD 154 Interaction in Cell Immunoregulation. J Biomed Sci 2004;11:426-438.*

(56) References Cited

OTHER PUBLICATIONS

Chow, et al. Anti-HIV drugs for cancer therapeutics: back to the future? Lancet Oncol. 2009; 10:61-71.*
Boeglin et al. Soluble CD40L and TLR Agonist synergize Murine B Cell Proliferation. Eur. J. Immunol. 2009; 39(Suppl. 1), Monday Poster Sessions S55-S279. PB11/62: S163.*
Lucia et al. In Vitro and In Vivo Modulation of MDRI/P-Glycoprotein in HIV-Infected Patients Administered Highly Active Antiretroviral Therapy and Liposomal Doxorubicin. JAIDS, 2002; 30:369-378.*
Wang et al. Doxorubicin-Induced Systemic Inflammation is Driven by Upregulation of Toll-Like Receptor TLR4 and Endotoxin Leakage. Cancer Res. 2016; 76(22): 6631-6642.*
Wu et al. "Long Chain Omega-3 Polyunsaturated Fatty Acid Supplementation Alleviates Doxorubicin-Induced Depressive-Like Behaviors and Neurotoxicity in Rats: Involvement of Oxidative Stress and Neuroinflammation", Nutrients, 2016; 8(243): 1-15.*
Park et al. "Doxorubicin enhances CD4+ T-cell immune responses by inducing expression of CD40 ligand and 4-1BB", Internat. Immunopharmacol. 2009; 9: 1530-1539.*
Alderson et al. "CD40 Expression by Human Monocytes: Regulation by Cytokines and Activation of Monocytes by the Ligand for CD40", J. Exp. Med. 1993; 178: 669-674.*
Brüning "Analysis of Nelfinavir-Induced Endoplasmic Reticulum Stress", Met. Enzymol. 2011; 491: 127-142.*
Whiteside, T.L. "The tumor microenvironment and its role in promoting tumor growth," Oncogene, vol. 27: 5904-5912 (2008).
Whiteside, TL, "Immune suppression in cancer: effects on immune cells, mechanisms and future therapeutic intervention," Seminars in Cancer Biol., vol. 16(1): 3-15 (2006).
Wilson, et al., "Hepatocyte-directed gene transfer in vivo leads to transient improvement of hypercholesterolemia in low density lipoprotein receptor-deficient rabbits." J Biol Chem., vol. 267(2):963-967 (1992).
Wilson, et al., "Retrovirus-mediated transduction of adult hepatocytes" Proc Natl Acad Sci U S A., vol. 85(9):3014-3018 (1988).
Wilson, et al., "The use of mRNA display to select high-affinity protein-binding peptides" PNAS, USA, vol. 98(7):3750-3755 (2001).
Winoto, et al., "A novel, inducible and T cell-specific enhancer located at the 3' end of the T cell receptor alpha locus" EMBO J., vol. 8(3):729-733 (1989).
Wolff, et al., "Direct Gene Transfer Into Mouse Muscle in Vivo," Science, vol. 247: 1465-1468: (1990).
Wondisford, et al., "Cloning of the human thyrotropin beta-subunit gene and transient expression of biologically active human thyrotropin after gene transfection," Mol. Endocrinol. 2: 32-39 (1988).
Wong, et al., "Characterization of beta-thalassaemia mutations using direct genomic sequencing of amplified single copy DNA." Nature, vol. 330(6146):384-386 (1987).
Wouters, B. G., et al., "Hypoxia signalling through mTOR and the unfolded protein response in cancer," Nat Rev Cancer, vol. 8(11): 851-864(2008).
Wu, et al., "Receptor-mediated gene delivery and expression in vivo," J Biol Chem. , vol. 263(29):14621-14624 (1988).
Xia, X, et al., "Integrative analysis of HIF binding and transactivation reveals its role in maintaining histone methylation homeostasis," PNAS USA, vol. 106(11): 4260-4265 (2009).
Xu, t al., "The Role of CD40-CD 154 Interaction in Cell Immunoregulation," J Biomed Sci, vol. 11 :426-438 (2004).
Yan, Q., et al., "The hypoxia-inducible factor 2alpha N-terminal and C-terminal transactivation domains cooperate to promote renal tumorigenesis in vivo," Mol Cell Biol., vol. 27(6): 2092-102 (2007).
Schmalzing, et al., "Microchip electrophoresis: a method for high-speed SNP detection," Nucleic Acids Research, vol. 28(9): 1-6 (2000).

Ye, et al., "ER Stress Induces Cleavage of Membrane-Bound ATF6 by The Same Proteases That Process SREBPs" Mol Cell, vol. 6: 1355-1364 (2000).
Yeh, et at, "Cell surface antigens of human melanoma identified by monoclonal antibody" Proc Natl Acad Sci U S A. , vol. 76(6):2927-2931 (1979).
Yeh, et al., "A cell-surface antigen which is present in the ganglioside fraction and shared by human melanomas" Int. J. Cancer, vol. 29: 269-275 (1982).
Yoshida, et al., "Endoplasmic Reticulum Stress-Induced Fonnation of Transcription Factor Complex ERSF Including NF-Y (CBF) and Activating Transcription Factors 60. And 6p That Activates the Mammalian Unfolded Protein Response" Mol Cell Biol 21: 1239-1248,2001.
Yoshida, et al., "Identification of the cis-Acting Endoplasmic Reticulum Stress Response Element Responsible for Transcriptional Induction of Mammalian Glucose-Regulated Proteins" J. Biol. Chem., vol. 273: 33741-33749 (1998).
Yoshimura, et al., "Adenovirus-Mediated Transfer of a Recombinant al-Antitrypsin Gene to the Lung Epithelium In Vivo," Science, vol. 252: 431-434 (1991).
Yoshimura, T. et al., "Multiple cDNA closes encoding nuclear proteins that bind to the tax dependent enhancer of HTLV-1: all contain a leucine zipper structure and basic amino acid domain," EMBO, vol. 9(8):2537-2542 (1990).
Zamore, P. et al., "RNAI: Double-Stranded RNA Directs the ATP-Dependent Cleavage of mRNA at 21 to 23 Nucleotide Intervals," Cell, vol. 101:25-33 (2000).
Zervos, et al., "Mxi1, a protein that specifically interacts with Max to bind Myc-Max recognition sites" Cell 72: 223-232, (1993).
Zhang et al., "GRP78, but not Protein-disulfide Isomerase, Partially Reverses Hyperglycemia-induced Inhibition of Insulin Synthesis and Secretion in Pancreatic-cells," J. Biol. Chem., 284(8): 52-89-5298 (2009).
Zhang, J. et al., "Insulin inhibits transcription of IRS-2 gene in rat liver through an insulin response element (IRE) that resembles IREs of other insulin-repressed genes," PNAS, vol. 98(7): 3756-3761 (2001).
Zhang, K. et al., "The unfolded protein response transducer IRE1alpha prevents ER stress-induced hepatic steatosis," EMBO J., vol. 30(7):1357-1375 (2011).
Zhang L. et al., "Intratumoral T cells, recurrence, and survival in epithelial ovarian cancer," N Engl J Med., vol. 348:203-213 (2003).
Zhang, Q. et al., "Control of cyclin D1 and breast tumorigenesis by the EgIN2 prolyl hydroxylase," Cancer Cell, vol. 16(5): 413-424 (2009).
Zhao et al., "Endoplasmic reticulum stress in health and disease," Current Opinion in Cell Biology, vol. 18: 444-452 (2006).
Zhou, H. et al., "HIV protease inhibitors increase TNF-alpha and IL-6 expression in macrophages: involvement of the RNA-binding protein HuR," Atherosclerosis., vol. 195(1):e134-143 (2007).
Zhou, J., et al., "The crystal structure of human IRE1 luminal domain reveals a conserved dimerization interface required for activation of the unfolded protein response," PNAS USA, vol. 103(39):14343-14348 (2006).
Zimmet, et al., "Global and societal implications of the diabetes epidemic" Nature., vol. 414(6865):782-787 (2001).
Zou, W., "Immunosuppressive networks in the tumour environment and their therapeutic relevance," Nat Rev Cancer, vol. 5: 263-274 (2005).
Zubler, "Key Differentiation steps in normal C cells and in myeloma cells," Semin Hematol., vol. 34 (Supp 1) 13-22 (1997).
Zuckermann, et al., "Discovery of nanomolar ligands for 7-transmembrane G-protein-coupled receptors from a diverse N-(substituted)glycine peptoid library" J Med Chem., vol. 37(17):2678-2685 (1994).
Pinkert, et al., "An Albumin Enhancer Located 10 kb Upstream Functions Along With Its Promoter to Direct Efficient, Liver-Specific Expression in Transgenic Mice" Genes Dev., vol. 1: 268-277 (1987).
Piret, J.P., et al., "CoCl2, a chemical inducer of hypoxia-inducible factor-1, and hypoxia reduce apoptotic cell death in hepatoma cell line HepG2," Ann N Y Acad Sci., vol. 973, 443-447(2002).

(56) References Cited

OTHER PUBLICATIONS

Prols et al., "Upregulation of the Cochaperone Mdg1 in Endothelial Cells is Induced by Stress and During in vitro Angiogenesis," Exp. Cell Res., vol. 269: 42-53 (2001).
Quantin, et al., "Adenovirus as an expression vector in muscle cells in vivo," PNAS USA, vol. 89(7): 2581-2584 (1992).
Queen, et al., "Immunoglobin Gene Transcription is Activated by Downstream Sequence Elements," Cell, vol. 33: 741-748 (1983).
Rakha, E.A., et al., "Triple-negative breast cancer: distinguishing between basal and nonbasal subtypes," Clin Cancer Res., vol. 15(7): 2302-2310 (2009).
Randall, et al., "Interleukin-5 (IL-5) and IL-6 define two molecularly distinct pathways of B-cell differentiation," Mol Cell Biol., vol. 13(7):3929-3936 (1993).
Rapoport et al., "Interleukin 4 Reverses T Cell Proliferative Unresponsiveness and Prevents the Onset of Diabetes in Nonobese Diabetic Mice," J. Exp. Med., vol. 178:87-99 (1993).
Reimold, A.M. et al., "An essential role in liver development for transcription factor XBP-1," Genes and Devolpment, vol. 14:152-157 (2000).
Rengarajan, et al. "Sequential involvement of NFAT and EGR transcription factors in FasL regulation," Immunity, vol. 12(3):293-300 (2000).
Ricardo, S., et al., "Breast cancer stem cell markers CD44, CD24 and ALDH1: expression distribution within intrinsic molecular subtype," J Clin Pathol., vol. 64(11):937-946 (2011).
Richardson, et al., "Phenotypic knockout of the high-affinity human interleukin 2 receptor by intracellular single-chain antibodies against the alpha subunit of the receptor" PNAS, USA, vol. 92(8): 3137-3141 (1995).
Robinson, M.D., et al., "A scaling normalization method for differential expression analysis of RNA-seq data," Genome Biology, vol. 11, R25 (2010).
Roby, K.F., et al., "Development of a syngeneic mouse model for events related to ovarian cancer," Carcinogenesis, vol. 21: 585-591 (2000).
Romero-Ramirez, Lorenzo et al., "X box-binding protein 1 regulates angiogenesis in human pancreatic adenocarcinomas," Transl. Oncol., vol. 2(1):31-38 (2009).
Ron, D. et al., "Signal integration in the endoplasmic reticulum unfolded protein response," Nature Reviews Molecular Cell Biology, vol. 8:519-529 (Jul. 2007).
Rondinone, "Therapeutic potential of RNAi in metabolic diseases," BioTechniques, vol. 40: S31-S36 (2006).
Rong, J. et al., "Bifunctional Apoptosis REgulator (BAR), an endoplasmic reticulum-associated E3 ubiquitin ligase, modulates BI-1 protein stability and function in ER stress," Journal of Biological Chemistry, vol. 286 (2), pp. 1453-1463 (2010).
Rosenbaum, et al., "Temperature-gradient gel electrophoresis. Thermodynamic analysis of nucleic acids and proteins in purified form and in cellular extracts," Biophys Chem., vol. 265: 1275 (1987).
Rosenfeld, et al., "Adenovirus-Mediated Transfer of a Recombinant alpha 1-Antitrypsin Gene to the Lung Epithelium In Vivo" Science, vol. 252: 431-434 (1991).
Rosenfeld, et al., "In vivo transfer of the human cystic fibrosis transmembrane conductance regulator gene to the airway epithelium" Cell, vol. 68: 143-155 (1992).
Rossi, et al., "Therapeutic Antisense and Ribozymes" Br. Med. Bull., vol. 51: 217-225 (1995).
Rudge, et al., "Interleukin 4 reduces expression of inhibitory receptors on B cells and abolishes CD22 and Fc gamma RII-mediated B cell suppression," J Exp Med. , vol. 195(8):1079-1085 (2002).
Saiki, et al., "Analysis of Enzymatically Amplified (3-Globin and HLA-DQa DNA With Allele-Specific Oligonucleotide Probes" Nature, vol. 324: 163 (1986).
Saiki, et at., "Genetic analysis of amplified DNA with immobilized sequence-specific oligonucleotide probes," PNAS. USA, vol. 86(16): 6230-6234 (1989).
Saleeba, et al., "Chemical cleavage of mismatch to detect mutations," Methods Enzymol., vol. 217: 286-295 (1992).
Saltiel, et al., "Insulin signalling and the regulation of glucose and lipid metabolism," Nature., vol. 414(6865):799-806 (2011).
Samoilova, et al., "IL-6-deficient mice are resistant to experimental autoimmune encephalomyelitis: roles of IL-6 in the activation and differentiation of autoreactive T cells," J Immunol., vol. 161(12):6480-6486 (1998).
Samulski, et al., "Helper-free stocks of recombinant adeno-associated viruses: normal integration does not require viral gene expression," J. Virol <https://www.ncbi.nlm.nih.gov/pmc/articles/PMC250975/>., vol. 63(9): 3822-3828 (1989).
Sanger, et al., "DNA Sequencing With Chain-Terminating Inhibitors" PNAS, vol. 74(12): 5463-5467 (1977).
Sato, E., Olson, et al "Intraepithelial CD8+ tumor-infiltrating lymphocytes and a high CD8+/regulatory T cell ratio are associated with favorable prognosis in ovarian cancer," PNAS USA, vol. 102:18538-18543 (2005).
Satpathy, A.T., et al., "Zbtb46 expression distinguishes classical dendritic cells and their committed progenitors from other immune lineages," J Exp Med., vol. 209: 1135-1152 (2012).
Scarlett, U.K., et al. "Ovarian cancer progression is controlled by phenotypic changes in dendritic cells," J Exp Med. (2012).
Scarlett, U.K., et al., "In situ stimulation of CD40 and Toll-like receptor 3 transforms ovarian cancer-infiltrating dendritic cells from immunosuppressive to immunostimulatory cells," Cancer Res., vol. 69, 7329-7337 (2009).
Scheuner, et al., "Translational Control is Required for the Unfolded Protein Response and In Vivo Glucose Homeostasis," Mol. Cell., vol. 7: 1165 (2001).
Schmitz-Peiffer, et al., "IRS-I Regulation in Health and Disease" fUBMB Life, vol. 55(7): 367-374 (2003).
Schrami, B.U., et al., "Genetic tracing via DNGR-1 expression history defines dendritic cells as a hematopoietic lineage," Cell, vol. 154: 843-858 (2013).
Schwab, L. P., et al., "Hypoxia-inducible factor 1? promotes primary tumor growth and tumor-initiating cell activity in breast cancer," Breast Cancer Res., vol. 14(1): R6 (2012).
Scott, et al., "Searching for Peptide Ligands With an Epitope Library" Science, vol. 249: 386.-390: (1990).
Searle, et al., "Building a metal-responsive promoter with synthetic regulatory elements" Mol. Cel. Biol, vol. 5: 1480-1489 (1985).
Seed, et al. "An LF A-3 cDNA Encodes a Phosphplipid-Linked Membrane Protein homologous to Its Receptor CD2" Nature, vol. 329: 840 (1987).
Semenza, G .L., "HIF-1, O(2), and the 3 PHDs: how animal cells signal hypoxia to the nucleus," Cell, vol. 107(1):1-3 (2011).
Semenza, G. L., "Defining the role of hypoxia-inducible factor 1 in cancer biology and therapeutics," Oncogene, vol. 29(5):625-634 (2010).
Semenza, G. L., "Targeting HIF-1 for cancer therapy," Nat Rev Cancer, vol. 3(10): 721-732 (2003).
Sharp, et al., "RNA Interference" P.D. 287: 2431-2432 (2000).
Shen, et al, "ER stress regulation of ATF6 localization by dissociation of BiP/GRP78 Binding and unmasking of Golgi localization signals." Dev Cell., vol. 3(1):99-111 (2002).
Shi, et al., "Identification and Characterization of Pancreatic Eukaryotic Initiation Factor 2 a-Subunit Kinase, PEK, Involved in Translational Control" Mol. Cell Biol., vol. 18: 7499-7509 (1998).
Shi, et al., "When Translation Meets Metabolism: Multiple Links to Diabetes" Endocrine Reviews, vol. 24(1): 91-101 (2003).
Sidrauski, et al., "The Transmembrane Kinase Irelp is a Site-Specific Endonuclease That Initiates mRNA Splicing in the Unfolded Protein Response" Cell, vol. 90: 1031-1039 (1997).
Sidrauski, et al., "RNA ligase is required for regulated mRNA splicing in the unfolded protein response" Cell., vol. 87(3):405-413 (1996).
U.S. Appl. No. 15/441,103, filed Feb. 23, 2017, Laurie H. Glimcher.
U.S. Appl. No. 15/024,215, filed Mar. 23, 2016, Juan R. Cubillos-Ruiz.
U.S. Appl. No. 14/383,687, filed Sep. 23, 2016, G. Yakovleva.
U.S. Appl. No. 14/383,687, filed Feb. 8, 2016, R. Schnizer.

(56) References Cited

OTHER PUBLICATIONS

Silze. T. et.al., "The fibroblast: sentinel cell and local immune modulator in tumor tissue," International Journal of Cancer, vol. 108:173-180 (2004).
Singh, S.P., et al., "Fat accumulation in Caenorhabditis elegans triggered by the electrophilic lipid peroxidation product 4-hydroxynonenal (4-HNE)," Aging, vol. 1: 68-80 (2009).
Sjolander, et al., "Integrated Fluid Handling System for Biomolecular Interaction Analysis" Anal. Chem., vol. 63: 2338-2345 (1991).
Smalley, M., et al., "Stem cells and breast cancer: A field in transit," Nat Rev Cancer, vol. 3(11):832-844 (2003).
Smyth, G. K., et al., "Statistical issues in cDNA microarray data analysis," Methods Mol Biol., vol. 224: 111-136 (2003).
So, J.S., et al., "Silencing of lipid metabolism genes through IRE1alpha-mediated mRNA decay lowers plasma lipids in mice," Cell Metab., vol. 16:487-499 (2012).
Songyang, et al., "SH2 Domains Recognize Specific Phosphopeptide Sequences," Cell 72: 767-778 (1993).
Sriburi, R., et al., "XBP1: a link between the unfolded protein response, lipid biosynthesis, and biogenesis of the endoplasmic reticulum," J Cell Biol., vol. 167: 35-41 (2004).
Stingl, J., et al., "Molecular heterogeneity of breast carcinomas and the cancer stem cell hypothesis," Nat Rev Cancer, vol. 7(10):791-799 (2007).
Stoerker, et al., "Rapid Genotyping by MALDI-Monitored Nuclease Selection From Probe; Libraries" Nature Biotechnology, vol. 18: 1213 (2000).
Stoichet, et al., "Structure-Based Discovery OfInhibitors OfThymidylate Synthase" Science, vol. 259: 1445 (1993).
Sui, et al., "A DNA vector-based RNAi technology to suppress gene expression in mammalian cells" PNAS, USA., vol. 99(8):5515-5520 (2002).
Supplementary Partial European Search Report for Application No. 03749316.0, dated Nov. 26, 2007.
Szabo, et al., "Surface Plasmon Resonance and Its Use in Biomolecular Interaction Analysis (BIA)" Curro Opin. Struct. Biol., vol. 5: 699-705 (1995).
Walter, P., et al., "The unfolded protein response: from stress pathway to homeostatic regulation," Science, vol. 334 (6059): 1081-1086 (2011).
Takatsu, et al., "Cytokines Involved in B-Cell Differentiation and Their Sites of Action," Proc Soc Exp Biol & Med., vol. 215: 121-133 (1997).
Tan, E.Y., et al., "The key hypoxia regulated gene CAIX is upregulated in basal-like breast tumours and is associated with resistance to chemotherapy," J Cancer, vol. 100(2):405-411 (2009).
Tang, Q., et al., "A comprehensive view of nuclear receptor cancer cistromes," Cancer Res., vol. 71(22): 6940-6947 (2011).
Thermo Scientific Pierce Protein Interaction Technical Handbook, version 2, 73 pages (2010).
Thomas, et al., "Site-Directed Mutagenesis by Gene Targeting in Mouse Embryo-Derived Stem Cells" Cell 51: 503 (1987).
Thompson, et al., "BAFF-R, A Newly Identified TNF Receptor That Specifically Interacts With BAFF." Science 293: 2108-2111 (2001).
Tirasophon, et al. "A stress response pathway from the endoplasmic reticulum to the nucleus requires a novel bifunctional protein kinase/Endoribonuclease (Ire1p) in mammalian cells," Genes Dev., vol. 12(12):1812-1824 (1998).
Tirasophon, et al., "The Endoribonuclease Activity of Mammalian IREI Autoregulates Its mRNA and is Required for the Unfolded Protein Response" Genes Dev., vol. 14: 2725-2736, (2000).
Toh, et al., "Isolation and Characterization of a Rat Liver Alkaline Phosphatase Gene," Eur. J Biochem., vol. 182: 231-238 (1989).
Tratschin, et al., "A Human Parvovirus, Adeno-Associated Virus, As a Eucary," Mol. Cell. Biol., vol. 4: 2072-2081 (1985).
Tratschin, et al., "Adeno-associated virus vector for high-frequency integration, expression, and rescue of genes in mammalian cells" Mol Cell Biol., vol. 5(11):3251-60 (1985).
Tratschin, et al., "Genetic analysis of adeno-associated virus: properties of deletion mutants constructed in vitro and evidence for an adeno-associated virus replication function," J Virol., vol. 51(3):611-619 (1984).
Urano, et al., "IREI and Efferent Signaling From the Endoplasmic Reticulum." J Cell Sci., vol. 113(21): 3697-3702 (2000).
Tsunekawa et al., "Protection of pancreatic-cells by exendin-4 may involve the reduction of endoplasmic reticulum stress: in vivo and in vitro studies," J. Endocrinology, 193: 65-74 (2007).
Turner, et al., "Blimp-1, a novel zinc finger-containing protein that can drive the maturation of B lymphocytes into immunoglobulin-secreting cells," Cell, vol. 77: 297-306 (1994).
Tuschl, et al., "Targeted mRNA degradation by double-stranded RNA in vitro," Genes Dev., vol. 13(24):3191-3197 (1999).
Uysal, et al., "Protection from obesity-induced insulin resistance in mice lacking TNF-alpha function" Nature, vol. 389: 610-614 (1997).
Wen, et al., "Identification of c-myc promoter-binding protein and X-box binding protein 1 as Interleukin-6 target genes in human multiple myeloma cells" Int. Journal of Oncology, vol. 15: 173-178 (1999).
Vargo-Gogola, T. et al., "Modelling breast cancer: one size does not fit all," Cancer, vol. 7(9):659-672 (2007).
Visvader, J.E., et al., "Cancer stem cells in solid tumours: accumulating evidence and unresolved questions," Nat Rev Cancer, vol. 8(10):755-768 (2008).
Vladykovskaya, E., et al., "Lipid peroxidation product 4-hydroxy-trans-2-nonenal causes endothelial activation by inducing endoplasmic reticulum stress," J Biol Chem., vol. 287: 11398-11409 (2012).
Volkmann, K., et al.,"Potent and selective inhibitors of the inositol-requiring enzyme 1 endoribonuclease," J Biol Chem., vol. 286 (14):12743-12755 (2011).
Von Herrath et al., "Animal models of human type 1 diabetes," Nature Immunology (2009), 10(2):129-132.
Wagner, et al., "Gene inhibition using antisense oligodeoxynucleotides" Nature , vol. 372: 333-335 (1994).
Werge, et al., "Cloning and Intracellular Expression of a Monoclonal Antibody to the 21 ras Protein" FEBS Letters 274: 193-198 (1990).
Wang, et al., "Activation of ATF6 and an ATF6 DNA binding site by the endoplasmic reticulum stress response," J Biol Chem., vol. 275(35):27013-27020 (2000).
Wang, et al., "Cloning of mammalian Ire1 reveals diversity in the ER stress responses," EMBO J., vol. 17(19):5708-5717 (1998).
Wang, FM et al., "Resveratrol triggers the pro-apoptotic endoplasmic reticulum stress response and represses pro-survival XBP1 signaling in human multiple myeloma cells," Exp Hematol., vol. 39(10):999-1006 (2011).
Wang, Y., et al., "Targeting HIF1 eliminates cancer stem cells in hematological malignancies," Cell Stem Cell, vol. 8(4): 399-411(2011).
Weintraub, et al., "Antisense RNA As a Molecular Tool for Genetic Analysis" Reviews—Trends in Genetics , vol. 1(1): (1986).
Welch, et al., "Influence of Molecular and Chemical Chaperones on Protein Folding," Cell Stress Chaperones, vol. 1:109-115 (1996).
Welch, et al., "Mammalian stress response: cell physiology, structure/function of stress proteins, and implications for medicine and disease" Physiol Rev. , vol. 72(4):1063-1081(1992).
Welihinda, et al., "The unfolded protein response pathway in *Saccharomyces cerevisiae.* Oligomerization and trans-phosphorylation of Ire1p (Ern1p) are required for kinase activation," J Biol Chem., vol. 271(30):18181-18187 (1996).
Flesken-Nikitin, A., et al., "Induction of carcinogenesis by concurrent inactivation of p53 and Rb1 in the mouse ovarian surface epithelium," Cancer Res., vol. 63: 3459-3463. (2003).
Flotte, et al., "Expression of the Cystic Fibrosis Transmembrane Conductance Regulator From a Novel Adeno-Associated Virus Promoter" J Biol. Chem., vol. 268: 3781-3790 (1993).
Flotte, et al., "Gene Expression From Adeno-Associated Virus Vectors in Airway Epithelial Cells," Am J Respir. Cell. Mol. Biol., vol. 7: 349-356 (1992).
Fodor, et al., "Multiplexed Biochemical Assays With Biological Chips" Nature , vol. 364: 555-556 (1993).

(56) References Cited

OTHER PUBLICATIONS

Foulkes, W. D., et al., "Triple-negative breast cancer," N Engl J Med., vol. 363(20):1938-1948 (2010).
Galfre, et al., "Antibodies to Major Histocompatibility Antigens Produced by Hybrid Cell Lines," Nature, vol. 266: 550-552 (1977).
Gallop, et al., "Applications of Combinatorial Technologies to Drug Discovery. I. Background and Peptide Combinatorial Libraries" J. Med Chem., vol. 37: 1233 (1994).
Garrad, et al., "FAB Assembly and enrichment in a Monovalent Phage Display System" Bio/Technology, vol. 9: 1373-1377 (1991).
Gaultier, et al., "a-DNA IV: a-Anomeric and p-Anomeric Tetrathymidylates Covalently Linked to Intercalating Oxazolopyridocarbazole. Synthesis, Physicochemical Properties and Poly (rA) Binding," Nucleic Acids. Res., vol. 15: 6625-6641 (1987).
GenBank Accession No. NP_005071, Liou H.C. et al., "An HLA-DR alpha promoter DNA-binding is expressed ubiquitously and maps to human chromosomes 22 and 5," Immunogenetics, vol. 34(5):286-292 (1991), 2 pages (2000).
Ginestier, C., et al., "ALDH1 is a marker of normal and malignant human mammary stem cells and a predictor of poor clinical outcome," Cell Stem Cell, vol. 1(5): 555-567 (2007).
Ginsberg, H. et al., "Metabolic Syndrome: Focus on Dyslipidemia," Obesity, vol. 14 (Supp 1): 41S-49S( 2006).
Gomez, B.P., et al., "Human X-box binding protein-1 confers both estrogen independence and antiestrogen resistance in breast cancer cell lines," FASEB J., vol. 21:4013-4027 (2007).
Gonzalez, et al., "Mechanism of Non-Spliceosomal mRNA Splicing in the Unfolded Protein Response Pathway," EMB, vol. 18(11): 3119-3132 (1999).
Goodford, et al., "A Computational Procedure for Determining Energetically Favorable Binding Sites on Biologically Important Macromolecules," J Med. Chem., vol. 28: 849 (1985).
Gossen, et al., "Tight Control of Gene Expression in Mammalian Cells by Tetracycline-Responsive Promoters," PNAS, USA, vol. 89: 5547-5551 (1992).
Gram, et al., "In vitro selection and affinity maturation of antibodies from a naive combinatorial immunoglobulin library" PNAS, vol. 89: 3576-3580 (1992).
Griffiths, et al., "Human Anti-Self Antibodies With High Specificity From Phage Display Libraries" EMBO J., vol. 12: 725-734 (1993).
Gross, et al., "BCL-2 Family Members and the Mitochondria in Apoptosis" Genes Dev., vol. 13:1899 (1999).
Haj-Ahmad, "Development of a Helper-Independent Human Adenovirus Vector and Its Use in the Transfer of the Herpes Simplex Virus Thymidine Kinase Gene," J. Viral., vol. 57:267 (1986).
Hall, et al., "Expression and Regulation of *Escherichia coli* LacZ Gene Fusions in Mammalian Cells," J. Mol. Appl. Gen., vol. 2: 101-109 (1983).
Hallek, et al., "Multiple Myeloma: Increasing Evidence for a Multistep Transformation Process," Blood, vol. 91(1): 3-21 (1998).
Hamanishi, J., et al."Programmed cell death 1 ligand 1 and tumor-infiltrating CD8+ T lymphocytes are prognostic factors of human ovarian cancer," PNAS, USA, vol. 104: 3360-3365 (2007).
Han, L.Y., et al., "HLA class I antigen processing machinery component expression and intra tumoral T-Cell infiltrate as independent prognostic markers in ovarian carcinoma," Clin Cancer Res., vol. 14: 3372-3379 (2008).
Hanahan, D. et al.,"Hallmarks of Cancer: The Next Generation," Cell, vol. 144:646-674 (2011).
Harding, et al, "Transcriptional and Translational Control in the Mammalian Unfolded Protein Response," Annu. Rev. Cell Dev. Biol., vol. 18: 575 (2002).
Harding, et al., "Enodplasmic Reticulum Stress and the Development of Diabetes" Diabetes, vol. 51(3): S455-S461 (2002).
Hay, et al., "Bacteriophage Cloning and *Escherichia coli* Expression of a Human IgM Fab" Hum Antibod Hybridomas, vol. 3: 81-85 (1992).

Hayahsi, K. et al., "PCR-SSCP: a simple and sensitive method for detection of mutations in the genomic DNA," PCR Methods Appl., vol. 1(1):34-38 (1991).
Hayashi, "PCR-SSCP: A Method for Detection of Mutations," Genet Anal Tech App., vol. 9: 73-79 (1992).
Heddleston, J.M., et al., "Hypoxia inducible factors in cancer stem cells," Br J Cancer, vol. 102, 789-795 (2009).
Herber, D.L., et al., "Lipid accumulation and dendritic cell dysfunction in cancer," Nat Med., vol. 16: 880-886 (2010).
Hermonat, et al., "Use of Adeno-Associated Virus as a Mammalian DNA Cloning Vector: Transduction of Neomycin Resistance Into Mammalian Tissue Culture Cells," PNAS, USA, vol. 81: 6466-6470 (1984).
Hershkowitz, "Identification of conserved gene expression features between murine mammary carcinoma models and human breast tumors," Genome Biol., vol. 8(5):R76 (2007).
Herz, et al., "Adenovirus-Mediated Transfer of Low Density Lipoprotein Receptor Gene Acutely Accelerates Cholesterol Clearance in Normal Mice," PNAS, USA, vol. 90: 2812-2816 (1993).
Hetz, C., et al., "Targeting the unfolded protein response in disease," Nature Reviews Drug Discovery, vol. 12:703-719 (2013).
Hetz, Claudio et al., "Unfolded protein response transcription factor XBP-1 does not influence prion replication of pathogenesis," PNAS, vol. 105(2):757-762 (2008).
Hodge, et al., "Hyperproliferation and Dysregulation of IL-4 Expression in NF-ATp-Deficient Mice," Immunity, vol. 4: 397-405 (1996).
Hoogenboom, et al., "Multi-Subunit Proteins on the Surface of Filamentous Phage: Methodologies for Displaying Antibody (Fab) Heavy and Light Chains" Nuc Acid Res., vol. 19:4133-4137 (1991).
Horwell, et al., "'Targeted' Molecular Diversity: Design and Development Non-Peptide Antagonists for Cholecystokinin and Tachykinin Receptors" Immunopharmacology, vol. 33: 68 (1996).
Houghten, et al., "Generation and Use of Synthetic Peptide Combinatorial Libraries for Basic Research and Drug Discovery," Nature, vol. 354: 84-86 (1991).
Houghten, et al., "The Use of Synthetic Peptide Combinatorial Libraries for the Identification of Bioactive Peptides" Biotechnique, vol. 13: 412-421 (1992).
Huang da, et al., "Systematic and integrative analysis of large gene lists using DAVID bioinformatics resources," Nature Protocols, vol. 4: 44-57 (2009).
Huarte, E., et al., "Depletion of dendritic cells delays ovarian cancer progression by boosting antitumor immunity," Cancer Res., vol. 68:7684-7691 (2008).
Huber, et al., "Retroviral-Mediated Gene Therapy for the Treatment of Hepatocellular Carcinoma: An Innovative Approach for Cancer Therapy," PNAS, USA, vol. 88:8039-8043 (1991).
Hudis CA, "Triple-negative breast cancer: an unmet medical need," Oncologist, vol. 16 Suppl 1:1-11 (2011).
Hughes, et al., "Apoptotic Nuclease Assays" Methods in Enzymol., vol. 322: 47-62 (2000).
Hur, K.Y. et al., "IRE1 activation protects mice against acetaminophen-induced hepatotoxicity," The EMBO Journal, vol. 30(7):1357-1418 (2012).
Huse, et al., "Generation of a Large Combinatorial Library of the Immunoglobulin Repertoire in Phage Lambda" Science, vol. 246: 1275-1281 (1989).
Hussein, Y.R., et al., "Glut-1 Expression Correlates with Basal-like Breast Cancer," vol. 4(6):321-327 (2011).
Barnard GA, "A New Test for 2×2 Table," Nature, vol. 156:177-178(1945).
Barnard GA, "Significan Tests for 2×2 Tables," Biometrika, vol. 34: 123-138 (1947).
Barnett, B. et al., "Regulatory T cells in ovarian cancer biology and therapeutic potential," Am J Reprod Immunol ., vol. 54: 369-377 (2005).
Ben-Baruch, A., "Inflammation-associated immune suppression in cancer: the roles played by cytokines, chemokines and additional mediators," Seminars in Cancer Biology , vol. 16:38-52 (2006).
Blick, T., et al., "Epithelial Mesenchymal Transition Traits in Human Breast Cancer Cell Lines Parallel the CD24hi/CD24lo/—

(56) References Cited

OTHER PUBLICATIONS

Stem Cell Phenotype in Human Breast Cancer," J Mammary Gland Biol Neoplasia, vol. 15: 235-252 (2010).
Cassol et al., "Stability of Dried Blood Spot Specimens for Detection of Human Immunodeficiency Virus DNA by Polymerase Chain Reaction," Journal of Clinical Microbiology, vol. 30(12):3039-3042 (1992).
Conejo-Garcia, J.R., et al., "Tumor-infiltrating dendritic cell precursors recruited by a beta-defensin contribute to vasculogenesis under the influence of Vegf-A," Nat Med. vol. 10: 950-958. (2004).
Cubillos-Ruiz, J.R.,et al. "Reprogramming Tumor-Associated Dendritic Cells In Vivo Using miRNA Mimetics Triggers Protective Immunity against Ovarian Cancer," Cancer Research, vol. 72(7):1683-1693 (2012).
Curiel, T.J., et al., "Blockade of B7-H1 improves myeloid dendritic cell-mediated antitumor immunity," Nat Med., vol. 9: 562-567 (2003).
Dean M. et al.,"Tumour Stem Cells and Drig Resistance," Nat Rev Cancer, vol. 5:275-284 (2005).
Dranoff, G., "Cytokines in cancer pathogenesis and cancer therapy," Nature Reviews Cancer, vol. 4: 11-22 (2004).
Dunn, GP et al., "Cancer immunoediting: from immunosurveillance to tumor escape," Nature Immunology, vol. 3: 991-998 (2002).
Evans, J. et al., "Enhancement of antigen-specific immunity via the TLR4 Liglands MPL adjuvant and Ribi.529," Expert Rev Vaccines, vol. 2: 219-229 (2003).
Healy, S.J., et al., "Targeting the endoplasmic reticulum-stress response as an anticancer strategy.," Eur J Pharmaco., vol. 1625(1-3): 234-246 (2009).
Kaufman, et al., "The Unfolded Protein Response in Nutrient Sensing and Differentiation," Nat. Rev. Mol. Cell Biol., vol. 3: 411 (2002).
Langer R. et al, Biocompatibility of polymeric delivery systems for Macromolecules, J. Biomed Mater Res., vol. 15:167-277 (1981).
Lebrun, P., et al., "Dissociation by methylamine of insulin release from glucose-induced electrical activity in isolated mouse islets of Langerhans," Metabolism, Clinical and Experimental, W.B. Saunders Co., Philadelphia, PA, 34(12): 1122-1127 (Dec. 1, 1985).
Lee, et al., "Mammalian Stress Response: Induction of the Glucose-Regulated Protein Family," Curr. Opin. Cell Biol., vol. 4: 267-273 (1992).
Leen, A.M., et al., "Monoculture-derived T lymphocytes specific for multiple viruses expand and produce clinically relevant effects in immunocompromised individuals," Nat Med., vol. 12: 1160-1166 (2006).
Liu, et al., "Regulation of B-Cell Commitment to Plasma Cells or to Memory B Cells." Sem Immunol., vol. 9: 235-240 (1997).
Mani, S. et al., "The Epithelial-Mesenchymal Transition Generates Cells with Properties of Stem Cells," Cell, vol. 133: 704-715 (2008).
McDonnell, V.M., "Antisense-oligonucleotide therapy," N Eng. J Med., vol. 334:316-318 (1996).
Mineo et al., "Chemical Specificity of Short-Chain Fatty Acids in stimulating insulin and glucagon secretion in sheep," American Journal of Physiology., vol. 267(2, Pt. 1), E234-E241(1994).
Murphy, I. et al., "Synucleinopathies: a pathological and molecular review," Clinical Neurosci Res., 445-455 (2001).
Rasanen, K. et al., "Activation of fibroblasts in cancer stroma," Experimental Cell Research, vol. 316: 2713-2722 (2010).
Reed, JC, "Mechanisms of apoptosis avoidance in cancer," Current Opinion in Oncology, vol. 11: 68-75 (1999).
Rossolini, Y. et al., "Use of deoxyinosine-containing primers vs degenerate primers for polymerase chain reaction based on ambiguous sequence information," Mol Cell, vol. 8:91-65 (1994).
Sharp, P.A., et al., "RNA Interference," Science, vol. 287 (5462):2431-2433 (2000).
Sidman, KR., et al., "Controlled release of macromolecules and pharmaceuticals from synthetic polypeptides based on glutamic acid," Biopolymers, vol. 22(1): 547-556(1983).

Singh, S.P., et al., "Role of the electrophilic lipid peroxidation product 4-hydroxynonenal in the development and maintenance of obesity in mice," Biochemistry, vol. 47: 3900-3911 (2008).
Suckow, M., "Cancer vaccines: Harnessing the potential of antitumor immunity," The Veterinary Journal, vol. 198:28-33 (2013).
Trojanowski J.Q., "Parkinson's Disease and Related Synucleinopathies are a New Class; of Nervous System Amyloidoses," Neurotoxicology, vol. 23(4-5):457-460 (2002).
Wilcox, WR et al, "Lysosomal storage disorders: the need for better pediatric recognition and comprehensive care," J. Pediatric, vol. 144: S3-S4 (2004).
Yuan, et al., "Reversal of Obesity-and-Diet-Induced Insulin Resistance with Salicylates or Targeted Disruption of ikkbeta," Science, vol. 293: 1673 (2001).
Zanoboni, A., et al., "Stimulation of insulin secretion in man by oral glycerol administration," Metabolism, Clinical and Experimental, W.B. Saunders Co., Philadelphia, PA,vol. 25(1): 41-45 (Jan. 1, 1976).
Chen, H. et al. "Regulation and Activities of .alpha.-Fetoprotein," Critical Reviews in Eukaryotic Gene Expression, vol. 7(1&2):11-41 (1997).
Chen, X., et al., "XBP1 promotes triple-negative breast cancer by controlling the HIF1 alpha pathway," Nature, vol. 508: 103-107 (2014).
Chen, Y. et al., "Identification of mitogen-activated protein kinase signaling pathways that confer resistance to endoplasmic reticulum stress in *Saccharomyces cerevisiae*," Mol Cancer Res., vol. 3(12):669-677 (2005).
Cho, et al., "An Unnatural Biopolymer" Science, vol. 261:1303 (1993).
Chow, et al., "Anti-HIV drugs for cancer therapeutics: back to the future?," Lancet Oncol., vol. 10:61-71 (2009).
Chowdhury, et al., "Long-Term Improvement of Hypercholesterolemia After ex Vivo Gene Therapy in LD LR-Deficient Rabbits," Science, vol. 254: 1802-1805 (1991).
Clarke, M.F., et al., "Cancer stem cells-perspectives on current status and future directions: AACR Workshop on cancer stem cells," Cancer Res., vol. 66(19):9339-9344 (2006).
Clauss, et al., "The Basic Domain/Leucine Zipper Protein hXBP-I Preferentially Binds to and Transactivates CRE-like Sequences Containing an ACGT Core" Nucleic Acids Research, vol. 24: 1855 (1996).
Clauss, I.M. et al. "In Situ Hybridization Studies Suggest a Role for the Basic Region-Leucine Zipper Protein hXBP-1 in Exocrine Gland and Skeletal Development During Mouse Embryogenesis," Dev. Dynamics 197:146-156 (1993).
Collison, K.S. et al., "Effect of dietary monosodium glutamate on trans fat-induced nonalcoholic fatty liver disease," The Journal of Lipid Research, vol. 50 (8): 1521-1537 (2008).
Conejo-Garcia, J.R. et al., "Vascular leukocytes contribute to tumor vascularization," Blood, vol. 105: 679-681 (2005).
Conley, S. J., et al.,"Antiangiogenic agents increase breast cancer stem cells via the generation of tumor hypoxia," PNAS USA, vol. 109(8): 2784-2789 (2012).
Cotton, et al., "Reactivity of Cytosine and Thymine in Single-Base-Pair Mismathces With Hydroxylamine and Osmium Tetroxide and Its Application to the Study of mutations," PNAS, vol. 85(12):4397-4401 (1988).
Coussens et al., "MMP-9 supplied by bone marrow-derived cells contributes to skin carcinogenesis," Cell, vol. 103(3):481-490 (2000).
Coussens, L.M., et al., "Inflammation and cancer," Nature, vol. 420: 860-867 (2002).
Cox, et al., "A Novel Mechanism for Regulating Activity of a Transcription Factor That Controls the Unfolded Protein Response," Cell, vol. 87: 391-404 (1996).
Creighton CJ, "Residual breast cancers after conventional therapy display mesenchymal as well as tumor-initiating features," PNAS, USA, vol. 106(33):13820-13825 (2009).
Cristiano, et al., "Hepatic Gene Therapy: Adenovirus Enhancement of Receptor-Mediated Gene Delivery and Expression in Primary Hepatocytes," PNAS, USA, vol. 90(6): 2122-2126 (1993).

(56) References Cited

OTHER PUBLICATIONS

Cubillos-Ruiz, J.R, et al. "Polyethylenimine-based siRNA nanocomplexes reprogram tumor-associated dendritic cells via TLR5 to elicit therapeutic antitumor immunity," J Clin Invest, vol. 119: 2231-2244 (2009).
Cubillos-Ruiz, J.R., et al., "Blocking ovarian cancer progression by targeting tumor microenvironmental leukocytes," Cell Cycle, vol. 9: 260-268 (2010).
Cubillos-Ruiz, J.R., et al., "Reprogramming tumor-associated dendritic cells in vivo using microRNA mimetics triggers protective immunity against ovarian cancer," Cancer Res (Published OnlineFirst Feb. 3). (2012).
Cull, et al., "Screening for Receptor Ligands Using Large Libraries of Pep tides Linked to the C Terminus of the lac Repressor" PNAS USA, vol. 89: 1865-1869 (1992).
Cullen, et al., "Secreted Placental Alkaline Phosphatase as a Eukaryotic Reporter Gene," Methods in Enzymol. vol. 216: 362-368 (1992).
Curiel, et al., "Adenovirus Enhancement of Transferrin-Polylysine-Mediated Gene Delivery," PNAS, USA, vol. 88: 8850-8854 (1991).
Cwirla, et al., "Peptides on Phage: A Vast Library of Pep tides for Identifying Ligands," PNAS, USA, vol. 87: 6378-6382 (1990).
Dai, et al., "Gene Therapy Via Primary Myoblasts: Long-Term Expression of Factor IX Protein Following Transplantation In Vivo," PNAS, USA, vol. 89: 10892-10895 (1992).
Danos, et al., "Safe and Efficient Generation of Recombinant Retroviruses With Amphotropic and Ecotropic Host Ranges" PNAS, USA., vol. 85: 6460-6464 (1988).
De Palma, M., et al., "Tie 2-expressing monocytes: regulation of tumor angiogenesis and therapeutic implications," Trends Immunol., vol. 28:519-524 (2007).
De Paula, D. et al., "Hydrophobization and bioconjugation for enhanced siRNA delivery and targeting," RNA, vol. 13:431-456 (2007).
De Raedt, T. et al., "Exploiting cancer cell vulnerabilities to develop a combination therapy for Ras-driven tumors," Cancer Cell, vol. 20: 400-413 (2011).
Devlin, et al., "Random Peptide Libraries: A Source of Specific Protein Binding Molecules" Science, vol. 249: 404-406 (1990).
DeWet, et al., "Firefly Luciferase Gene: Structure and Expression in Mammalian Cells" Mol. Cell. Biol., vol. 7: 725-737 (1987).
DeWitt, et al., "Diversomers': An Approach to Nonpeptide, Nonoligometric Chemical Diversity" PNAS, USA, vol. 90: 6909-6913 (1993).
Ding L et al., "Ligand-independent activation of estrogen receptor alpha by XBP-1," Nucleic Acids Res., vol. 31(18):5266-5274. (2003).
Dinulescu, D.M., et al., "Role of K-ras and Pten in the development of mouse models of endometriosis and endometrioid ovarian cancer," Nat Med., vol. 11: 63-70 (2005).
Dontu, G et al., "In vitro propagation and transcriptional profiling of human mammary stem/progenitor cells," Genes Dev., vol. 17(10): 1253-1270 (2003).
Duan, L. et al., "Potent Inhibition of Human Immunodeficiency Virus Type 1 Replication by an Intracellular anti-REV single chain antibody," PNAS, vol. 91: 5075-5079 (1994).
Dudley, M.E., et al., "Cancer regression and autoimmunity in patients after clonal repopulation with antitumor lymphocytes," Science, vol. 298: 850-854 (2002).
Ebrahimpour, P. et al., "Metabolic Syndrome and Related Insulin Levels in Obese Children," Metab. Syndr. Relat. Disord., vol. 4(3):172-178 (2006).
Eggerding, et al., "A One-Step Coupled Amplification and Oligo-nucleotide Ligation Procedure for Multiplex Genetic Typing" PCR Methods Appl., vol. 4: 337 (1995).
Engebrecht, et al., "Identification of Genes and Gene Products Necessary for Bacterial Bioluminescence," PNAS, vol. 1: 4154-4158 (1984).
Engelke, et al., "Direct Sequencing of Enzymatically Amplified Human Genomic DNA," PNAS, USA, vol. 85: 544-548 (1988).
Eppstein, D.A. et al., "Biological activity of liposome-encapsulated murine interferon gamma is mediated by a cell membrane receptor," PNAS, vol. 82 (11):3688-3692 (1985).
Erb, et al., "Recursive Deconvolution of Combinatorial Chemical Libraries" PNAS, USA, vol. 91: 11422 (1994).
European Communication, EP Application No. 03749316.0, dated Jul. 10, 2009, 5 pages.
European Office Action, EP Application No. 05013817.1-2401, dated May 3, 2010, 6 pages.
European Search Report, EP Application No. 05013817.1-2401, dated Mar. 17, 2006, 6 pages.
Felici, et al., "Selection of Antibody Ligands From a Large Library of Oligopeptides Expressed on a Multivalent Exposition Vector" J. Mol. Biol., vol. 222: 301-310 (1991).
Ferry, et al., "Retroviral-Mediated Gene Transfer Into Hepatocytes In Vivo," PNAS, USA, vol. 88: 8377-8381 (1991).
Fischer, et al., "Partial Restoration of Defective Chloride Conductance in IIF508 CF Mice by Trimethylamine Oxide," Am. J. Physiol. Lung Cell Mol., vol. 281: L52-L57 (2001).
Ahn, J. et al., "Dietary resveratrol alters lipid metabolism-related gene expression of mice on an atherogenic diet," J. Hepatology, vol. 49 (6):1019-1028 (2008).
Ahonen, et al., "The CD40-TRAF6 Axis Controls Affinity Maturation and the Generation of Long-Lived Plasma Cells" Nat Immunol. 3(5): 451-456 (2002).
Al-Hajj, M., et al., "Prospective identification of tumorigenic breast cancer cells," PNAS, USA, vol. 100: 3983-3988 (2003).
Chen, et al., "Combined Intra-nd Extracellular Immunization Against Human Immunodeficiency Virus Type 1 Infection With a Human Anti-gp 120 Antibody," PNAS, USA, vol. 91: 5932-5936 (1994).
Altmeyer, et al., "Reversal of EBV Immortalization Precedes Apoptosis in IL-6-Induced Human B Cell Terminal Differentiation," Immunity, vol. 7: 667-677 (1997).
Andersson, L. et al., "Pharmacology of apolipoprotein A-I," Current Opinion in Lipidology, vol. 8:225-228 (1997).
Araki, E. et al., "Endoplasmic reticulum stress and diabetes mellitus," Internal Medicine, vol. 42(1):7-14 (2003).
Aridor M., "Traffic jam: a compendium of human diseases that affect intracellular transport processes," Traffic, vol. 1(11):836-851 (2000).
Aridor M., "Traffic jams II: an update of diseases of intracellular transport," Traffic, vol. 3(11):781-790 (2002).
Armentano, et al., "Expression of Human Factor IX in Rabbit Hepatocytes by Retrovirus-Mediated Gene Transfer: Potential for Gene Therapy of Hemophilia B" Proc. Natl. Acad. Sci. USA, vol. 87: 6141-6145 (1990).
Bancroft, A.J. et al. "Cytokine Production in BALB/c Mice Immunized with Radiation Attenuated Third Stage Larvae of the Filarial Nematode, Brugia pahangi," J. Immunol., vol. 150(4), pp. 1395-1402 (1993).
Bantignies, et al. "Genetic characterization of transactivation of the human T-cell leukemia virus type 1 promoter: Binding of Tax to Tax-responsive element 1 is mediated by the cyclic AMP responsive members of the CREB/ATF family of transcription factors," Mol Cell Biol., vol. 16(5), pp. 2174-2182 (1996).
Barbas, et al. "Assembly of Combinatorial Antibody Libraries on Phage Surfaces: The Gene III Site," PNAS, vol. 88: 7978-7982 (1991).
Bazter, MA, et al., "Enhanced evolutionary PCR using oligonucleotides with inosine at the 3'-terminus," Nucleic Acid Res., vol. 19(18):5081 (1991).
Beerli, et al., "Intracellular Expression of Single Chain Antibodies Reverts ErbB-2 Transformation" J. Biol. Chem., vol. 269: 23931-23936 (1994).
Bernardi, et al., "Mitochondria and Cell Death" Eur. Biochem. vol. 264: 687 (1998).
Bhowmick, N.A., et al., "Stromal fibroblasts in cancer initiation and progression," Nature, vol. 432: 332-337 (2004).
Biocca, et al., "Expression and Targeting of Intracellular Antibodies in Mammalian Cells," EMBO J. vol. 9: 101-108 (1990).

(56) References Cited

OTHER PUBLICATIONS

Boder, et al., "Directed evolution of antibody fragments with monovalent femtomolar antigen-binding affinity," PNAS, USA., vol. 97(20):10701-10705 (2000).
Boeglin et al., "Soluble CD40L and TLR Agonist synergize Murine B Cell Proliferation," Eur. J. Immunol., vol. 39(Suppl. 1), Monday Poster Sessions S55-S279. PB11/62: S163 (2009).
Bollard, C.M., et al. "Complete responses of relapsed lymphoma following genetic modification of tumor-antigen presenting cells and T-lymphocyte transfer," Blood, vol. 110: 2838-2845 (2007).
Bos, R. et al., "Levels of hypoxia-inducible factor-1alpha independently predict prognosis in patients with lymph node negative breast carcinoma," Cancer, vol. 97 (6):1573-1581 (2003).
Bradley, "Modifying the Mammalian Genome by Gene targeting," Current Opinion in Biotechnology, vol. 2: 823-829 (991).
Bradner, JE et al., "A robust small-molecule microarray platform for screening cell lysates," Chem Biol., vol. 13(5):493-504 (2006).
Breitling, R et al., "Rank products: a simple, yet powerful, new method to detect differentially regulated genes in replicated microarray experiments," FEBS Lett., vol. 573(1-3):83-92 (2004).
Brinster, et al., "Regulation of Metallothionein-Thymidine Kinase Fusion Plasmids Injected in Mouse Eggs," Nature, vol. 296: 39-42 (1982).
Brown, et al., "Protein antigens of normal and malignant human cells identified by immunoprecipitation with monoclonal antibodies," J Biol Chem., vol. 255(11):4980-4983(1980).
Bunin, et al., "A General and Expedient Method for the Solid-Phase Synthesis of 1,4-Benzodiazepine Derivatives," J. Am. Chem. Soc. 114: 109997-10998 (1992).
Burg, et al., "Effects of Glycine Betaine and Glycerophosphocholine on Thermal Stability of Ribonuclease," Am. J. Physiol. Renal Physiol., vol. 43: F762-F765 (1998).
Bushman, et al., "RNA Interference: Applications in Vertebrates," Mol Ther., vol. 7(1):9-10 (2003).
Byrne, et al., "Multiplex Gene Regulation: A Two-Tiered Approach to Transgene Regulation in Transgenic Mice," PNAS. USA, vol. 86: 5473-5477 (1989).
Calame, "Plasma Cells: Finding New Light at the End of B Cell Development," Nat. Immunol., vol. 2(12): 1103-1108 (2001).
Calame, et al., "Transcriptional Controlling Elements in the Immunoglobulin and T Cell Receptor Loci," Adv. Immunol., vol. 43: 235-275 (1988).
Calfon, M. et al., "IRE1 couples endoplasmic reticulum load to secretory capacity by processing the XBP-1 mRNA," Nature, vol. 415:92-96 (2002).
Callahan, M.J., et al., "Increased HLA-DMB expression in the tumor epithelium is associated with increased CTL infiltration and improved prognosis in advanced-stage serous ovarian cancer," Clin Cancer Res., vol. 14: 7667-7673 (2008).
Campanero, M. et al., "Regulation of E2F through ubiquitin-proteasome-dependent degradation: Stabilization by the pRB tumor suppressor protein," PNAS, USA, vol. 94:2221-2226 (1997).
Camper, et al., "Postnatal Repression of the a-Fetoprotein Gene is Enhancer Independent," Genes Dev., vol. 3: 537-546 (1989).
Cane, et al., "Harnessing the Biosynthetic Code: Combinations, Permutations, and Mutations" Science, vol. 282: 63, (1998).
Cao, W., et al. "Oxidized lipids block antigen cross-presentation by dendritic cells in cancer," J Immunol., vol. 192: 2920-2931(2014).
Carell, et al., "A Novel Procedure for the Synthesis of Libraries Containing Small Organic Molecules" Angew. Chem. Int. Ed. Engl., vol. 33: 2059 (1994).
Carell, et al., "A Solution-Phase Screening Procedure for the Isolation of Active CompoundsFrom a Library of Molecules" Angew. Chem. Int. Ed. Engl., vol. 33: 2061 (1994).
Carlson, et al., "A New Means of Inducibly Inactivating a Cellular Protein" Mol. Cell. Biol., vol. 8: 2638-2646 (1988).
Carlson, et al., "A New Use for Intracellular Antibody Expression: Inactivation of Human Immunodeficiency Virus Type I," PNAS, USA, vol. 90: 7427-7428 (1993).

Carrasco, D.R., et al., "The differentiation and stress response factor XBP-1 drives multiple myeloma pathogenesis," Cancer Cell, vol. 11: 349-360 (2007).
Caton, M.L., et al., "Notch-RBP-J signaling controls the homeostasis of CD8-dendritic cells in the spleen," J Exp Med., vol. 204: 1653-1664 (2007).
Chapman, et al., "Translational Attenuation Mediated by an mRNA Intron," Curr Biol., vol. 7:85-89 (1997).
Cheang, MC, "Basal-like breast cancer defined by five biomarkers has superior prognostic value than triple-negative phenotype," Clin Cancer Res., vol. 14(5):1368-1376 (2008).
Chen, B.P. et al. "Analysis of ATF3, a transcription factor induced by physiological stresses and modulated by gadd153/Chop10," Mol. Cell Biol., vol. 16:1157-1168 (1996).
Chen, C. et al. "In Vitro Induction of T Cell Anergy by Blocking B7 and Early T Cell Costimulatory Molecule ETC-1/B7-2" Immunity, vol. 1:147-154 (1994).
Marasco, W.A., et al., "Design, intracellular expression, and activity of a human anti-human immunodeficiency virus type 1 gp120 single-chain antibody," PNAS USA, vol. 90(16):7889-7893 (1993).
Marotta, L. L., et al., "The JAK2/STAT3 signaling pathway is required for growth of CD44?CD24? stem cell-like breast cancer cells in human tumors," J Clin Invest., vol. 121(7):2723-2735 (2011).
Matsui, et al., "B cell response pathways regulated by IL-5 and IL-2. Secretory microH chain-mRNA and J chain mRNA expression are separately controlled events" J Immunol., vol. 142(8):2918-2923 (1989).
Maxam, et al., "A new method for sequencing DNA" PNAS, vol. 74: 560-564 (1977).
Mayo, et al., "The Mouse Metallothionein-I Gene is Transcriptionally Regulated by Cadmium Following Transfection Into Human or Mouse Cells" Cell, vol. 29: 99-108 (1982).
McCafferty, et al., "Phage Antibodies: Filamentous Phage Displaying Antibody Variable Domains" Nature, vol. 348: 552-554 (1990).
McConnell, et al., "The Cytosensor Microphysiometer: Biological Applications of Silicon Technology," Science, vol. 257: 1906-1912 (1992).
McHeyzer-Williams, et al., "B Cell Memory and the Long-Lived Plasma Cell," Curr Opin ImmunolII: 172-179 (1999).
McLaughlin, et al., "Adeno-Associated Virus General Transduction Vectors: Analysis of Proviral Structures" J. Virol, vol. 62: 1963-1973 (1989).
McLean, C.Y. et al., "GREAT improves functional interpretation of cis-regulatory regions," Nat Biotechnol., vol. 28 (5):495-501 (2010).
McManus, et al., "Gene Silencing in Mammals by Small Interfering RNAs" Nat. Rev. Genet., vol. 3: 737-747 (2002).
Medzhitov R., "Recognition of microorganisms and activation of the immune response," Nature, vol. 449(7164):819-826 (2007).
Meng, et al., "Automated Docking With Grid-Based Energy Evaluation" J. Computer Chem., vol. 13: 505 (1992).
Meng, et al., "Orientational Sampling and Rigid-Body Minimization on Molecular Docking" Proteins, vol. 17: 266 (1993).
Mercola, et al., "Antisense Approaches to Cancer Gene Therapy" Cancer Gene Ther., vol. 2: 47-59 (1995).
Meredith, M.M., et al., "Expression of the zinc finger transcription factor zDC (Zbtb46, Btbd4) defines the classical dendritic cell lineage," J Exp Med., vol. 209: 1153-1165 (2012).
Mhashilkar, et al., "Inhibition of HI V-I Tat-Mediated LTR Transactivation and HIV-I Infection by Anti-Tat Single Chain Intrabodies," EMBO J., vol. 14: 1542-1551 (1995).
Mihara, et al., "Interleukin-6 (IL-6) Induces the Proliferation of Synovial Fibroblastic Cellsln the Presence of Soluble IL-6 Receptor." Brit. J Rheumatol., vol. 34: 321-325 (1995).
Miller, et al., "Progress Toward Human Gene Therapy" Blood, vol. 76(2): 271-278 (1990).
Miura, et al., "Transjent Transfection Assay of Cell Death Genes," Methods in Enzymol., vol. 322: 480-92 (2000).
Miyasaka, et al., "Constitutive Production of Interleukin 61B Cell Stimulatory Factor-2 From Inflammatory Synovium," Clin. Immunol. and Immunopathol., vol. 52: 238-247(1989).

(56) References Cited

OTHER PUBLICATIONS

Montagner,M., et al., "SHARP1 suppresses breast cancer metastasis by promoting degradation of hypoxia-inducible factors," Nature, vol. 487(7407): 380-384 (2012).
Morgan, R.A., et al., "Cancer regression in patients after transfer of genetically engineered lymphocytes," Science, vol. 314: 126-129 (2006).
Mori, et al., "A Transmembrane Protein With a cdc2+/CDC28-Related Kinase Activity is Required for Signaling From the ER to the Nucleus," Cell, vol. 74: 743-756, (1993).
Morse, et al., "Induction of Cell Cycle Arrest and B Cell Terminal Differentiation by CDK Inhibitor p18 INK4c and 11-6," Immunity, vol. 6: 47-56 (1997).
Muzyczka, et al., "Use of Adeno-Associated Virus as a General Transduction Vector for Mammalian Cells" Curro Topics in Micro. and Immunol., vol. 158: 97-129 (1992).
Myers, et al., "Detection of Single Base Substitutions by Ribonuclease Cleavage at Mismatches in RNA: DNA Duplexes" Science, vol. 230: 1242 (1985).
Myers, et al., "Detection of Single Base Substitutions in Total Genomic DNA" Nature, vol. 313: 495 (1985).
Nakatani et al., "Involvement of endoplasmic reticulum stress in insulin resistance and diabetes," Journal of Biological Chemistry, vol. 280(1): 847-851 (2005).
Nakazawa, et al., "UV and Skin Cancer: Specific p53 Gene Mutation in Normal-Skin as a Biologically Relevant Exposure Measurement" PNAS, vol. 91: 360-364 (1994).
Nelms, et al., "The IL-4 Receptor: Signaling Mechanisms and Biologic Functions" Annu. Rev. Immunol., vol. 17: 701-738 (1999).
Nesbeth, Y., et al., "CCL5-mediated endogenous antitumor immunity elicited by adoptively transferred lymphocytes and dendritic cell depletion," Cancer Res., vol. 6: 6331-6338 (2009).
Nesbeth, Y.C., et al., "CD4+ T cells elicit host immune responses to MHC class II-negative ovarian cancer through CCL5 secretion and CD40-mediated licensing of dendritic cells," J Immunol., vol. 184:5654-5662 (2010).
Neve, R.M., "A collection of breast cancer cell lines for the study of functionally distinct cancer subtypes," Cancer Cell., vol. 10(6):515-527 (2006).
Newmann, et al., "Primatization of recombinant antibodies for immunotherapy of human diseases: a macaque/human chimeric antibody against human CD4," Biotechnology, vol. 10:1455-1460 (1992).
Nickerson, et al., "Automated DNA diagnostics using an ELISA-based oligonucleotide ligation assay," PNAS, USA, vol. 87(22):8923-8927 (1990).
Nikiforov, et al., "Genetic Bit Analysis: a solid phase method for typing single nucleotide polymorphisms," Nucleic Acids Rev., vol. 22(20): 4167-4175 (1994).
Nikiforov, et al., "The use of 96-well polystyrene plates for DNA hybridization-based assays: an evaluation of different approaches to oligonucleotide immobilization" Anal Biochem, vol. 227: 201 (1995).
Nikiforov, et al., "The use of phosphorothioate primers and exonuclease hydrolysis for the preparation of single-stranded PCR products and their detection by solid-phase hybridization," PCR Methods Appl., vol. 3: 285-291 (1994).
Ohtsuka et al., "An alternative approach to deoxyoligonucleotides as hybridization probes by insertion of deoxyinosine at ambiguous codon positions," Biol Chem., vol. 260:2605-2608 (1985).
Ono, et al., "Human X-Box-Binding Protein 1 is Required for the Transcription of a Subset of Human Class II Major Histocompatibility Genes and Forms a heterodimer With c-fos," PNAS, USA, vol. 88: 4309-4312 (1991).
Orita, et al., "Detection of Polymorphisms of Human DNA by Gel Electrophoresis as Single-Strand Conformation Polymorphisms," PNAS, USA, vol. 86(8): 2766-3770 (1989).
Ozcan et al., "Chemical Chaperones Reduce ER Stress and Restore Glucose Homeostasis in a Mouse Model of Type 2 Diabetes," Science, vol. 313:1137-1140 (2006).

Ozcan et al., "Endoplasmic Reticulum Stress Links Obesity, Insulin Action, and Type 2 Diabetes," Science, vol. 306: 457-461 (2004).
Pang et al., "Addressing insulin resistance in Type I diabetes," Diabetic Medicine, vol. 25: 1015-1024 (2008).
Papandreou, I., et al., "Identification of an Ire1 alpha endonuclease specific inhibitor with cytotoxic activity against human multiple myeloma," Blood, vol. 117:1311-1314 (2011).
Partial European Search Report for Application No. 05013817.1, dated Mar. 6, 2006, 6 pages.
Patil, et al., "Intracellular Signaling From the Endoplasmic Reticulum to the Nucleus: The Unfolded Protein Response in Yeast and Mammals," Curr Opin Cell Biol., vol. 13: 349-355 (2001).
Patrick, L. "Nonalcoholic Fatty Liver Disease: Relationship to Insulin Sensitivity and Oxidative Stress. Treatment Approaches using Vitamin E, MagneSium, and Betaine," Alternative Medicine Review, Thorne Research, Inc., Sandpoint, US, vol. 7(4): 276-291 (Jan. 1, 2002).
Perou CM, "Molecular portraits of human breast tumors," Nature, vol. 406(6797):747-752 (2000).
Mantovani et al., "Neutrophils in the activation and regulation of innate and adaptive immunity," Nature Reviews Immunol., vol. 11: 519-531 (2011).
Kishimoto, et al., "RTF: A B-ZIP Transcription Factor That is Closely Related to the Human XBP/TREB5 and is Activated by Hepatocellular Carcinoma in Rats," Biochem. Biophys. Res. Commun, vol. 223: 746-751 (1996).
Kishimoto, et al., "The Biology of Interleukin-6," Blood, vol. 74(1): 1-10 (1989).
Klisch, T. J., et al., "In vivo Atoh1 targetome reveals how a proneural transcription factor regulates cerebellar development," PNAS, vol. 108, 3288-2393 (2011).
Klock, et al., "Oestrogen and Glucocorticoid Responsive Elements are Closely Related But Distinct," Nature, vol. 329: 734-736 (1987).
Kohler, et al., "Continuous Cultures of Fused Cells Secreting Antibody of Predefined Specificity," Nature, vol. 256: 495-497 (1975).
Koong, Albert C., "Focussed Review: Targeting XBP-1 as a novel anti-cancer strategy", Cancer Biology & Therapy, vol. 5 (7):756-759 (2006).
Kopf, et al., "Immune Responses of IL-4, IL-5, IL-6 Deficient Mice," Immunol Rev., vol. 148: 45-69 (1995).
Kopf, et al., "Impaired Immune and Acute-phase Responses in Interleukin-6-Deficient Mice," Nature, vol. 368: 339-342 (1994).
Kovalchuk, et al., "IL-6 Transgenic Mouse Model for Extraosseous Plasmacytoma," PNAS, USA, vol. 99(3): 1509-1514 (2002).
Kozutsumi, et al., "The Presence of Malfolded Proteins in the Endoplasmic Reticulum Signals the Induction of Glucose-Regulated Proteins," Nature, vol. 332: 462-464(1988).
Kuznetsov, et al., "Multiple Molecular Chaperones Complex With Misfolded Large Oligomeric Glycoproteins in the Endoplasmic Reticulum," J. Biol. Chem., vol. 272: 3057 (1997).
Lam, et al., "A New Type of Synthetic Peptide Library for Identifying Ligand-Binding Activity," Nature, vol. 354: 82-84 (1991).
Lam, et al., "Application of Combinatorial Library Methods in Cancer Research and Drug Discovery," Anticancer Drug Des., vol. 12: 145 (1997).
Landegran, et al., "A Ligase-Mediated Gene Detection Technique" Science, vol. 241: 1077-1080 (1988).
Langmead, B., et al., "Ultrafast and memory-efficient alignment of short DNA sequences to the human genome," Genome Biology, vol. 10, R25. (2009).
Lawrence, et al., "Clix: A Search Algorithm for Finding Novel Ligands Capable of Binding Proteins of Known Three-Dimensional Structure" Proteins, vol. 12: 31 (1992).
Lee et al., "XBP-1 regulates a subset of endoplasmic reticulum resident chaperone genes in the unfolded protein response," Mol Cell Biol., vol. 23(21):7448-7459 (2003).
Lee, A.H., et al. "Tumour necrosis factor-a and interferon-y synergistically activate the RANTES promoter through nuclear factor kB and interferon regulatory factor 1 (IRF-1) transcription factors," Biochem J., vol. 350 Pt 1: 131-138 (2000).
Lee, D.H. et al., "Proteasome inhibitors: valuable new tools for cell biologists," Trends Cell Biol., vol. 8(10): 397-403 (1998).

(56) References Cited

OTHER PUBLICATIONS

Lee, et al., "Glucocorticoids regulate expression of dihydrofolate reductase cDNA in mouse mammary tumour virus chimaeric plasmids," Nature, vol. 294: 228-232 (1981).
Lee, et al., "IRE I-Mediated Unconventional mRNA Splicing and S2P-Mediated ATF6 Cleavage Merge to Regulate XBPI in Signaling the Unfolded Protein Response," Genes Dev: vol. 16(4): 452-466 (2002).
Lee et al., "The Glucose-Regulated Proteins: Stress Induction and Clinical Applications," Trends Biochem. Sci., vol. 26:504-510 (2001).
Lee, K P., et al., "Structure of the dual enzyme Ire1 reveals the basis for catalysis and regulation in nonconventional RNA splicing," Cell, vol. 132(1):89-100 (2008).
Lehmann B. D., "Identification of human triple-negative breast cancer subtypes and preclinical models for selection of targeted therapies," J. Clinical Invest., vol. 121(7): 2750-2767 (2011).
Mantovani, A., et al. "Cancer-related inflammation," Nature, vol. 454, 436-444 (2008).
Lemarchand, et al., "Adenovirus-Mediated Transfer of a Recombinant Human UI Antitrypsin cDNA to Human Endothelial Cells," PNAS, USA, vol. 89: 6482-6486 (1992).
Lemasters, et al., "Mitochondrial permeability transition: a common pathway to necrosis and apoptosis" Biochem. Biophys. Res Commin., vol. 304(3):463-470 (2003).
Lembo, A. et al., "Administration of a synthetic TLR4 agonist protects mice from pneumonic tularemia," The Journal of Immulol., vol. 180(11):7574-7581 (2008).
Leonard, et al, "Role of the Common Cytokine Receptor y Chain in Cytokine Signaling and Lymphoid Development" Immun. Reviews, vol. 14: 8 pages (21995).
Lerner, "How to Make a Hybridoma" Yale J Biol. Med., vol. 54(5): 387-402 (1981).
Leung-Hagesteinjn, C. et al., "Xbp1s-negative tumor B cells and pre-plasmablasts mediate therapeutic proteasome inhibitor resistance in multiple myeloma," Cancer Cell., vol. 24(3):289-304 (2013).
Li X., "Intrinsic resistance of tumorigenic breast cancer cells to chemotherapy," J. Natl Cancer Inst., vol. 100(9): 672-679 (2008).
Li, B., et al., "RSEM: accurate transcript quantification from RNA-seq data with or without a reference genome," BMC Bioinformatics, vol. 12: 323. (2011).
Li, et at, "Targeted Mutation of the DNA Methyltransferase Gene Results in Embryonic Lethality" Cell, vol. 69: 915, (1992).
Li, Z., et al., "Hypoxia-inducible factors regulate tumorigenic capacity of glioma stem cells," Cancer Cell, vol. 15(6):501-513 (2009).
Lin, et al., "Repression of C-MYC Transcription by Blimp-I, An Inducer of Terminal B Cell Differentiation" Science, vol. 276: 596-599(1997).
Ling, SC et al., "Response of myeloma to the proteasome inhibitor bortezomib is correlated with the unfolded protein response regulator XBP-1," Haematologica. vol. 97(1):64-72 (2012).
Litvak, V., et al. "Function of C/EBP delta in a regulatory circuit that discriminates between transient and persistent TLR4-induced signals," Nat Immunol., vol. 10:437-443 (2009).
Litvak, V., et al. Role of the Transcript factor of C/EBPdelta in a regulatory circuit that discriminates between transient and persistent TLR4-induced signals. Nat Immunol., vol. 10:437-443 (2009).
Liu X.S., "An algorithm for finding protein-DNA binding sites with applications to chromatin-immunoprecipitation microarray experiments," Nat Biotechnol., vol. 20(8): 835-839 (2002).
Locksley, R.M. et al. "Helper T-cell subsets in mouse leishmaniasis: induction, expansion and effector function" Immunoparasitiology Today, vol. 1:A58-A61 (1991).
Lorenzo, et al., "Cytofluorometric Quantitation of Nuclear Apoptosis Induced in a Cell-Free System," Methods in Enzymol., vol. 322: 198-201 (2000).
Lupien, M., et al.,"FoxA1 translates epigenetic signatures into enhancer-driven lineage-specific transcription," Cell, vol. 132(6):958-970 (2008).
Ma, Y. et al., "The role of the unfolded protein response in tumor development: friend or foe?," Nat Rev Cancer, vol. 4: 966-977 (2004).
Madura, et al., "N-recognin/Ubc2 interactions in the N-end rule pathway," J. Biol. Chem., vol. 268(16): 12046-12054 (1993).
Maher, et al., "DNA Triple-Helix-Formation: An Approach to Artificial Gene Repressors?" Bioassays, vol. 14(12): 807-815 (1992).
Manning, et al., "Targeting JNK for Therapeutic Benefit: From Junk to Gold?" Nature Reviews, vol. 2: 554-565 (2003).
Hawkins, et al., "Selection of Phage Antibodies by Binding Affinity Mimicking Affinity Matruation" J Mol Biol. 226: 389-896 (1992).
Haze, et al., "Identification of the G13 (cAMP-Response-Element-Binding Protein-Related protein Gene Product Related to Activating Transcription Factor 6 as a Transcriptional Activator of the Mammalian Unfolded Protein Response," Biochem J., vol. 355: 19-28 (2001).
Inouye, et al., "Potent Inhibition of Human Immunodeficiency Virus Type 1 in Primary T Cells and Alveolar Macrophage by a Combination Anti-Rev Strategy Delivered in an Adeno-Associated Virus Vector," Journal of Virology, vol. 71 (5):4071-4078 (1997).
Kauffman, et al., "Stress Signaling From the Lumen of the Endoplasmic Reticulum: Coordination of Gene Transcriptional and Translational Controls." Genes Dev., vol. 13: 1211-1233 (1999).
Leonard, et al, "Role of Jak Kinases and STAT's in Cytokine Signal Transduction," Int. J Hematol., vol. 73: 271 (2001).
Matsuzaki, et al. "Identification of transcriptional activation domain of TREB5, a CTEC/ATF family I protein that Binds to HTLV-1 enhancer." J Biochem (Tokyo), vol. 117(2):303-8 (1995).
Shamu, et al., "Oligomerization and Phosphorylation of the Ire 1p Kinase During Intracellular Signaling From the Endoplasmic Reticulum to the Nucleus" EMBO J 15: 3028-3039 (1996).
Sharp, et al., "RNA Interference" Genes and Development, 287: 2431-2432 (2001).
Yoshimura, K et al., "Adenovirus-mediated augmentation of cell transfection with unmodified plasmid vectors," J Biol Chem., vol. 268(4):2300-2003 (1993).
Hwu, et al., "Functional and Molecular Characterization of Tumor-Infiltrating Lymphocytes Transduced With Tumor Necrosis Factor-a cDNA for the Gene Therapy of Cancer InHumans," -J. Immunol., vol. 150: 4104-4115 (1993).
Hynes, et al., "Hormone-Responsive Expression of an Endogenous Proviral Gene of Mouse Mammary Tumor Virus After Molecular Cloning and Gene Transfer Into Cultured Cells," Proc. Natl. Acad. Sci. USA, vol. 78: 2038-2042 (1981).
Iliopoulos D., et al., "Inducible formation of breast cancer stem cells and their dynamic equilibrium with non-stem cancer cells via IL6 secretion," PNAS, USA, vol. 108(4):1397-1402 (2011).
Iliopoulos, D., et al., "Loss of miR-200 inhibition of Suz12 leads to polycomb-mediated repression required for the formation and maintenance of cancer stem cells," Mol Cell., vol. 39(5):761-772 (2010).
Iliopoulos,D., et al.,"An epigenetic switch involving NF-kappaB, Lin28, Let-7 MicroRNA, and IL6 links inflammation to cell transformation," Cell, vol. 139(4): 693-706 (2009).
Illera, et al., "Apoptosis in Splenic B Lymphocytes. Regulation by Protein Kinase C and IL-4," J. Immunol., vol. 151(6): 2965-2973 (1993).
Inoue, et al., "Sequence-Dependent Hydrolysis of RNA Using Modified Oligonucleotide Splints and RNase H," FEBS Lett., vol. 215: 327-330 (1987).
Inoue, et al., "Synthesis and Hybridization Studies on Two Complementary Non(2'-0-Methyl)Ribonucleotides," Nucleic Acids Res.,vol. 15: 6131-6148 (1987).
Inouye, et al., "Potent Inhibition of Human Immunodeficiency Virus Type 1 Replication by an Intracellular Anti-Rev Single-Chain Antibody," PNAS, USA, vol. 91: 5075-5079 (1997).
International Preliminary Report on Patentability and Written Opinion for Application No. PCT/US2013/030251, 8 pages, dated Sep. 9, 2014.

(56) References Cited

OTHER PUBLICATIONS

Kessel, et al., "Murine Developmental Control Genes" Science, vol. 249: 374-379 (1990).
International Preliminary Report on Patentability, PCT/US2003/027404, dated Apr. 21, 2006, 4 pages.
International Preliminary Report on Patentability, PCT/US2009/030976, dated Jul. 20, 2010, 6 pages.
International Preliminary Report on Patentability, PCT/US2009/048321, dated Jan. 5, 2011, 7 pages.
International Preliminary Report on Patentability, PCT/US2014/057525, dated Mar. 29, 2016, 8 pages.
International Search Report and Written Opinion, PCT/US2010/030251, dated Jun. 26, 2013, 14 pages.
International Search Report and Written Opinion, PCT/US2009/030976, dated Jul. 9, 2009, 11 pages.
International Search Report and Written Opinion, PCT/US2013/033094, dated Oct. 10, 2013, 8 pages.
International Search Report and Written Opinion, PCT/US2014/057525, dated Nov. 24, 2014, 11 pages.
International Search Report and Written Opinion, PCT/US2009/048321, dated Dec. 8, 2009, 6 pages.
Irizarry Ra et al., "Summaries of Affymetrix GeneChip probe level data," Nucleic Acids Res., vol. 31(4):e15 (2003).
Irving, et al., "Ribosome Display and Affinity Maturation: From Antibodies to Single Vdomans and Steps Towards Cancer Therapeutics," J. Immunol. Methods., vol. 248: 31-35 (2001).
Ishii, K. et al., "Host Innate Immune Receptors and Beyond: Making Sense of Microbial Infections," Cell Host & Microbe, vol. 3: 352-363 (2008).
Israel, et al., "Highly Inducible Expression From Vectors Containing Multiple ORE's in CHO Cells Overexpressing the Glucocorticoid Receptor," Nucl. Acids Res., vol. 17: 2589-2604 (1989).
Iwabuchi, et al., "Use of the Two-Hybrid System to Identify the Domain Ofp53 Involved Oligomerization" Oncogene, vol. 8: 1693-1696 (1993).
Iwakoshi, et al., "The X-box Binding Protein-I Transcription Factor is Required for Plasma Cell Differentiation and the Unfolded Protein Response," Immunological Reviews, vol. 194: 29-38 (2003).
Keith, B., et al., "Hypoxia-inducible factors, stem cells, and cancer," Cell, vol. 129:465-472 (2007).
Jackson, E.L., et al., "Analysis of lung tumor initiation and progression using conditional expression of oncogenic K-ras," Genes Dev., vol. 15: 3243-3248 (2001).
Janeway, C. et al., "Innate immune recognition," Annu Rev Immunol. , vol. 20:197-216 (2002).
Japanese Office Action, JP Application No. 2004-533014, dated Aug. 21, 2009, 9 pages.
Keen, et al., "Rapid Detection of Single Base Mismatches as Heteroduplexes on Hydrolink Gels" Trends Genet, vol. 7:(5 (1991).
Jogi, A. et al., "Hypoxia alters gene expression in human neuroblastoma cells toward an immature and neural crest-like phenotype," PNAS USA, vol. 99 (10): 7021-7026 (2002).
Kaser et al., "Transcription Factor XBP1 Regulates Paneth Cell Function and Inflammation in the Intestine," vol. 1(1) 1-2 (2007).
Jonkers, J., et al., "Synergistic tumor suppressor activity of BRCA2 and p53 in a conditional mouse model for breast cancer," Nat Genet., vol. 29: 418-425 (2001).
Kadato, K et al., "Ranking differentially expressed genes from Affymetrix gene expression data-methods with reproducibility, sensitivity, and specificity," Algorithm Mol Biol., vol. 47: 7 pages (2009).
Kaelin, W. G., Jr., et al., "Oxygen sensing by metazoans: the central role of the HIF hydroxylase pathway," Mol Cell., vol. 30 (4):393-402 (2008).
Kaser, A. et al., "001 Transcription Factor XBP1 Regulates Paneth Cell Function and Inflammation in the Intestine," Abstracts of the ECCO Congress, Innsbruck, Austria Mar. 1-3, 2007, 2 pages.
Kaser, A. et al., "Endoplasmic reticulum stress in the intestinal epithelium and inflammatory bowel disease," Seminars in Immunology, W.B. Saunders Company, PA, US—ISSM 1044-5323, vol. 21,(3):156-163 (2009).
Kauffman, et al., "Translational efficiency of polycistronic mRNAs and their utilization to express heterologous genes in mammalian cells" EMBO J. vol. 6: 187-195 (1987).
Kauffman, et al., "Detection of DNA cleavage in apoptotic cells," Methods in Enzymol., vol. 322: 3-15 (2000).
Kawahara, et al., "Endoplasmic Reticulum Stress-Induced mRNA Splicing Permits Synthesis of Transcription Factor HaC1/ERN4 That Activates the Unfolded Protein Response," Mol. Biol. Cell., vol. 8: 1845-1862 (1997).
Kawahara, et al., "Unconventional Splicing of HaC1/ERN4 mRNA Required for the Unfolded Protein Response. Sequence-Specific and Non-Sequential Cleavage of the Splice Sites," J. Biol. Chem., vol. 273: 1802-1807 (1998).
Kawano, et al., "Autocrine Generation and Requirement of BSF-2/IL-6 for Human Multiple Myelomas," Nature, vol. 332: 83-85 (1988).
Kay, et al., "Hepatic gene therapy: persistent expression of human alpha 1-antitrypsin in mice after direct gene delivery in vivo," Human Gene Therapy, vol. 3: 641-647 (1992).
Wikipedia, "Statin," retrieved online at: http://en.wikipedia.org/wiki/Statin, 8 pages (2008).
Wiseman, R. et al., "Flavonol activation defines an unanticipated ligand-binding site in the kinase-RNase domain of IRE1," Molecular Cell, vol. 38(2), pp. 291-304 (2009).
Wong, C.L et al., "Hypoxia-inducible factor 1 is a master regulator of breast cancer metastatic niche formation," Proceedings of the National Academy of Sciences, vol. 188,(39), pp. 16369-16374 (2011).
Woo, C.W., et al., "Adaptive suppression of the ATF4-CHOP branch of the unfolded protein response by toll-like receptor signalling," Nat Cell Biol. vol. 11, pp. 1473-1480 (2009).
Wootz, H. et al., "Caspase-12 cleavage and increased oxidative stress during mononeuron degeneration in transgenic mouse model of ALS," Biochemical and Biophysical Research Communications, vol. 322, pp. 281-286 (2004).
Wootz, H.et al., "XIAP decreases caspase-12 cleavage and calpain activity in spinal cord of ALS transgenic mice," Experimental Cell Research, vol. 312, pp. 1890-1898 (2006).
Wu, X., et al.,"HIV protease inhibitors induce endoplasmic reticulum stress and disrupt barrier integrity in intestinal epithelial cells," Gastroenterology, vol. 138, pp. 197-209 (2010).
Yamaguchi, et al. "Stress-associated endoplasmic reticulum protein 1 (SERP1)/Ribosomel associated membrane protein 4 (RAMP4) stabilizes membrane proteins during stress and facilitates subsequent glycosylation." J Cell Biol. vol. 147(6), pp. 1195-1204 (1999).
Yamamura, M. et al., "Local Expression of Antiinflammatory Cytokines in Cancer," The Journal of Clinical Investigation, vol. 91, pp. 1005-1010 (1993).
Yan, et al. "Control of PERK elF2a kinase activity by the endoplasmic reticulum stress-induced molecular chaperone P58IPK." PNAS USA., vol. 99(25), pp. 15920-15925 (2002).
Yanagitani, K., et al., "Cotranslational targeting of XBP1 protein to the membrane promotes cytoplasmic splicing of its own mRNA," Mol Cell, vol. 34, pp. 191-200 (2009).
Yang, et al. "Ubiquitin protein ligase activity of IAPs and their degradation in proteasomes in response to apoptotic stimuli," Science, vol. 88(5467), pp. 874-877 (2000).
Yang, L. et al., "FZD7 has a critical role in cell proliferation in triple negative breast cancer," Oncogene, vol. 30(43), pp. 4437-4446 (2011).
Yoneda, T. et al., "Activation of caspase-12, an endoplasmic reticulum (ER) resident caspase, through tumor necrosis factor receptor-associated factor 2-dependent mechanism in response to ER stress," Journal of Biological Chemistry, vol. 276(17), pp. 13935-13940 (2001).
Yoshida et al., "ATF6 Activated by Proteolysis Binds in the Presence of NF-Y (CBF) Directly to the cis-Acting Element Responsible

(56) References Cited

OTHER PUBLICATIONS for the Mammalian Unfolded Protein Response," Molecular and Cellular Biology, vol. 20(18), pp. 6755-6767 ( 2000).
Yoshida, et al., "XBPI mRNA is Induced by ATF6 and Spliced by IRE1 in Response to ER Stress to Produce a Highly Active Transcription Factor," Cell, vol. 107, pp. 881-891 (2001).
Yoshida, et al. "A time-Dependent Phase Shift in the Mammalian Unfolded Protein Response," Dev Cell, vol. 4(2), pp. 265-271 (2003).
Zhang, K., et al., "The unfolded protein response sensor IRE1alpha is required at 2 distinct steps in B cell lymphopoiesis," J Clin Invest., vol. 115, pp. 268-281 (2005).
Zhang, K.et al., "From endoplasmic-reticulum stress to the inflammatory response," Nature, vol. 454, pp. 455-462 (2008).
Zhu, et al. "Interaction of ATF6 and serum response factor," Mol Cell Biol. vol. 17(9), pp. 4957-4966 (1997).
Zollner, et al. "Proteasome inhibition reduces superantigen-mediated T cell activation and the severity of psoriasis in a SCID-hu model," J Clin Invest. vol. 109(5), pp. 671-679 (2002).
Ranger, et al. "Inhibitory function of two NFAT family members in lymphoid homeostasis and Th2 development," Immunity, vol. 9(5), pp. 627-635 (1998).
Rao, R. et al., "Misfolded proteins, endoplasmic reticulum stress and neurodegeneration," Current Opinion in Cell Biology, vol. 16, pp. 653-662 (2004).
Rapoport, M. et al., "Interleukin 4 Reverses T Cell Proliferative Unresponsiveness and Prevents the Onset of diabetes in Nonobese Diabetic Mice," J. Exp. Med., vol. 178, pp. 87-99 (1993).
Raychaudhuri, S., et al. "Identifying relationships among genomic disease regions: predicting genes at pathogenic SNP associations and rare deletions," PLoS Genet 5, e1000534, 15 pages (2009).
Reddy, J. et al., "Lipid Metabolism and Liver Inflammation II. Fatty liver disease and fatty acid oxidation," Am. J. Physiol. Gastrointest Liver Physiol., vol. 290, pp. G852-G858 (2006).
Reimold, A. et al., "Control of Terminal B Cell Differentiation by Transcription Factor XBP-1," Arthritis & Rheumatism, vol. 42(9 Suppl.):S58, Poster No. 52 (1999).
Reimold, A. et al., "Chondrodysplasia and neurological abnormalities in ATF-2-deficient mice," Nature, vol. 379, pp. 262-265 (1996).
Reimold, A. et al., "Transcription Factor B Cell Lineage-specific Activator Protein Regulates the Gene for Human X-Box Binding Protein 1," J. Exp. Med., vol. 183, pp. 393-401 (1996).
Reimold, et al. "Plasma cell differentiation requires the transcription factor XBP-1," Nature, vol. 412(6844), pp. 300-307 (2001).
Richardson, C.E., et al., "An essential role for XBP-1 in host protection against immune activation in C. elegans," Nature, vol. 463, pp. 1092-1095 (2010).
Roach, J.C., et al., "Transcription factor expression in lipopolysaccharide-activated peripheral-blood-derived mononuclear cells," PNAS USA, vol. 104, pp. 16245-16250 (2007).
Rock, et al. "Degradation of cell proteins and the generation of MHC class I-presented peptides," Annu Rev Immunol. vol. 17, pp. 739-779 (1999).
Romero-Ramirez, L. et al., "XBP1 is essential for survival under hypoxic conditions and is required for tumor growth," Cancer Research, American Association for Cancer Research, US, vol. 64(17), pp. 5943-5947 (2004).
Rong, J. et al., "BAR, an endoplasmic reticulum-associated E3 ubiquitin ligase, modulates BI-1 protein stability and function in ER stress," Journal of Biological Chemistry, vol. 286 (2), pp. 1453-1463 (2010).
Rudolph, D. et al., "Impaired fetal T cell development and perinatal lethality in mice lacking the cAMP response element binding protein," PNAS U S A., vol. 95(8), pp. 4481-4486 (1998).
Ruegsegger, et al., "Block of HAC1 mRNA Translation by Long-Range Base Pairing is Released by Cytoplasmic Splicing Upon Induction of the Unfolded Protein Response," Cell, vol. 107 p. 103 (2001).

Samuel. "The eIF-2a protein kinases, regulators of translation in eukaryotes from yeasts to humans," J Biol Chem., vol. 268(11), pp. 7603-7606 (1993).
Schmidt, C. et al., "Scatter factor/hepatocyte growth factor is essential for liver development," Nature, vol. 373, pp. 699-702 (1995).
Schroder, et al, "Control of glycosylation of MHC class II-associated invariant chain Cy transloco-associated RAMP4," EMBO J, vol. 18(17), pp. 4804-4815 (1999).
Schurr, J.R., et al., "Central role of toll-like receptor 4 signaling and host defense in experimental pneumonia caused by Gram-negative bacteria," Infect Immun., vol. 73, pp. 532-545 (2005).
Servillo, G. et al., "Transcription factor CREM coordinates the timing of hepatocyte proliferation in the regenerating liver," Genes & Development, vol. 12, pp. 3639-3643 (1998).
Sgadari, et al. "HIV protease inhibitors are potent anti-angiogenic molecules and promote regression of Kaposi sarcoma," Nat Med. vol. 8(3), pp. 225-232 (2002).
Sha, H. et al., "The IRE1?-XBP1 pathway of the unfolded protein response is required for adipogenesis," Cell Metabolism, vol. 9 (6), pp. 556-564 (2009).
Shaffer, A.L., et al., "XBP1, downstream of Blimp-1, expands the secretory apparatus and other organelles, and increases protein synthesis in plasma cell differentiation," Immunity, vol. 21, pp. 81-93 (2004).
Shapira, S.D., et al., "A physical and regulatory map of host-influenza interactions reveals pathways in H1N1 infection," Cell, vol. 139, pp. 1255-1267 (2009).
Shearer, G. et al., "T helper cell immune dysfunction in asymptomatic, HIV-1-seropositive individuals: the role of TH1-TH2 cross-regulation," Chem. Immunol., vol. 54, pp. 21-43 (1992).
Shen, et al, "Identification and Characterization of a Novel Endoplasmic Reticulum (ER) Dnaj Homologue which Stimulates ATPase Activity of BiP in vitro and is Induced by ER Stress," J. Bio Chem., vol. 277 (18), pp. 15947-15956.
Shen, et al., "Complementary Signaling Pathways Regulate the Unfolded Protein Response and are Required for C. Elegans Development," Cell, vol. 107, pp. 893 (2001).
Sigma-Aldrich, "Lipoprotein Function and Lipid Transport," retrieved online at: http://www.sigmaaldrich.com/Area.sub.-of.sub.-Interest/Biochemicals/Enzyme, 3 pages (2008).
Simon, A.K. et al., "Divergent T-cell cytokine patterns in inflammatory arthritis," Proc. Natl. Acad. Sci. USA, vol. 91, pp. 8562-8566 (1994).
Singh, M., et al., "Polylactide-co-glycolide micropartides with surface adsorbed antigens as vaccine delivery systems," Curr Drug Deliv., vol. 3, pp. 115-120 (2006).
Sriburi, R. et al., "Coordinate Regulation of Phospholipid Biosynthesis and Secretory Pathway Gene Expression in XBP-1(S)-induced Endoplasmic Reticulum Biogenesis," The Journal of Biological Chemistry, vol. 282 (10), pp. 7024-7034 (2007).
Sriburi, R. et al., "XBP1: a link between the unfolded protein response, lipid biosynthesis, and biogenesis of the endoplasmic reticulum," The Journal of Cell Biology, vol. 167(1), pp. 35-41 (2004).
Sullivan, B.M., et al., "Antigen-driven effector CD8 T cell function regulated by T-bet," Proc Natl Acad Sci USA, vol. 100, pp. 15818-15823 (2003).
Takeuchi, T. et al. "Heart Allografts in Murine Systems. The Differential Activation of TH2-Like Effector Cells in Peripheral Tolerance" Transplantation, vol. 53(6), pp. 1281-1291 (1992).
Taub, R. "Transcriptional control of liver regeneration" FASEB J., vol. 10, pp. 413-427 (1996).
Thai, N. et al., "Cytokine mRNA Profiles in Mouse Orthotopic Liver Transplantation," Transplantation, vol. 59 (2), pp. 274-281 (1995).
Todd, D., et al., "XBP1 governs late events in plasma cell differentiation and is not required for antigen specific memory B cell development," J Exp Med., vol. 206, pp. 2151-2159 (2009).
Turner, B. et al., "ER Stress and UPR in Familial Amyotrophic Lateral Sclerosis," Current Molecular Medicine, vol. 6, pp. 79-86 (2006).

(56) References Cited

OTHER PUBLICATIONS

Turner, M. et al., "HLA-B27 misfolding in transgenic rats is associated with activation of the unfolded protein response," Journal of Immunology, vol. 175, pp. 2438-2448 (2005).
Tzakis, A.G. et al. "Early Tolerance in Pediatric Liver Allograft Recipients" J. Pediatr. Surg., vol. 29(6), pp. 754-756 (1994).
Uehara, Y. et al., "Placental defect and embryonic lethality in mice lacking hepatocyte growth factor/scatter factor," Nature, vol. 373, pp. 702-705 (1995).
Urano, et al. "A survival pathway for Caenorhabditis elegans with a blocked unfolded protein response." J Cel Biol. vol. 158(4), pp. 639-646 (2002).
Urano, F., et al. "Coupling of stress in the ER to activation of JNK protein kinases by transmembrane protein kinase IRE1," Science, vol. 287, pp. 664-666 (2000).
Urushitani, M. et al., "Chromogranin-mediated secretion of mutant superoxide dismutase proteins linked to amyotrophic lateral sclerosis," Nature Neuroscience, vol. 9(1), pp. 108-118 (2006).
Van Huizen, R. et al., "P58IPK, a novel endoplasmic reticulum stress-inducible protein and potential negative regulator of eIF2alpha signaling," Journal of Biological Chemistry, vol. 278(18), pp. 15558-15564 (2003).
Vlug, A. et al., "ATF3 expression precedes death of spinal motoneurons in amyotrophic lateral sclerosis-SOD1 transgenic mice and correlates with c-Jun phosphorylation, CHOP expression, somato-dendritic ubiquitination and Golgi fragmentation," European Journal of Neuroscience, vol. 22, pp. 1881-1894 (2005).
Vranic, S et al., "Angiogenesis in triple-negative adenoid cystic carcinomas of the breast," Virchows Archiv., Springer, Berlin, DE, vol. 459 (4), pp. 377-382 (2011).
Wang, et al. "Oligomeric complexes involved in translocation of proteins across the membrane of the endoplasmic reticulum," FECS Lett., vol. 457(3), pp. 316-322 (1999).
Wikipedia, "Autophagy," retrieved online at: http://en.wikipedia.org/wiki/Autophagy, 6 pages, (2012).
GenBank Gl:4827058 for X-box binding protein 1; x-box-binding protein-1 [Homo sapiens].
Genestier et al., TLR Agonists Selectively Promote Terminal Plasma Cell Differentiation of B Cell Subsets Specialized in Thymus-Independent Responses, The Journal of Immunology, vol. 178, pp. 7779-7786 (2007).
Ghosh, R. et al., "Transcriptional regulation of VEGF-A by the unfolded protein response pathway," Plos One, vol. 5(3), pp. 1-12 (2010).
Glimcher, et al., "From Sugar to Fat: How the Transcription Factor XBP1 Regulates Hepatic Lipogenesis," Ann. N.Y. Acad. Sci., vol. 1173, pp. E2-E9 (2009).
Gorczynski, R.M. et al., "Interleukin 12 in Combination With Anti-Interleukin 10 Reverses Graft Prolongation After Portal Venous Immunization," Transplantation, vol. 60(11), pp. 1337-1341 (1995).
Grzych, J.-M. et al. "Egg Deposition is the Major Stimulus for the Production of Th2 Cytokines in Murine Schistosomiasis Mansoni," J. Immunol., vol. 146(4), pp. 1322-1327 (1991).
Gu, F. et al., "Protein-tyrosine phosphatase 1B potentiates IRE1 signaling during endoplasmic reticulum stress," Journal of Biological Chemistry, vol. 279(48), pp. 49689-49693 (2004).
Gualdi, R. et al. "Hepatic specification of the gut endoderm invitro: cell signaling and transcription control," Genes Dev. vol. 10, pp. 1670-1682 (1996).
Gunes, C. et al. "Embryonic lethality and liver degeneration in mice lackin the metal-responsive transcriptional activator MTF-1," EMBO J., vol. 17, pp. 2846-2854 (1998).
Harding, et al. "An integrated stress response regulates amino acid metabolism and resistance to oxidative stress," Mol Cell., vol. 11(3), pp. 619-633 (2003).
Harding, et al. "Regulated translation initiation controls stress-induced gene expression in mammalian cells," Mol Cell. vol. 6(5), pp. 1099-1108 (2000).
Hentsch, B. et al., "Hlx homeo box gene is essential for an inductive tissue interaction that drives expansion of embryonic liver and gut," Genes Dev., vol. 10, pp. 70-79 (1996).
Hetz, C. et al., "Fine-tuning of the unfolded protein response—Assembling the IRE1 interactome," Molecular Cell, vol. 35, pp. 551-561 (2009).
Hetz, Claudio et al., "The Unfolded Protein Response: Intergrating Stress Signals Through the Stress Sensor IRE1 alpha," Physiol Rev., vol. 91, pp. 1219-1243 (2011).
Hetz, Claudio et al., "XBP-1 and the UPRosome: Mastering Secretory Cell Function," Current Immunology Reviews, vol. 4, pp. 1-10 (2008).
Hetz, Claudio et al., "XBP-1 deficiency in the nervous system protects against amyotrophic lateral sclerosis by increasing autophagy," Genes & Development, vol. 23, pp. 2294-2306 (2009).
Hirsch, Emilio et al., "Impaired migration but not differentiation of haematopoietic stem cells in the absence of .beta.1 integrins," Nature, vol. 380, pp. 171-175 (1996).
Hollien, J., et al., "Regulated Ire1-dependent decay of messenger RNAs in mammalian cells," J Cell Biol., vol. 186, pp. 323-331 (2009).
Hosokawa, et al. "A novel ER a-mannosidase-like protein accelerates ER-associated degradation," EMBO Rep., vol. 2(5), pp. 415-422 (2001).
Hosokawa, N. et al., "EDEM accelerates ERAD by preventing aberrant dimer formation of misfolded alpha1-antitrypsin," Genes to Cells, vol. 11, pp. 465-476 (2006).
Hosseini, et al. "Protection against experimental autoimmune encephalomyelitis by a protesome modulator," J Neuroimmunol., vol. 118(2), pp. 233-244 (2001).
Hoyer-Hansen, M. et al., "Connecting endoplasmic reticulum stress to autophagy by unfolded protein response and calcium," Cell Death and Differentiation, vol. 14, pp. 1576-1582 (2007).
Hu, F. "ER stress and its regulator X-box-binding protein-1 enhance polyIC-induced innate immune response in dendritic cells," European Journal of Immunology, vol. 41(4), pp. 1086-1097(2011).
Ilieva, E. et al. "Oxidative and endoplasmic reticulum stress interplay in sporadic amyotrophic lateral sclerosis," Brain, vol. 130, pp. 3111-3123 (2007).
International Preliminary Report on Patentability, PCT/US2012/024140, dated Aug. 13, 2013, 6 pages.
International Search Report and Written Opinion, PCT/US2012/024140, dated Aug. 17, 2012, 9 pages.
Iwakoshi, et al. "Plasma cell differentiation and the unfolded protein response intersect at the transcription factor XBP-1," Nat Immunol., vol. 4(4), pp. 321-329 (2003).
Iwakoshi, et al., "The transcription factor XBP-1 is essential for the development and survival of dendritic cells," J Exp Med., vol. 204, pp. 2267-2275 (2007).
Iwawaki, T., et al., "Function of IRE1 alpha in the placenta is essential for placental development and embryonic viability," PNAS, vol. 106, pp. 16657-16662 (2009).
Jacks, T. et al. "Effects of an Rb mutation in the mouse" Nature, vol. 359, pp. 295-300 (1992).
Johnson, C.P., et al., "Forced unfolding of proteins within cells," Science, vol. 317, pp. 663-666 (2007).
Kakiuchi, et al. "Impaired feedback regulation of XBP1 as a genetic risk factor for bipolar disorder," Nat Genet. vol. 35(2), pp. 171-175 (2003).
Karin, et al. "Phosphorylation meets ubiquitination: the control of NF-[kappa]B activity," Annu Rev Immunol., vol. 18, pp. 621-663 (2000).
Kam, T. et al., "Homogeneous Datasets of Triple Negative Breast Cancers Enable the Identification of Novel Prognostic and Predictive Signatures," PLOS ONE, vol. 6(12) e28483-e28483 (2011).
Kaser, A., et al., "XBP1 links ER stress to intestinal inflammation and confers genetic risk for human inflammatory bowel disease," Cell, vol. 134, pp. 743-756 (2008).
Katze, "Regulation of the interferon-induced PKR: can viruses cope?" Trends Microbiol. vol. 3(2), pp. 75-78 (1995).
Kaufman, D.R., et al, "Route of adenovirus-based HIV-1 vaccine delivery impacts the phenotype and trafficking of vaccine-elicited CD8+ T lymphocytes," J Virol, vol. 84, pp. 5986-5996 (2010).

(56) References Cited

OTHER PUBLICATIONS

Kaufman, R.J., et al., "Inositol-requiring 1/X-box-binding protein 1 is a regulatory hub that links endoplasmic reticulum homeostasis with innate immunity and metabolism," EMBO Mol Med., vol. 2, pp. 189-192 (2010).
Kaufman, R.J., "Orchestrating the unfolded protein response in health and disease," The Journal of Clinical Investigation, vol. 110(10), pp. 389-1398 (2002).
Khoury, S.J. et al. "Oral Tolerance to Myelin Basic Protein and Natural Recovery from Experimental Autoimmune Encephalomyelitis are Associated with Downregulation of Inflammatory Cytokines and Differential Upregulation of Transforming Growth Factor.beta., Interleukin 4, and Prostaglandin E Expression in the Brain," J. Exp. Med., vol. 176, pp. 1355-1364 (1992).
Kieran, D. et al., "Deletion of the BH3-only protein puma protects motoneurons from ER stress-induced apoptosis and delays motoneuron loss in ALS mice," PNAS, vol. 20606-20611 (2007).
Kikuchi, et al. "Functional analysis of human P5, a protein disulfide isomerase homologue," J Biochem (Tokyo)., vol. 132(3), pp. 451-455 (2002).
Kikuchi, H. et al., "Spinal cord endoplasmic reticulum stress associated with a microsomal accumuilation of mutant superoxide dismutase-1 in an ALS model," PNAS, vol. 103(15), pp. 6025-6030 (2006).
Kinnebrew, M.A., et al., "Bacterial flagellin stimulates Toll-like receptor 5-dependent defense against vancomycin-resistant Enterococcus infection," J Infect Dis., vol. 201 (4), pp. 534-543 (2010).
Kishimoto, T. et al., "Enhanced Expression of a New Class of Liver-enriched b-Zip Transcription Factors, Hepatocarcinogenesis-related Transcription Factor, in Hepatocellular Carcinomas of Rats and Humans," Cell Growth & Differentiation, vol. 9, pp. 337-334 (1998).
Kisselev, et al. "Proteasome inhibitors: from research tools to drug candidates." Chem Biol., vol. 8(8), p. 739-758 (2001).
Komatsu, M. et al., "Loss of autophagy in the central nervous system causes neurodegeneration in mice," Nature, vol. 441, pp. 880-884 (2006).
Kono, H. et al., "How dying cells alert the immune system to danger," Nat Rev Immunol., vol. 8(4), pp. 279-289 (2008).
Korennykh, A.V. et al., "The unfolded protein response signals through high-order assembly of Ire1," Nature, vol. 457, pp. 687-693 (2009).
Kovacsovics-Bankowski, M. et al., "Efficient major histocompatibility complex class I presentation of exogenous antigen upon phagocytosis by macrophages," PNAS USA, vol. 90, pp. 4942-4946 (1993).
Kullberg, M.C., et al. "Infection With Schistosoma mansoni Alters Th1/Th2 Cytokine Responses to a Non-Parasite Antigen" J. Immunol., vol. 148(10), pp. 3264-3270 (1992).
Kurisu, et al., "MDG1/ERdj4, an ER-resident DnaJ family member, suppresses cell death induced by ER stress," Genes Cells, vol. 8(2), pp. 189-202 (2003).
Lee, A.-H., et al., "Regulation of Hepatic Lipogenesis by the Transcription Factor XBP1," Science, vol. 320, pp. 1492-1496 (2008).
Lee, A.-H., et al., "XBP-1 is required for biogenesis of cellular secretory machinery of exocrine glands," EMBO J., vol. 24, pp. 4368-4380 (2005).
Lee, A.-H., et al., "XBP-1 regulates a subset of endoplasmic reticulum resident chaperone genes in the unfolded protein response," Mol Cell Biol., vol. 23, pp. 7448-7459 (2003).
Lee, A.-H., et al., "Protesome inhibitors disrupt the unfolded protein response in myeloma cells," PNAS vol. 100 (17) pp. 9946-9951 (2003).
Lee, Eva Y.-H. P., et al., "Mice deficient for Rb are nonviable and show defects in neurogenesis and haematopoiesis," Nature, vol. 359, pp. 288-294 (1992).
Lee, T.G., et al. "Purification and partial characterization of a cellular inhibitor of the interferoninduced protein kinase of M, 68,000 from influenza virus-infected cells." Proc Natl Acad Sci USA, vol. 87(16), pp. 6208-6212 (1990).
Levy, Adam E. et al., "Administration of Ingraft Interleukin-4 Prolongs Cardiac Allograft Survival in Rats Treated With Donor-specific Transfusion/Cyclosponne," Transplantation, vol. 60(5), pp. 405-406 (1995).
Lindsten, et al. "A transgenic mouse model of the ubiquitin/ proteasome system," Nat Biotechnol., vol. 21(8), pp. 897-902. (2003).
Liou, H.C., et al., "A new member of the leucine zipper class of proteins that binds to the HLA DR alpha promoter," Science, vol. 247, pp. 1581-1584 (1990).
Lisbona, F., et al. "BAX inhibitor-1 is a negative regulator of the ER stress sensor IRE1alpha," Mol Cell, vol. 33(6) pp. 679-691 (2009).
Litvak, V., et al. "Function of C/EBP delta in a regulatory circuit that discriminates between transient and persistent TLR4-induced signals," Nat Immunol., vol. 10, pp. 437-443 (2009).
Liu, C.Y., et al.,"Ligand-independent dimerization activates the stress response kinases IRE1 and PERK in the lumen of the endoplasmic reticulum," J Biol Chem., vol. 275(32), pp. 24881-24885 (2000).
Liu, J., et al., "Modulation of DNA vaccine-elicited CD8+ T-lymphocyte epitope immunodominance hierarchies," J Virol., vol. 80, pp. 11991-11997 (2006).
Locksley, R.M. et al. "Helper T-cell subsets in mouse leishmaniasis: induction, expansion and effector function," Immunoparasitiology Today, vol. 1, pp. A58-A61 (1991).
Luo, D. et al., "AIP1 is critical in transducing IRE1-mediated endoplasmic reticulum stress response," Journal of Biological Chemistry, vol. 283(18), pp. 11905-11912 (2008).
Luo, H-C, et al. "Spontaneous calcification of arteries and cartilage in mice lacking matrix GLA protein." Nature. vol. 386(6620) pp. 78-81 (1997).
Luo, H., et al. "A proteasome inhibitor effectively prevents mouse heart allograft rejection," Transplantation, vol. 72(2) pp. 196-202 (2001).
Ma, Y. et al., "The unfolding tale of the unfolded protein response," Cell, vol. 107(7), pp. 827-830 (2001).
Ma, Y. et al., "Plasma cell differentiation initiates a limited ER stress response by specifically suppressing the PERK-dependent branch of the unfolded protein response," Cell Stress and Chaperones, vol. 15, pp. 281-293 (2010).
Maeda, H., et al., "Adoptive transfer of a Th2-like cell line prolongs MHC class II antigen disparate skin allograft survival in the mouse," International Immunology, vol. 6(6) pp. 855-862 (1994).
Maekawa, T., et al., "Mouse ATF-2 null mutants display features of a severe type of meconium aspiration syndrome," The Journal of Biological Chemistry, vol. 274(25), pp. 17813-17819 (1999).
Martinon, F. et al., "Regulation of innate immunity by signaling pathways emerging from the endoplasmic reticulum," Current Opinion in Immunology, vol. 23, pp. 1-6 (2010).
Martinon, F. et al., "TLR activation of the transcription factor XBP1 regulates innate immune responses in macrophages," Nat Immunol. vol. 11, pp. 411-418 (2010).
Matus, S. et al., "The Stress Rheostat: An Interplay Between the Unfolded Protein Response (UPR) and Autophagy in Neurodegeneration," Current Molecular Medicine, vol. 8, pp. 157-172 (2008).
Melville, et al. "The cellular inhibitor of the PKR protein kinase, P58,r, is an influenza virus activated co-chaperone that modulates heat shock protein activity," J Biol Chem., vol. 274(6), pp. 3797-3803 (1999).
Meng, et al. "Exponemycin exerts its antitumor effect through the inhibition of proteasome function," Cancer Res., vol. 59(12), pp. 2798-2801 (1999).
Meng, et al. "Expoxomicin, a potent and selective proteasome inhibitor, exhibits in vivo antiinflammatory activity," PNAS USA., vol. 96(18), pp. 10403-10408 (1999).
Meusser, B., et al., "ERAD: the long road to destruction," Nature Cell Biology, vol. 7(8), pp. 766-772 (2005).
Mikkelsen, T.S., et al., "Genome-wide maps of chromatin state in pluripotent and lineage-committed cells," Nature, vol. 448, pp. 553-560 (2007).

(56) References Cited

OTHER PUBLICATIONS

Molinari, et al. "Role of EDEM in the release of misfolded glycoproteins from the calnexin cycle," Science, vol. 299(5611), pp. 1397-1400 (2003).

Mucenski, M.L. et al. "A Functional c-myb Gene is Required for Normal Murine Fetal Hepatic Hematopoiesis," Cell, vol. 65, pp. 677-689 (1991).

Nagata, T. et al., "Increased ER stress during motor neuron degeneration in a transgenic mouse model of amyotrophic lateral sclerosis," Neurological Research, vol. 29, pp. 767-771 (2007).

Nau, G.J., et al., "Human macrophage activation programs induced by bacterial pathogens," PNAS, USA, vol. 99, pp. 1503-1508 (2002).

Newman, J. et al., "Comprehensive identification of Human bZIP Interactions with Coiled-Coil Arrays," Science, vol. 300, pp. 2097-2101 (2003).

Nishitoh, H., et al., "ASK1 is essential for endoplasmic reticulum stress-induced neuronal cell death triggered by expanded polyglutamine repeats," Genes and Development, vol. 16, pp. 1345-1355 (2002).

Oda, et al. "EDEM as an acceptor of terminally misfolded glycoproteins released from calnexin," Science, vol. 299(5611), pp. 1394-1397 (2003).

Ogata, M. et al., "Autophagy is Activated for Cell Survival after Endoplasmic Reticulum Stress," Molecular and Cellular Biology, vol. 26(24), pp. 9220-9231 (2006).

Ohtsuka, et al. "Mammalian HSP40/DNAJ homologs: cloning of novel cDNAs and a proposal for their classification and nomenclature," Cell Stress Chaperones, vol. 5(2), pp. 98-112 (2000).

Okada, et al, "Distinct roles of activating transcription factor 6 (ATF6) and double-stranded RNA-activated protein kinase-like endoplasmic reticulum kinase (PERK) in transcription during the mammalian unfolded protein response," Biochem J., vol. 366(Pt 2), pp. 585-594 (2002).

Ota, T. et al., "Inhibition of apolipoprotein B100 secretion by lipid-induced hepatic endoplasmic reticulum stress in rodents," The Journal of Clinical Investigation, vol. 118(1), pp. 316-332 (2008).

Parker, R. et al., "Endoplasmic Reticulum Stress Links Dyslipidemia to Inhibition of Proteasome Activity and Glucose Transport by HIV Protease Inhibitors," Molecular Pharmacology, vol. 67(6), pp. 1909-1919 (2005).

Pati, et al. "Antitumorigenic effects of HIV protease inhibitor ritonavir: inhibition of Kaposi sarcoma," Blood, vol. 15,99(10), pp. 3771-3779 (2002).

Paul, W. et al., "Lymphocyte Responses and Cytokines," Cell, vol. 76, pp. 241-251 (1994).

Pearce, E.J. et al. "Downregulation of Th1 Cytokine Production Accompanies Induction of Th2 Responses by a Parasitic Helminth, Schistosoma mansoni" J. Exp. Med., vol. 173, pp. 159-166 (1991).

Pearlman, E. et al., "Induction of Murine T-Helper-Cell Responses to the Filarial Nematode Brugia malayi," Infection and Immunity, vol. 61(3), pp. 1105-1112 (1993).

Peng, et al. "NFATc1 and NFATc2 together control both T and B cell activation and differentiation." Immunity, vol. 14(1), pp. 13-20 (2001).

Persing, D.H., et al., "Taking toll: lipid A mimetics as adjuvants and immunomodulators," Trends Microbiol., vol. 10, pp. S32-S37 (2002).

Pisa, P. et al., "Selective expression of interleukin 10, interferon y, and granulocyte-macrophage colony-stimulating factor in ovarian cancer biopsies," PNAS USA, vol. 89, pp. 7708-7712 (1992).

Abcam, "IRE1 antibody (ab45973)," retrieved online at: http://www.abcam.com/IRE1-antibody-ab45973.html, 4 pages (2011).

Abcam, "XBP1 antibody (ab37152)," retrieved online at: http://www.abcam.com/XBP1-antibody-ab37152.html, 4 pages (2011).

Acosta-Alvear, D. et al., "XBP1 controls diverse cell type- and condition specific-transcriptional regulatory networks," Molecular Cell, vol. 27, pp. 53-66. (2007).

Aghajanian, et al. "A phase I trial of the novel proteasome inhibitor PS341 in advanced solid tumor malignancies." Clin Cancer Res., vol. 8, pp. 2505-2511 (2002).

Ahem, H., "Biochemical Reagent kits offer scientists good return on investment," The Scientist, vol. 9(15), pp. 20, (1995).

Amit, I., et al., "Unbiased Reconstruction of a Mammalian Transcriptional Network Mediating Pathogen Responses," Science, vol. 326, pp. 257-263 (2009).

Atkin, J. et al., "Induction of the Unfolded Protein Response in Familial Amyotrophic Lateral Sclerosis and Association of Protein-disulfide Isomerase with Superoxide Dismutase 1," The Journal of Biological Chemistry, vol. 281(40), pp. 30152-30165 (2006).

Atkin, J. et al., "Endoplasmic reticulum stress and induction of the unfolded protein response in human sporadic amyotrophic lateral sclerosis," Neurobiology of Disease, vol. 30, pp. 400-407 (2008).

Auf G. et al., "Inositol-requiring enzyme 1 is a key regulator of angiogenesis and invasion in malignant glioma," PNAS, vol. 107(35), pp. 15553-15558 (2010).

Bagchi, A., et al., "MyD88-dependent and MyD88-independent pathways in synergy, priming, and tolerance between TLR agonists," J Immunol., vol. 178, pp. 1164-1171 (2007).

Bancroft, A.J. et al. "Cytokine Production in BALB/c Mice Immunized with Radiation Attenuated Third Stage Larvae of the Filarial Nematode, Brigia pahangi," J. Immunol., vol. 150(4), pp. 1395-1402 (1993).

Bantignies, et al. "Genetic characterization of transactivation of the human T-cell leukemia virus type 1 promoter: Binding of Tax to Tax-responsive element 1 is mediated by the cyclic AMP responsive members of the CREB/ATF family of transcription factors." Mol Cell Biol., vol. 16(5), pp. 2174-2182 (1996).

Barouch, D.H., et al., "Immunogenicity of recombinant adenovirus serotype 35 vaccine in the presence of pre-existing anti-Ad5 immunity," J Immunol., vol. 172, pp. 6290-6297 (2004).

Barski, A. et al., "High-resolution profiling of histone methylations in the human genome," Cell, vol. 129, pp. 823-837 (2007).

Beg, A.A. et al. "Embryonic lethality and liver degeneration in mice lacking the RelA component of NF-kappa.B" Nature, vol. 376, pp. 167-170 (1995).

Boldrick, J.C., et al., "Stereotyped and specific gene expression programs in human innate immune responses to bacteria," Proc Natl Acad Sci USA, vol. 99, pp. 972-977 (2002).

Brauweiler, et al. "A molecular mechanism for human T-cell leukemia virus latency and Tax transactivation." J Biol Chem., vol. 270(21), pp. 12814-12822 (1994).

Bush, et al. "Proteasome inhibition leads to a heat-shock response, induction of endoplasmic reticulum chaperones, and thermotolerance." J Biol Chem., vol. 272(141), pp. 9086-9092 (1997).

Campanero, M. et al., "Regulation of E2F through ubiquitin-proteasome-dependent degradation: Stabilization by the pRB tumor suppressor protein," Proc. Natl. Acad. Sci. USA, vol. 94, pp. 2221-2226 (1997).

Chen, B.P. et al. "Analysis of ATF3, a transcription factor induced by physiological stresses and modulated by gadd153/Chop10" Mol. Cell Biol., vol. 16, pp. 1157-1168 (1996).

Chen, C. et al. "In Vitro Induction of T Cell Anergy by Blocking B7 and Early T Cell Costimulatory Molecule ETC-1/B7-2" Immunity, vol. 1, pp. 147-154 (1994).

Chen, H. et al. "Regulation and Activities of .alpha.-Fetoprotein" Critical Reviews in Eukaryotic Gene Expression 7(1&2):11-41 (1997).

Chen, L., et al., "HIV protease inhibitor lopinavir-induced TNF-alpha and IL-6 expression is coupled to the unfolded protein response and ERK signaling pathways in macrophages," Biochem Pharmacol., vol. 78, pp. 70-77 (2009).

Chen, X., et al., "Integration of external signaling pathways with the core transcriptional network in embryonic stem cells," Cell, vol. 133, pp. 1106-1117 (2008).

Chevalier, et al. "Interaction of murine BiP/GRP78 with the Dna homologue MTJ1." J Biol Chem., vol. 275(26), pp. 19620-1962(2000).

Clerici, Mario et al., "A TH1-TH2 switch is a critical step in the etiology of HIV infection," Immunology Today, vol. 14(3), pp. 107-111 (1993).

(56) References Cited

OTHER PUBLICATIONS

Dallman, M.J. "Cytokines and transplantation: Th1/Th2 regulation of the immune response to solid organ transplants in the adult" Curr. Opin. Immunol. vol. 7, pp. 632-638 (1995).

Davies, Michael, P.A., et al., "Expression and splicing of the unfolded protein response gene XBP-1 are significantly associated with clinical outcome of endocrine-treated breast cancer", International Journal of Cancer, vol. 123(1), pp. 85-88 (2008).

De Paula, Daniel et al., "Hydrophobization and bioconjugation for enhanced siRNA delivery and targeting," RNA, vol. 13, pp. 431-456 (2007).

Didierlaurent, A.M., et al., "AS04, an aluminum salt- and TLR4 agonist-based adjuvant system, induces a transient localized innate immune response leading to enhanced adaptive immunity," J Immunol., vol. 183, pp. 6186-6197 (2009).

Ding, Wen-Xing et al., "Differential Effects of Endoplasmic Reticulum Stress-Induced Autophagy on Cell Survival," The Journal of Biological Chemistry, vol. 282(7), pp. 4702-4710 (2007).

Ding, Wen-Xing et al., "Linking of Autophagy to Ubiquitin-Proteasome System is Important for the Regulation of Endoplasmic Reticulum Stress and Cell Viability," The American Journal, vol. 171(2), pp. 513-524 (2007).

Else, K. J. et al., "Cytokine-mediated Regulation of Chronic Intestinal Helminth Infection," The Journal of Experimental Medicine, vol. 179, pp. 347-351 (1994).

Fassler, R. et al. "Consequences of lack of .beta.1 integrin gene expression in mice" Genes & Development 9, pp. 1896-1908 (1995).

Fauci, A. S., "The Human Immunodeficiency Virus: Infectivity and Mechanisms of Pathogenesis," Science, vol. 239, pp. 617-622 (1988).

Feldman, Douglas E. et al., "The unfolded protein response: A novel component of the hypoxic stress response in tumors", Molecular Cancer Research, American Association for Cancer Research, US, vol. 3, pp. 597-605 (2005).

Foti, et al. "Conservation and divergence of the yeast and mammalian unfolded protein response. Activation of specific mammalian endoplasmic reticulum stress element of the grp78/BiP promoter by yeast Hac1." J Biol Chem., vol. 274(43), pp. 30402-30409 (1999).

Fowler, D.H. et al. "Donor CD4-Enriched Cells of Th2 Cytokine Phenotype Regulate Graft-Versus-Host Disease Without Impairing Allogeneic Engraftment in Sublethally Irradiated Mice" Blood, vol. 84(10), pp. 3540-3549 (1994).

Fowler, D.H. et al. "Donor Lymphoid Cells of Th2 Cytokine Phenotype Reduce Lethal Graft Versus Host Disease and Facilitate Fully Allogeneic Cell Transfers in Sublethally Irradiated Mice," Advances in Bone Marrow Purging and Processing: FourthInternational Symposium. Prog. Clin. Biol. Res., vol. 389, pp. 533-540 (1994).

Frank-Kamenetsky, M.et al., "Therapeutic RNAi targeting PCSK9 acutely lowers plasma cholesterol in rodents and LDL cholesterol in nonhuman primates," PNAS, vol. 105(33), pp. 11915-11920 (2008).

Fujimoto, T. et al., "Upregulation and overexpression of human x-box binding protein 1 (hXBP-1) gene in primary breast cancers", Breast Cancer, vol. 10 (4), pp. 301-306 (2003).

Gabay, C. et al. "Acute-Phase Proteins and Other Systemic Responses to Inflammation" New England Journal of Medicine, vol. 340(6), pp. 448-454 (1999).

Garrett, W.S., et al., "Communicable ulcerative colitis induced by T-bet deficiency in the innate immune system," Cell. vol. 131, pp. 33-45 (2007).

Gass, J. et al., "The unfolded protein response of B-lymphocytes: PERK-independent development of antibody-secreting cells," Molecular Immunology, vol. 45, pp. 1035-1043 (2008).

Gasser, S., et al, "The DNA damage pathway regulates innate immune system ligands of the NKG2D receptor," Nature, vol. 436, pp. 1186-1190 (2005).

Geething, et al. "Signal transduction pathway mediating the endoplasmic reticulum unfolded protein response: IRE1 and the ER chaperones," Molecular Biology. Vanderbilt University, Nashville, TN.

GenBank Accession No. A36299, Liou, HC et al., "A New Member of the leucine zipper class of proteins that binds to be HLA DR alpha promoter," Science, vol. 247 (4950) 1581-1584, 1990, 2 pages (1999).

GenBank Accession No. BAA82600, Kokura, K. et al., "Identity between rat htf and human xbp-1 genes: determination of gene structure, target sequence, and transcription promotion function for HTF," Gene, vol. 241(2):297-307 (2000), 2 pages (2000).

GenBank Accession No. CAA39149, Yoshimura, T. et al., "Multiple cDNA clones encoding nuclear proteins that bind to the tax-dependent enhancer of HTLV-2: all contain a leucine zipper structure and basic amino acid domain," EMBO J., vol. 9(8):2537-2542 (1990), 2 pages (2005).

GenBank Accession No. P17861, Liou, H.-C. et al., Science, vol. 247:1581-1584 (1990), 2 pages (1992).

Moore, M.W., et al., "Introduction of soluble protein into the class I pathway of antigen processing and presentation," Cell, vol. 54, pp. 777-785 (1988).

O'Neill, L. et al., "The family of five: TIR-domain-containing adaptors in Toll-like receptor signalling," Nat Rev Immunol, vol. 7, pp. 353-364 (2007).

Peisach E. et al., "Interaction of a peptidomimetic aminimide inhibitor with elastase," Science, vol. 269(5220), pp. 66-69 (1995).

Ravasi, T., et al., "Systems biology of transcription control in macrophages," Bioessays, vol. 29, pp. 1215-1226 (2007).

Raychaudhuri, S., et al., "Fully mobilizing host defense: building better vaccines," Nat Biotechnol., vol. 16, pp. 1025-1031 (1998).

Robertson, G. et al. "Genome-wide profiles of STAT1 DNA association using chromatin immunoprecipitation and massively parallel sequencing," Nat Methods, vol. 4, pp. 651-657 (2007).

Rock, K.L. et al., "Analysis of the role of MHC class II presentation in the stimulation of cytotoxic T lymphocytes by antigens targeted into the exogenous antigen-MHC class I presentation pathway," J Immunol., vol. 156, pp. 3721-3726 (1996).

Schmitz et al. Transcriptional activation induced in Macrophages by toll-like receptor (TLR) ligands: from expression profiling to a model of TLR signaling. European Journal of Immunology 34: 2863-2873(2004).

Struhl, K., "Transcriptional noise and the fidelity of initiation by RNA polymerase II," Nat Struct Mol Biol., vol. 14, pp. 103-105 (2007).

Van Beusechem, et al., "Long-Term Expression of Human Adenosine Deaminase in Rhesus Monkeys Transplanted With Retrovirus-Infected Bone-Marrow Cells" Proc. Natl. Acad. Sci. USA 89: 7640-7644, 1992.

Van Limbergen, J. et al., "The genetics of Crohn's disease," Annual Review of Genomics and Human Genetics 2009, vol. 10, May 2009, 89-116.

Xu, Y., "DNA damage: a trigger of innate immunity but a requirement for adaptive immune homeostasis," Nat Rev Immunol., vol. 6, pp. 261-270 (2006).

Yoshizaki, et al., "Pathogenic Significance of Interleukin-6 (IL-60/BSF-2) In Castleman's Disease." Blood 74: 1360-1367, 1989.

Zhu, X. et al., "Endoplasmic reticulum stress and its regulator XBP-1 contributes to dendritic cell maturation and activation induced by high mobility group box-1 protein," International Journal of Biochemistry and Cell Biology. Pergamon. GB., vol. 44. No. 7, Mar. 2012, 1097-1105.

Acsadi, et al., "Human Dystrophin Expression in mdx Mice After Intramuscular Injection of DNA Constructs," Nature, 333:815-818 (1991).

Akira, et al., "NF-IL6 and NF-Kappa B in Cytokine Gene Regulation," Adv Immunol., 65: 1-46 (1997).

Alton, et at, "Nucleotide Sequence Analysis of the Chloramphenicol Resistance Transposon Tn9" Nature 282: 864-869 (1979).

Aragon, T., et al, "Messenger RNA targeting to endoplasmic reticulum stress signalling sites," Nature, 457: 736-740 (2009).

Arpin, et al., "Generation of Memory B Cells and Plasma Cells In Vitro," Science 268: 720 (1995).

(56) References Cited

OTHER PUBLICATIONS

Askari, et al, "Molecular Medicine Antisense-Oligonucleotide Therapy" N. Engl. J. Med., 334:316-311(1996).
Attisano, et al., "Signal Transduction by the TGF beta Superfamily" Science 296: 1646 (2002).
Bai, et al, "A Mouse Model to Test the In Vivo Efficacy of Chemical Chaperones," J. of Pharm. and Toxicol. Methods, 40(1): 39-45 (1998).
Baldwin, et al., "Cloning of the Luciferase Structural Genes From Vibrio Harveyi and Expression of Bioluminescence in *Escherichia coli*," Biochemistry 23: 3663-366 (1984).
Banerji, et al., "A Lymphocyte-Specific Cellular Enhancer is Located Downstream of the Joining Region in Immunoglobulin Heavy Chain Genes" Cell 33: 729-740 (1983).
Barr, et al., "Identification of the Critical Features of a Small Peptide Inhibitor of JNK Activity,"; J. Biol. Chem., 277: 10987 (2002).
Bartel, et al., "Isolation of New Ribozymes From a Large Pool of Random Sequences," Science 261: 1411-1418, (1993).
Barthel, et al., "RNA Interference-based Strategies for Metabolic Syndrome Treatment," Horm. Metab. Res., 37: 59-62 (2005).
Beerli, et al., "Autocrine Inhibition of the Epidermal Growth Factor Receptor by Intracellular Expression of a Single-Chain Antibody," Biochem. Biophys. Res. Commun. 204: 666-672 (1994).
Bennet, et al., "JNK: A New Therapeutic Target for Diabetes," Current Opinion in Pharmacology, 3: 420-425 (2003).
Bennet, et al., "Antisense Therapy for Angioplasty Restenosis. Some Critical Considerations," Circulation, 92: 1981-1993 (1995).
Bertolotti, A., et al., "Dynamic interaction of BiP and ER stress transducers in the unfolded-protein response," Nat Cell Biol., 2:326-332 (2000).
Biocca, et al., "Intracellular Immunization With Cytosolic Recombinant Antibodies," Biotechnology 12: 396-399 (1994).
Blackman, et al., "A Model System for Peptide Hormone Action in Differentiation: Interleukin 2 Induces A B Lymphoma to Transcribe the J Chain Gene," Cell 47: 609-617 (1986).
Blumenthal, A., et al., "Common and unique gene expression signatures of human macrophages in response to four strains of *Mycobacterium avium* that differ in their growth and persistence characteristics," Infect Immun., 73: 3330-3341 (2005).
Boes, et al., "Enhanced B-1 Cell Development, But Impaired IgG Antibody Responses in Mice Deficient in Secreted IgM." J Immunol., 160: 4776-4787 (1998).
Bogoyevitch, et al., "Targeting the JNK MAPK Cascade for Inhibition: Basic Science and Therapeutic Potential" Biochimica et Biophysica Acta, 1697: 89-101 (2004).
Bonapace, et al., "Chemical Chaperones protect from the effect of apoptosis-inducing mutation in carbonic anhydrase IV identified in retinitis pigmentosa 17," PNAS, 101 (33): 12300-12305 (2004).
Boobbyer, et al., "New Hydrogen-Bond Potentials for Use in Determining Energetically Favorable Binding Sites on Molecules of Known Structure," J Med. Chem. 32: 1083 (1989).
Bossy-Wetzel, et al., "Assay for Cytochrome c Release From Mitochondria During Apoptosis" Methods in Enzymol., 322: 235-242 (2000).
Brown, et al., "Structural Characterization of Human Melanoma-Associated Antigen p97 With Monoclonal Antibodies," J Immunol., 127: 539-546 (1981).
Burdin, et al., "Endogenous IL-6 and IL-I 0 Contribute to the Differentiation of CD40-Activated Human B Lymphocytes," J Immunol., 154: 2533-2544 (1995).
Chen, et al., "Intracellular Antibodies as a New Class of Therapeutic Molecules for Gene Therapy," Human Gene Therapy, 5: 595-601 (1994).
Choe, et al., "IL-I 0 Interrupts Memory B Cell Expansion in the Germinal Center by Inducing Differentiation Into Plasma Cells," Eur J Immunol., 28: 508-515 (1998).
Clarkson, et al., "Making Antibody Fragments Using Phage Display Libraries" Nature 352: 624-628 (1991).
Cotton, "Current Methods of Mutation Detection," Mulot Res., 285: 125-144 (1992).

Cottrell, et al., "Silence of the Strands: RNA Interference in Eukaryotic Pathogens," Trends Microbioll.: 37-43, (2003).
Cox, J.et al. "Transcriptional induction of genes encoding endoplasmic reticulum resident proteins requires a transmembrane protein kinase," Cell, 73:1197-1206 (1993).
Cressman, et al., "Liver Failure and Defective Hepatocyte Regeneration in Interleukin-6-Deficient Mice," Science, 274: 1379-1383 (1996).
Darzynkiewicz, et al., "Analysis of Apoptotic Cells by Flow and Laser Scanning Cytometry," Methods in Enzymol. 322: 18-39, (2000).
Daugherty, et al., "Flow Cytometric Screening of Cell-Based Libraries," J Immunol. Methods, 243: 211 (2000).
Delepine, et al., "EIF2AK3, Encoding Translation Initiation Factor 2-a Kinase 3, Is Mutated in Patients with Wolcotl-Rallison Syndrome," Nat. Genet., 25: 406 (2000).
Desjarlias, et al., "Using Shape Complementarily as an Initial Screen in Designing Ligands for a Receptor Binding Site of Known Three-Dimensional Structure," J. Med. Chem., 31: 722 (1988).
Dioufa, N. et al., "A typical induction of the unfolded protein response by mifepristone," Endocrine, 38(2): 167-173 (2010).
Edlund, et al., "Cell Specific Expression of the Rat Insulin Gene: Evidence for Role of Two Distinct 5' Flanking Elements," Science, 230: 912-916 (1985).
Eggerding, et al., "Fluorescence-Based Oligonucleotide Ligation Assay for Analysis of Cystic Fibrosis Tranmembrane Conductance Regulator Gene Mutations," Hum. Mutat., 5: 153 (1995).
Eglitis, et at., "Gene Expression in Mice After High Efficiency Retroviral-Mediated Gene Transfer," Science, 230: 1395-1398 (1985).
Falo, L.D., et al., "Targeting antigen into the phagocytic pathway in vivo induces protective tumour immunity," Nat Med., 1: 649-653 (1995).
Friedlander, R. et al., "A regulatory link between ER-associated protein degradation and the unfolded protein response," Nature Cell Biology, 2:379-384 (2000).
Fuchs, et al., "Targeting Recombinant Antibodies to the Surface of *Escherichia coli*: Fusion to a Peptidoglycan Associated Lipoprotein," Bio/Technology, 9: 1370-1372 (1991).
Gefter, et al., "A Simple Method for Polyethylene Glycol-Promoted Hybridization of Mouse Myeloma Cells," Somatic Cell Genet., 3: 231-236 (1977).
Gething, et al., "Protein Folding in the Cell," Nature, 355: 33 (1992).
Gilchrist, M., et al., "Systems biology approaches identify ATF3 as a negative regulator of Toll-like receptor 4," Nature, 441: 173-178 (2006).
Gossen, et al., "Transcriptional Activation by Tetracyclines in Mammalian Cells," Science, 268: 1766-1769 (1995).
Greenbaum, Diabetes/Metabolism Research and Reviews, 18:192-200 (2002).
Bartel, et al., "Elimination of False Positives That Arise in Using the Two-Hybrid Systems" Biotechniques, 14: 920-924 (1993).
Berkner, "Development of Adenovirus Vectors for the Expression of Heterologous Genes" BioTechniques 6: 616-624 (1988).
Cohen, et al., "Emerging Technologies for Sequencing Antisense Oligonucleotides: Capillary Electrophoresis and Mass Spectrometry" Adv. Chromatgr. 36:127-162 (1996).
Helene, et al., "The Anti-Gene Strategy: Control of Gene Expression by Triplex-Forming-Oligonucleotides," Anticancer Drug Des., 6(6): 569-584 (1991).
Griffin, et al, "DNA Sequencing: Recent Innovations and Future Trends," Appl. Biochem. Biotechnol., 38: 147-159 (1993).
Hampton, et al., "ER Stress Response: Getting the UPR Hand on Misfolded Proteins," Curro; Biol., 10: R518 (2000).
Hanes, et al., "Picomolar Affinity Antibodies From a Fully Synthetic Naive Library Selected and Evolved by ribosome Display," Nat. Biotechnol., 18: 1287 (2000).
Harding, et al., "Diabetes Mellitus and Exocrine Pancreatic Dysfunctional Perk-I-Mice Reveals a Role for Translational Control in Secretary Cell Survival," Molecular Cell, 7: 1153-1163 (2001).

(56) References Cited

OTHER PUBLICATIONS

Harding, et al., "Protein Translation and Folding are Coupled by an Endoplasmic-Reticulum-Resident Kinase," Nature, 397: 271-274 (1999).
Haselhoff, et at, "Simple RNA Enzymes With New and Highly Specific Endoribonuclease Activities," Nature, 334: 585-591 (1988).
Hayashi, "PCR-SSCP: A Method for Detection of Mutations," Genet Anal Tech App., 9: 73-79 (1992).
Heikkila, et al., "The prevention of alloxan-induced diabetes in mice by dimethyl sulfoxide," European Journal of Pharmacology, Elsvier, BV, NL, 44(2):191-193(1977).
Helene, et al., "Control of Gene Expression by Triple Helix-Fonning Oligonucleotides," Ann. N. Y. Acad Sci. 660: 27-36 (1992).
Hertz, C., et al., "Proapoptotic BAX and BAK modulate the unfolded protein response by a direct interaction with IRE1alpha," Science, 312:572-576 (2006).
Hirano, et al., "Excessive Production of Interleukin 618 Cell Stimulatory Factor-2 in Rheumatoid Arthritis," Eur. J. Immunol.18: 1797-1801 (1988).
Hirano, et al., "Interleukin 6 and Plasma Cell Neoplasias," Prog. Growth Fact Res., 1: 133-142, (1989).
Hirosumi, et al., "A Central Role for JNK. In Obesity and Insulin Resistance," Nature, 420: 333-336 (2002).
Hollien, J.et al., "Decay of endoplasmic reticulum-localized mRNAs during the unfolded protein response," Science, 313: 104-107 (2006).
Horii, et al., "Involvement of IL-6 in Mesangial Proliferative Glomerulonephritis," J Immunol., 143(12): 3949-3955 (1989).
Hotamisligil, "Inflammatory Pathways and Insulin Action" International Journal of Obesity, 27: S53-S55 ( 2003).
Huang, Q. et al., "The plasticity of dendritic cell responses to pathogens and their components," Science, vol. 294, pp. 870-875 (2001).
Kaser, A. et al., "Endoplasmic reticulum stress in the intestinal epithelium and inflammatory bowel disease," Seminars in Immunology, W.B. Saunders Company, PA, US, 21 (3):156-163 (2009).
Kaufman, D.R., et al., "Trafficking of antigen-specific CD8+ T lymphocytes to mucosal surfaces following intramuscular vaccination," J Immunol., 181, 4188-4198 (2008).
Kawai, T., et al., "TLR signaling," Semin Immunol., 19: 24-32 (2007).
Koong, Albert C., "Targeting XBP-1 as a novel anti-cancer strategy," Cancer Biology & Therapy, 5(7):756-759 (2006).
Mahoney, D. et al. "Virus-tumor interactome screen reveals ER stress response can reprogram resistant cancers for oncolytic virus-triggered Caspase-2 cell death," Cancer Cell, Cell Press, US, 20(4): 443-456 (2011).
Malyala, P., et al., "The potency of the adjuvant, CpG oligos, is enhanced by encapsulation in PLG micropartites," J Pharm Sci., 97:1155-1164 (2008).
Malyala, P., et al., "Enhancing the therapeutic efficacy of CpG oligonudeotides using biodegradable microparticles," Adv Drug Deliv Rev., 61: 218-225 (2009).
McLean, C.Y., et al., "Great improves functional interpretation of cis-regulatory regions," Nat Biotechnol., 28(5): 495-501(2010).
Medzhitov, R., "Origin and physiological roles of inflammation," Nature, 454: 428-435 (2008).
Takahashi, T. et al., "Antiobesity agent for treating and preventing obesity, comprises extract of betaine, dandelion, turmeric, red pepper and/or Lonicera japonoica,as active ingredients" DERWENT, Jan. 1, 1900.
Atkinson et al., "The NOD mouse model of type 1 diabetes: As good as it gets?", Nature Medicine, 5(6):601-604 (1999).
André et al., "An inhibitor of HIV-1 protease modulates proteasome activity, antigen presentation, and T cell responses," Proc. Natl. Acad. Sci., USA, 95:13120-13124(1998).
Gruber et al., "Differential effects of HIV-1 protease inhibitors on dendritic cell immunophenotype and function," J. Biol. Chem., 276(51):47840-47843 (2001).
Whelan et al., "The HIV protease inhibitor Indinavir reduces immature dendritic cell transendothelial migration." Eur. J. Immunol., 33:2520-2530 (2003).

\* cited by examiner

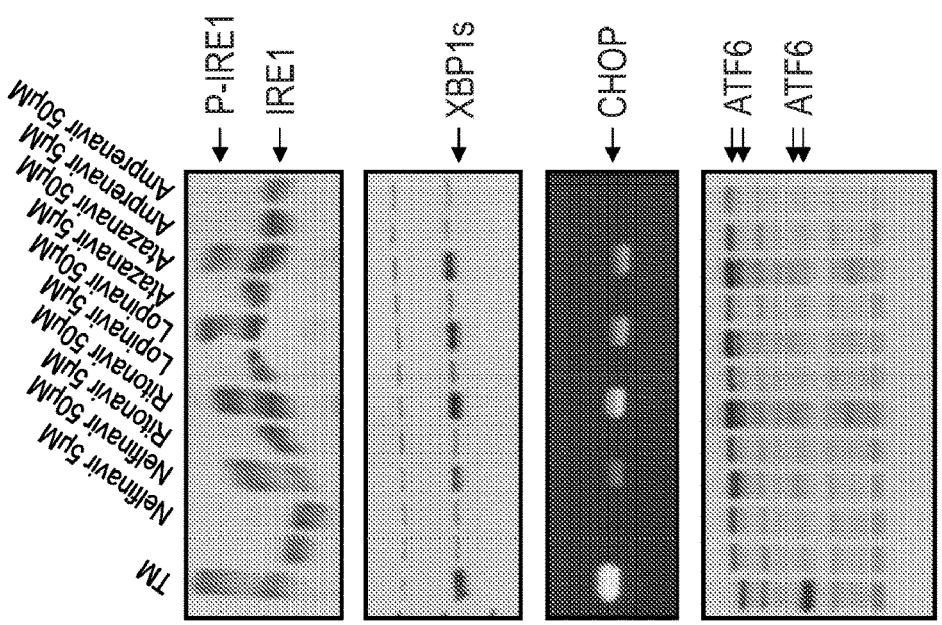
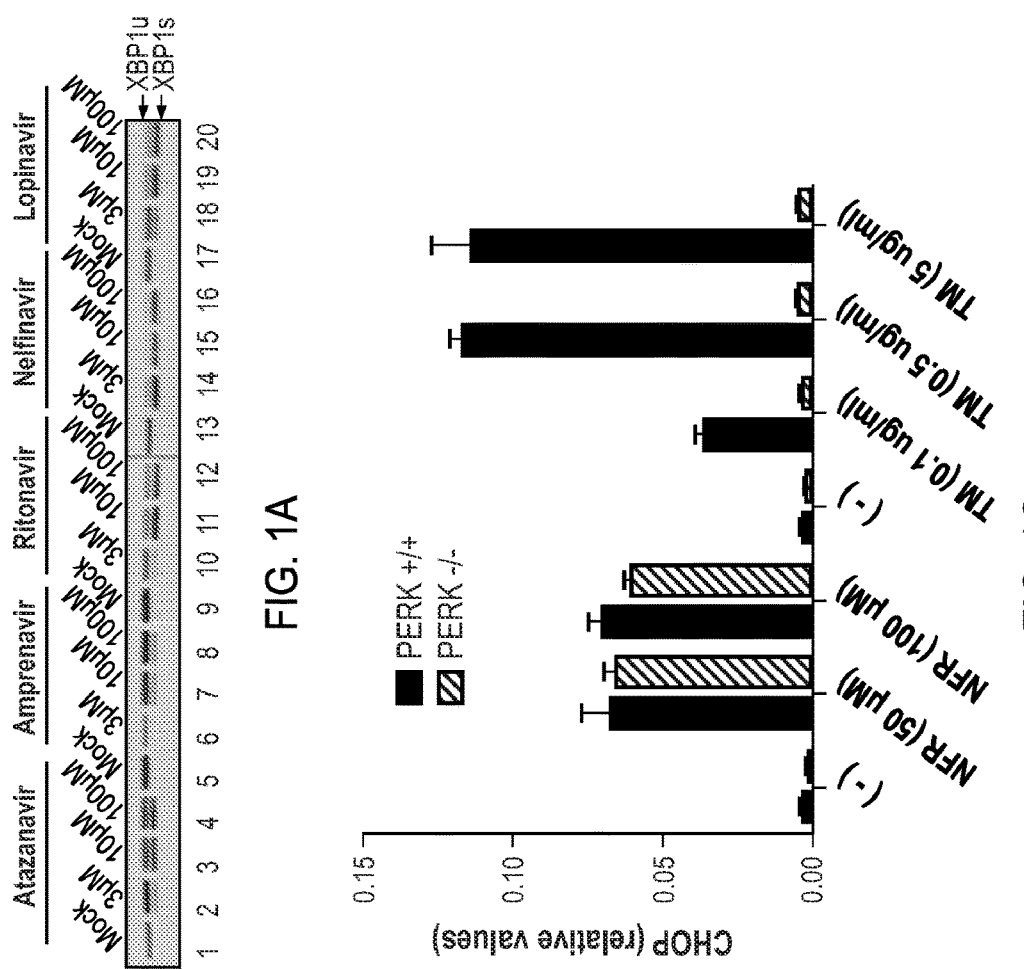
FIG. 1A
FIG. 1B
FIG. 1C

METHODS FOR INCREASING IMMUNE RESPONSES USING AGENTS THAT DIRECTLY BIND TO AND ACTIVATE IRE-1

REFERENCE TO RELATED APPLICATION

This application claims the benefit of U.S. Provisional Application Ser. No. 61/440,224 filed Feb. 7, 2011; which is herein incorporated by reference.

BACKGROUND OF THE INVENTION

The transcription factor XBP-1 was identified as a key regulator of the mammalian unfolded protein response (UPR) or endoplasmic reticulum (ER) stress response, which is activated by environmental stressors such as protein overload that require increased ER capacity (D. Ron, P. Walter (2007) Nat Rev Mol Cell Biol 8, 519). XBP-1 is activated by a post-transcriptional modification of its mRNA by IRE-1 alpha, an ER localizing proximal sensor of ER stress (M. Calfon et al. (2002) Nature 415, 92; H. Yoshida, et al. (2001) Cell 107, 881; X. Shen et al. (2001) Cell 107, 893). Upon ER stress, IRE-1 alpha induces an unconventional splicing of XBP-1 mRNA by using its endoribonuclease activity to generate a mature mRNA encoding an active transcription factor, XBP-1s, which directly binds to the promoter region of ER chaperone genes to promote transcription (A. L. Shaffer et al. (2004) Immunity 21, 81; A. H. Lee, et al. (2003) Mol Cell Biol 23, 7448; D. Acosta-Alvear et al. (2007) Mol Cell 27, 53). Mice deficient in XBP-1 display severe abnormalities in the development and function of professional secretory cells, such as plasma B cells and pancreatic acinar cells (N. N. Iwakoshi et al. (2003) Nat Immunol 4, 321; A. H. Lee, et al. (2005) Embo J 24, 4368) and intestinal Paneth cells (Kaser, et al (2008) Cell).

It has previously been shown that XBP-1 plays an important role in modulating toll-like receptor (TLR)-mediated responses and that enhancing XBP-1 activity can amplify the innate immune response. XBP-1 has also plays many other roles. For example, it been shown to activate the UPR, to increase proper protein folding and transport, to increase hepatocyte growth, and to increase plasma cell differentiation. The identification of agents that can be used to increase XBP-1 activity, e.g., by directly binding to and activating IRE-1 would be of great benefit in increasing immune cell activation, e.g., in the context of natural infection, vaccination, and cancer, as well as in promoting XBP-1 activity in other cell types.

FIGURE LEGENDS

Figure 1E:
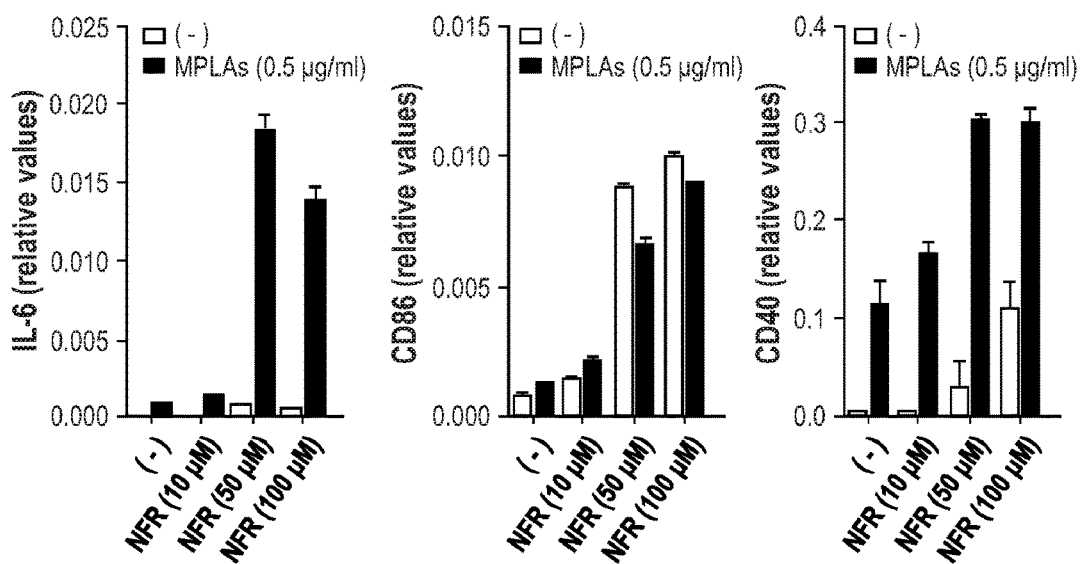

FIG. 1. HIV-protease inhibitors (PIs) trigger robust IRE1 and XBP1 activation and synergize with TLR4 activation to produce cytokines and co-stimulatory molecules. A) XBP1 mRNA maturation (XBP1s) in J774 cells stimulated with dose dependent concentrations of HIV-PIs (similar data were obtained in primary mouse M0s, and various M0 cell lines of human and mouse origin). B) Cell extracts of cells stimulated with Tunicamycin (TM) or HIV-protease inhibitors were monitored for IRE1 activation by phosphorylation in a Phos-tag SDS-PAGE gel, CHOP induction and ATF6a processing. C) Realtime PCR of CHOP induction by the ER-stress inducer TM and the HIV-PI Nelfinavir (NFR) was analyzed in PERK proficient and deficient MEFs. D) J774 cells were stimulated with HIV-PIs or TM as indicated in presence or absence of LPS and analyzed for IL-6 production by rtPCR. E) Increased IL-6 production and co-stimulatory ligand (CD86 and CD40) expression were observed in the presence of Nelfinavir and the synthetic TLR4 agonist MPLA compared to TLR4 agonist alone.

Figure 2A:
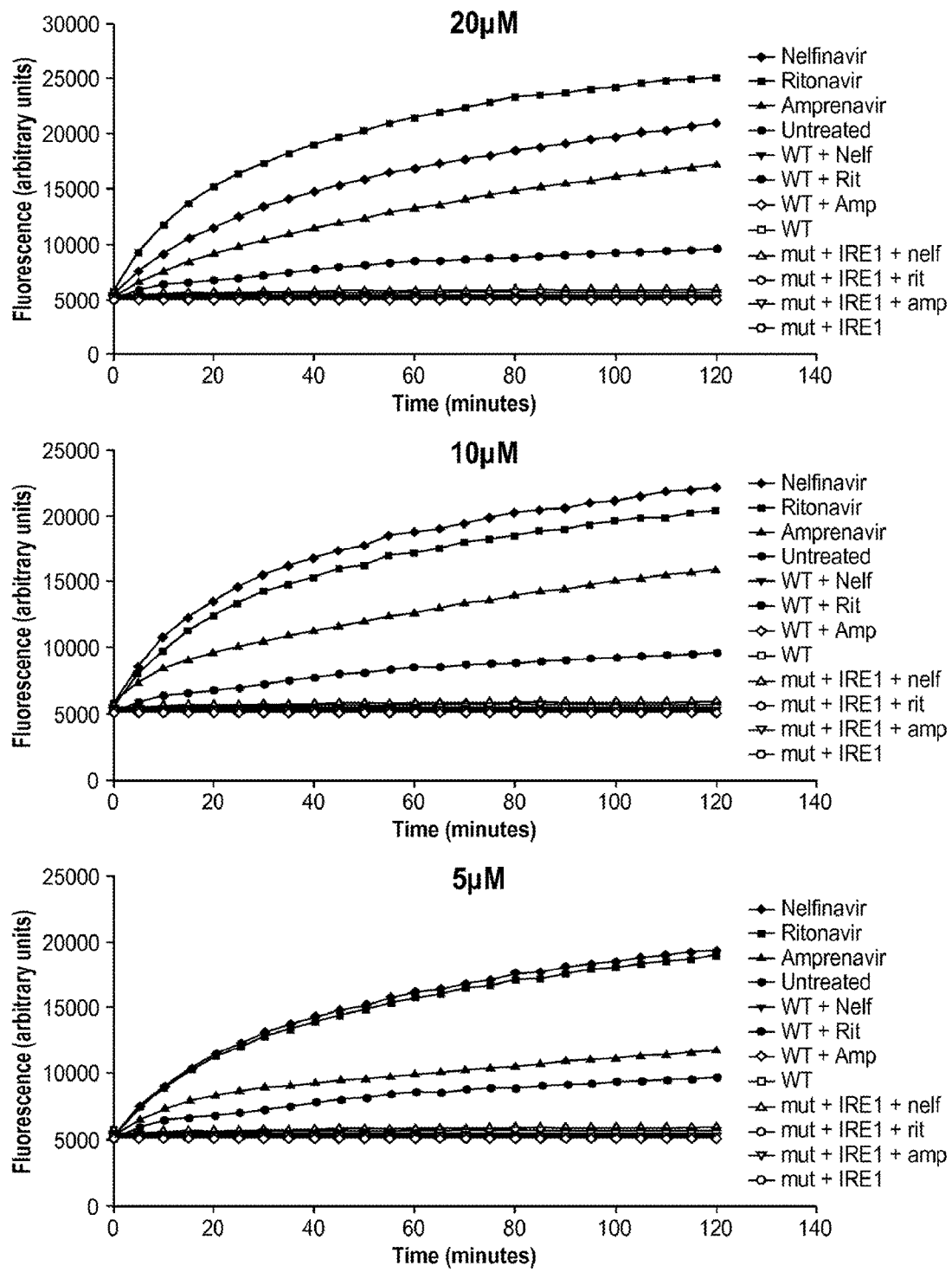
Figure 2B:
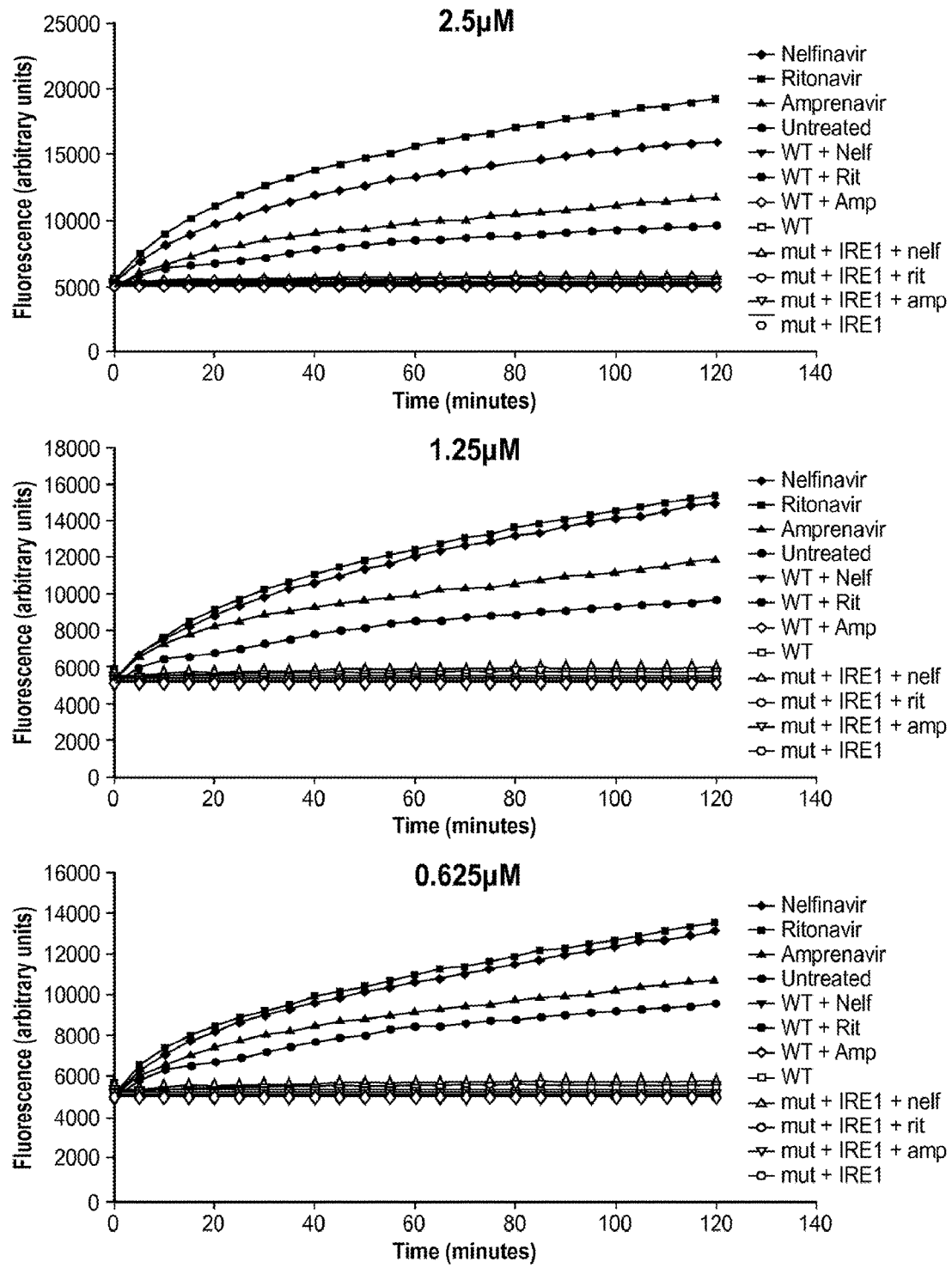

FIG. 2A-2B. In vitro fluorescent splicing reporter assay with recombinant IRE1 protein reveals marked induction of xbp1 splicing with ritonivir and nelfinivir but not amprenivir at doses of PIs ranging from 20 uM to 0.63 uM. FIG. 2A shows graphs of fluorescence over time at PIs ranging from 20 uM to 5 uM. FIG. 2B shows graphs of fluorescence over time at PIs ranging from 2.5 uM to 0.625 uM.

Figure 3:
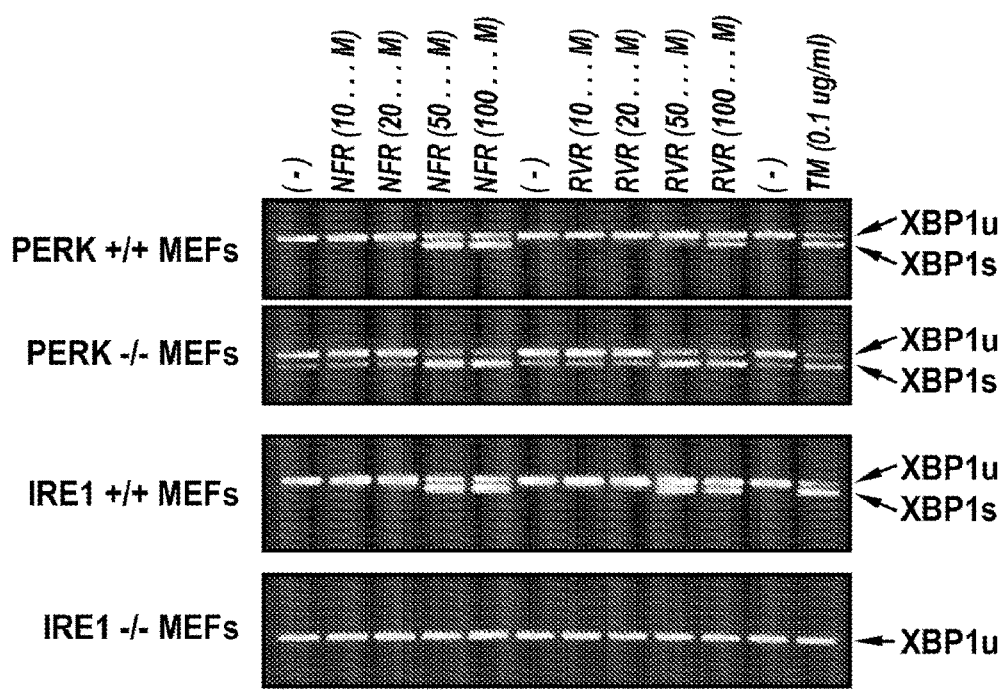

FIG. 3. HIV PIs induce splicing of XBP-1 in mouse embryonic fibroblasts.

SUMMARY OF THE INVENTION

The present invention demonstrates, inter alia, a role for agents that directly bind to and activate IRE-1, e.g., inhibitors of HIV proteases, in the activation of XBP-1, e.g., in immune cells and in other cell types. As described in the appended Examples, it has been discovered that agents that directly bind to IRE-1, e.g., at the interface between the subunits of the IRE-1 dimer, activate IRE-1 and thereby increase XBP-1 activity. These agents increase XBP-1 activity in cells that express IRE-1 and XBP-1. For example, these agents synergize with agonists of toll-like receptors to increase the production of cytokines and co-stimulatory molecules in immune cells, e.g., macrophages. Surprisingly, certain of these agents activate IRE-1 and do not activate PERK or ATF6 (the two other branches of the UPR) selectively activating the IRE-1 pathway in a non-ER stress dependent fashion, similar to toll-like receptors. These data point to a role for IRE-1 and XBP-1 that is separate from their role in classical ER-stress mediated responses. The fact that these agents synergize with TLR agonists to induce immune cell activation was also surprising.

Accordingly, in one aspect, the invention pertains to a method for increasing activation of XPB-1 in a cell which comprises IRE-1 and XBP-1 (e.g., a cell in vitro or present in a subject), comprising administering an agent that directly binds to and activates IRE-1 in the cell thereby increasing the activation of XPB-1 in the cell. In one embodiment, the cell is an immune cell. In another embodiment, the cell is a B cell. In another embodiment, the cell is a macrophage. In another embodiment, the cell expresses a heterologous protein.

In another aspect, the invention pertains to a method for increasing activation of immune cells in a subject, comprising administering an agent that directly binds to and activates IRE-1 to the subject thereby increase activation of immune cells in the subject.

In one embodiment, the subject is infected with a pathogen that does not express an HIV protease.

In one embodiment, the agent is an HIV protease inhibitor.

In one embodiment, the pathogen is selected from the group consisting of a bacterium, a virus, and a parasite.

In one embodiment, wherein the subject has cancer.

In one embodiment, the method further comprises administering the IRE1 agonist and at least one toll-like receptor agonist to the subject.

In one embodiment, the TLR agonist stimulates a TLR selected from the group consisting of: TLR2, TLR4, and TLR5. In one embodiment, the TLR agonist stimulates TLR4.

In one embodiment, the method further comprises contacting the immune cells with an antigen to which an immune response is desired.

In one embodiment, the production of a proinflammatory cytokine by the immune cells is increased. In one embodiment, the proinflammatory cytokine is IL-6.

In one embodiment, the expression of at least one costimulatory molecule is increased. In one embodiment, the expression of CD40 is increased.

In one embodiment, the immune cells comprise macrophages.

In on embodiment, the HIV protease inhibitor is selected from the group consisting of: Nelfinavir, Atazanavir, Lopinavir, and Ritonavir. In one embodiment, the HIV protease inhibitor is Nelfinavir.

In one embodiment, the activation of immune cells is increased in vivo.

In another aspect, the invention pertains to a method for increasing activation of a population of immune cells in vitro, wherein the population of cells comprises macrophages, comprising contacting the cells with an agent that directly binds to and activates IRE-1 thereby increasing activation of immune cells in vitro.

In one embodiment, the agent is an HIV protease inhibitor that binds to and activates IRE-1 such that XBP-1 is activated in the cells and the method further comprising determining the effects of XBP-1 activation on the cells in culture.

In another aspect, the invention pertains to a method for increasing protein production in vitro, comprising contacting cells which comprise a heterologus DNA molecule specifying a protein of interest with an agent that directly binds to and activates IRE-1 such that the amount of the protein of interest produced by the cells in vitro is increased.

In one embodiment, the invention pertains to a method of identifying compounds that enhance the innate immune response comprising, a) providing an immune cell comprising an IRE-1 polypeptide;

b) contacting the immune cell with each member of a library of compounds;

c) determining the ability of the compound to directly bind to IRE-1 and activate XBP-1 in the absence of activation of PERK or ATF6, d) the effect of the compound on at least one parameter of activation of the immune cell;

e) selecting a compound of interest that increases at least one parameter of activation of the immune cell to thereby identify the compound as useful in enhancing the innate immune response.

In one embodiment, the immune cell is a macrophage. In one embodiment, the immune cell is a B cell. In one embodiment, the immune cell is present in a mixed population of cells.

In another aspect, the invention pertains to a method of identifying improved HIV protease inhibitors comprising testing candidate HIV protease inhibitors for their ability to bind to IRE-1, wherein those agents that bind to HIV protease but have reduced ability to bind to IRE-1 are identified as being improved HIV protease inhibitors.

In one embodiment, the method further comprises altering the candidate HIV protease inhibitor to reduce the ability of the HIV protease inhibitor to bind to IRE-1.

In one embodiment, the invention pertains to a method of identifying improved IRE-1 inhibitors comprising testing candidate HIV protease inhibitors for their ability to bind to IRE-1, altering the candidate HIV protease inhibitors to decrease their binding to IRE-1, to thereby identify improved IRE-1 inhibitors.

In one embodiment, the invention pertains to a method of identifying improved IRE-1 agonists comprising testing candidate HIV protease inhibitors for their ability to bind to IRE-1, altering the candidate HIV protease inhibitors to increase their binding to IRE-1, to thereby identify improved IRE-1 agonists.

DETAILED DESCRIPTION

The instant invention is based, at least in part, on the discovery that agents that directly bind to the IRE-1 dimeric interface activate IRE-1. More specifically, as described in the appended Examples, it has been discovered that inhibitors of HIV proteases activate IRE-1 and thereby increase XBP-1 activity. In one embodiment, these agents increase immune cell activation. These same agents also activate IRE-1 and induce splicing of XBP-1 in other cell types which comprise IRE-1 and XBP-1 and are therefore useful in activating XBP-1 activity in other cells where it is desirable to do so. These agents synergize with agonists of toll-like receptors to increase the production of cytokines and co-stimulatory molecules in macrophages.

Certain terms are first defined so that the invention may be more readily understood.

I. Definitions

In one embodiment, the subject methods modulate the activity of the innate immune system. The "innate immune system" comprises the cells and mechanisms that defend the host from infection by other organisms, in a non-specific manner. The innate system, unlike the adaptive immune system, does not confer long-lasting or protective immunity to a host, e.g., antibody protection, but rather provides immediate defense against infection. The innate system is an evolutionarily older defense strategy, and is the dominant immune system found in plants, fungi, insects, and in primitive multicellular organisms, and in all classes of plant and animal life.

The major functions of the vertebrate innate immune system include recruiting immune cells to sites of infection and inflammation, through the production of cytokines; activation of the complement cascade to identify bacteria, activate cells and to promote clearance of dead cells or antibody complexes; identification and removal of foreign substances present in organs, tissues, the blood and lymph; and activation of the adaptive immune system through antigen presentation.

The innate immune system recognizes key molecular signatures of pathogens or "pathogen associated molecular patterns" (PAMPs), also referred to as "microbe-associated molecular patterns" (MAMPs) (R. Medzhitov, Nature 449, 819 (Oct. 18, 2007)) that include carbohydrates (e.g. structural components, e.g. lipopolysaccharide or LPS, mannose, peptidoglycans (PGN)), nucleic acids (e.g. bacterial or viral DNA or RNA, dsRNA, DNA), peptidoglycans and lipotechoic acids (from Gram positive bacteria), N-formylmethionine, lipoproteins and fungal glucans. The host organism harbors a group of receptors referred to as "pathogen recognition receptors" ("PRRs") that recognize these PAMPs, the best studied of which is the "Toll like receptors" ("TLRs") (K. J. Ishii, S. Koyama, A. Nakagawa, C. Coban, S Akira, Cell Host Microbe 3, 352 (Jun. 12, 2008)).

Pathogen recognition receptors, also referred to as "primitive pattern recognition receptors" are proteins expressed by cells of the immune system to identify molecules associated with microbial pathogens or cellular stress. PRRs are classified according to their ligand specificity, function, localization and/or evolutionary relationships. On the basis of function, PRRs may be divided into endocytic PRRs or signaling PRRs. Signaling PRRs include the large families of membrane-bound Toll-like receptors and cytoplasmic NOD-like receptors. Endocytic PRRs promote the attachment, engulfment and destruction of microorganisms by phagocytes, without relaying an intracellular signal. Endocytic PRRs recognize carbohydrates and include mannose receptors of macrophages, glucan receptors present on all phagocytes and scavenger receptors that recognize charged ligands, are found on all phagocytes and mediate removal of apoptotic cells.

TLRs are single membrane-spanning non-catalytic receptors that recognize structurally conserved molecules derived from microbes, e.g., PAMPs. TLRs together with the Interleukin-1 receptor, e.g., IL-1 and IL-18) form a receptor superfamily, known as the "Interleukin-1 Receptor/Toll-Like Receptor Superfamily"; members of this family are characterized structurally by an extracellular leucine-rich repeat (LRR) domain, a conserved pattern of juxtamembrane cysteine residues, and an intracytoplasmic signaling domain (Toll/IL-1 resistance or Toll-IL-1 receptor (TIR)) domain that forms a platform for downstream signaling by recruiting (via TIR-TIR interactions) TIR domain-containing adapters including MyD88, TIR domain-containing adaptor (TRAP), and TIR domain-containing adaptor inducing IFNβ (TRIF) (L. A. O'Neill, A. G. Bowie, Nat Rev Immunol 7, 353 (May 1, 2007)).

There are three subgroups of TIR domains. Proteins with subgroup 1 TIR domains are receptors for interleukins that are produced by macrophages, monocytes and dendritic cells and all have extracellular Immunoglobulin (Ig) domains. Proteins with subgroup 2 TIR domains are classical TLRs, and bind directly or indirectly to molecules of microbial origin, e.g., TLR5, TLR4 and TLR2. A third subgroup of proteins containing TIR domains consists of adaptor proteins that are exclusively cytosolic and mediate signaling from proteins of subgroups 1 and 2.

The nucleotide and amino acid sequences of TLRs are known and can be found at, for example, GenBank Accession Nos. gi:41350336, gi:13507602 (TLR1 human and mouse, respectively); gi:68160956, gi:158749637, gi:42476288 (TLR2 human, mouse, and rat, respectively); gi:19718735, GI:146149239, GI:38454315 (TLR3 human, mouse, and rat, respectively); GI:88758616, GI:118130391, gi:25742798 (TLR4 human, mouse, and rat, respectively); gi:124248535, gi:124248589, gi:109498326 (TLR5 human, mouse, and rat, respectively); gi:20143970, gi:157057100, gi:46485392 (TLR6 human, mouse, and rat, respectively); gi:67944638, gi:141803199, gi:147900683 (TLR7 human, mouse, and rat, respectively); gi:156071526, gi:126723494 (TLR8 human and mouse, respectively); gi:20302169, gi:157057165 (TLR9 human and mouse, respectively); there are two isoforms of TLR 10 in human, gi:62865620 and gi:62865617, gi:109499688 (TLR10 rat); gi:148539899, gi:221307462 (TLR11 mouse and rat, respectively); gi:148539900 (TLR12 mouse); gi:45429998 (TLR13 mouse).

TLR-mediated signaling in response to PAMPs is a sequential cascade of transcriptional regulatory events that vary depending on the TLR agonists, cell types involved and pathogenicity of the microbe. Individual genes (notably proinflammatory cytokines, e.g., IL-1 (alpha and beta), IL-6, IL-18, TNF-α) are induced transiently and then repressed reflecting the ability that the innate immune system has to interpret the infection and orchestrate appropriate responses while promoting resolution (T. Ravasi, C. A. Wells, D. A. Hume, Bioessays 29, 1215 (Nov. 15, 2007); J. C. Roach et al., Proc Natl Acad Sci USA 104, 16245 (Oct. 9, 2007); M. Gilchrist et al., Nature 441, 173 (May 11, 2006)). Nuclear factor-kappaB (NF-κB), the best characterized transcription factor downstream of TLRs, is activated by virtually all TLRs, e.g., TLR5, TLR4 and TLR2, through MyD88 or TRIF dependent pathways and is crucial for the production of proinflammatory cytokines. However, bacterial products are not the only signals that modulate innate immune responses-signals produced by stressed or damaged tissues have also been suggested to modulate the inflammatory response (H. Kono, K. L. Rock, Nat Rev Immunol 8, 279 (Apr. 1, 2008); R. Medzhitov, Nature 454, 428 (Jul. 24, 2008)).

The nucleotide and amino acid sequences of MyD88 are known and can be found at, for example, GenBank Accession Nos. gi:197276653, gi:31543276, gi:37693502 (human, mouse, rat, respectively).

The nucleotide and amino acid sequences of TIR domain-containing adaptor (TIRAP) are known and can be found at, for example, GenBank Accession Nos. gi:89111121 and gi:89111123 (two isoforms in himan), gi:16905130 and gi:109483246 (mouse and rat).

The nucleotide and amino acid sequences of TIR domain-containing adaptor inducing IFNβ (TRIF) are known and can be found at, for example, GenBank Accession Nos. gi:197209874 and gi:144227224 (human and mouse, respectively).

As used herein, the term "XBP-1" refers to the X-box binding protein. XBP-1 is a basic region leucine zipper (b-zip) transcription factor isolated independently by its ability to bind to a cyclic AMP response element (CRE)-like sequence in the mouse class II MHC Aα gene or the CRE-like site in the HTLV-1 21 base pair enhancer, and subsequently shown to regulate transcription of both the DRα and HTLV-1 ltr gene.

Like other members of the b-zip family, XBP-1 has a basic region that mediates DNA-binding and an adjacent leucine zipper structure that mediates protein dimerization. Deletional and mutational analysis has identified transactivation domains in the C-terminus of XBP-1 in regions rich in acidic residues, glutamine, serine/threonine and proline/glutamate. XBP-1 is present at high levels in plasma cells in joint synovium in patients with rheumatoid arthritis. In human multiple myeloma cells, XBP-1 is selectively induced by IL-6 treatment and implicated in the proliferation of malignant plasma cells. XBP-1 has also been shown to be a key factor in the transcriptional regulation of molecular chaperones and to enhance the compensatory UPR (Calfon et al., Nature 415, 92 (2002); Shen et al., Cell 107:893 (2001); Yoshida et al., Cell 107:881 (2001); Lee et al., Mol. Cell. Biol. 23:7448 (2003); each of which is incorporated herein by reference).

The amino acid sequence of XBP-1 is described in, for example, Liou, H-C. et. al. (1990) *Science* 247:1581-1584 and Yoshimura, T. et al. (1990) EMBO J. 9:2537-2542. The amino acid sequence of mammalian homologs of XBP-1 are described in, for example, in Kishimoto T. et al., (1996) *Biochem. Biophys. Res. Commun.* 223:746-751 (rat homologue). Exemplary proteins intended to be encompassed by the term "XBP-1" include those having amino acid sequences disclosed in GenBank with accession numbers A36299 [gi:105867]; AF443192 [gi: 18139942] (spliced murine XBP-1); P17861 [gi:139787]; CAA39149 [gi: 287645]; AF027963 [gi: 13752783] (murine unspliced XBP-1); BAB82982.1 [gi:18148382] (spliced human XBP- 1); BAB82981 [gi:18148380] (human unspliced XBP-1); and BAA82600 [gi:5596360] or e.g., encoded by nucleic acid molecules such as those disclosed in GenBank with accession numbers AF027963 [gi: 13752783]; NM_013842 [gi:13775155] (spliced murine XBP-1); or M31627 [gi: 184485] (unspliced murine XBP-1); AB076384 [gi: 18148381] (spliced human XBP-1); or AB076383 [gi: 18148379] (human unspliced XBP-1); gi:51948392 (rat). XBP-1 is also referred to in the art as TREB5 or HTF (Yoshimura et al. 1990. *EMBO Journal.* 9:2537; Matsuzaki et al. 1995. *J. Biochem.* 117:303).

There are two forms of XBP-1 protein, unspliced and spliced, which differ markedly in their sequence and activity. Unless the form is referred to explicitly herein, the term "XBP-1" as used herein includes both the spliced and unspliced forms.

As used herein, the term "spliced XBP-1" or "XBP-1s" refers to the spliced, processed form of the mammalian XBP-1 mRNA or the corresponding protein. Human and murine XBP-1 mRNA contain an open reading frame (ORF1) encoding bZIP proteins of 261 and 267 amino acids, respectively. Both mRNAs also contain another ORF, ORF2, partially overlapping but not in frame with ORF1. ORF2 encodes 222 amino acids in both human and murine cells. Human and murine ORF1 and ORF2 in the XBP-1 mRNA share 75% and 89% identity respectively. In response to ER stress, XBP-1 mRNA is processed by the ER transmembrane endoribonuclease and kinase IRE-1 which excises an intron from XBP-1 mRNA. In murine and human cells, a 26 nucleotide intron is excised. The boundaries of the excised introns are encompassed in an RNA structure that includes two loops of seven residues held in place by short stems. The RNA sequences 5' to 3' to the boundaries of the excised introns form extensive base-pair interactions. Splicing out of 26 nucleotides in murine and human cells results in a frame shift at amino acid 165 (the numbering of XBP-1 amino acids herein is based on GenBank accession number NM_013842 [gi:13775155] (spliced murine XBP-1) and one of ordinary skill in the art can determine corresponding amino acid numbers for XBP-1 from other organisms, e.g., by performing a simple alignment). This causes removal of the C-terminal 97 amino acids from the first open reading frame (ORF1) and addition of the 212 amino acids from ORF2 to the N-terminal 164 amino acids of ORF1 containing the b-ZIP domain. In mammalian cells, this splicing event results in the conversion of a 267 amino acid unspliced XBP-1 protein to a 371 amino acid spliced XBP-1 protein. The spliced XBP-1 then translocates into the nucleus where it binds to its target sequences to induce their transcription.

As used herein, the term "unspliced XBP-1" refers to the unprocessed XBP-1 mRNA or the corresponding protein. As set forth above, unspliced murineXBP-1 is 267 amino acids in length and spliced murine XBP-1 is 371 amino acids in length. The sequence of unspliced XBP-1 is known in the art and can be found, e.g., Liou, H-C. et. al. (1990) *Science* 247:1581-1584 and Yoshimura, T. et al. (1990) *EMBO J.* 9:2537-2542, or at GenBank accession numbers: AF443192 [gi: 18139942] (amino acid spliced murine XBP-1); AF027963 [gi: 13752783] (amino acid murine unspliced XBP-1); NM_013842 [gi:13775155] (nucleic acid spliced murine XBP-1); or M31627 [gi:184485] (nucleic acid unspliced murine XBP-1.

As used herein, the term "ratio of spliced to unspliced XBP-1" refers to the amount of spliced XBP-1 present in a cell or a cell-free system, relative to the amount or of unspliced XBP-1 present in the cell or cell-free system. "The ratio of unspliced to spliced XBP-1" refers to the amount of unspliced XBP-1 compared to the amount of unspliced XBP-1. "Increasing the ratio of spliced XBP-1 to unspliced XBP-1" encompasses increasing the amount of spliced XBP-1 or decreasing the amount of unspliced XBP-1 by, for example, promoting the degradation of unspliced XBP-1. Increasing the ratio of unspliced XBP-1 to spliced XBP-1 can be accomplished, e.g., by decreasing the amount of spliced XBP-1 or by increasing the amount of unspliced XBP-1. Levels of spliced and unspliced XBP-1 an be determined as described herein, e.g., by comparing amounts of each of the proteins which can be distinguished on the basis of their molecular weights or on the basis of their ability to be recognized by an antibody. In another embodiment described in more detail below, PCR can be performed employing primers with span the splice junction to identify unspliced XBP-1 and spliced XBP-1 and the ratio of these levels can be readily calculated.

In one embodiment, the subject methods can be used to activate the UPR in cells. As used herein, the term "Unfolded Protein Response" (UPR) or the "Unfolded Protein Response pathway" refers to an adaptive response to the accumulation of unfolded proteins in the ER and includes the transcriptional activation of genes encoding chaperones and folding catalysts and protein degrading complexes as well as translational attenuation to limit further accumulation of unfolded proteins. Both surface and secreted proteins are synthesized in the endoplasmic reticulum (ER) where they need to fold and assemble prior to being transported.

Since the ER and the nucleus are located in separate compartments of the cell, the unfolded protein signal must be sensed in the lumen of the ER and transferred across the ER membrane and be received by the transcription machinery in the nucleus. The unfolded protein response (UPR) performs this function for the cell. Activation of the UPR can be caused by treatment of cells with reducing agents like DTT, by inhibitors of core glycosylation like tunicamycin or by Ca-ionophores that deplete the ER calcium stores. First discovered in yeast, the UPR has now been described in *C. elegans* as well as in mammalian cells. In mammals, the UPR signal cascade is mediated by three types of ER transmembrane proteins: the protein-kinase and site—specific endoribonuclease IRE-1; the eukaryotic translation initiation factor 2 kinase, PERK/PEK; and the transcriptional activator ATF6. If the UPR cannot adapt to the presence of unfolded proteins in the ER, an apoptotic response is initiated leading to the activation of JNK protein kinase and caspases 7, 12, and 3. The most proximal signal from the lumen of the ER is received by a transmembrane endoribonuclease and kinase called IRE-1. Following ER stress, IRE-1 initiates splicing of the XBP-1 mRNA, the spliced version of which, activates the UPR.

Eukaryotic cells respond to the presence of unfolded proteins by upregulating the transcription of genes encoding ER resident protein chaperones such as the glucose-regulated BiP/Grp74, GrP94 and CHOP genes, folding catalysts and protein degrading complexes that assist in protein folding.

As used herein, the term "modulation of the UPR" includes both upregulation and downregulation of the UPR. As used herein the term "UPRE" refers to UPR elements upstream of certain genes which are involved in the activation of these genes in response, e.g., to signals sent upon the accumulation of unfolded proteins in the lumen of the endoplasmic reticulum, e.g., EDEM, Herp, e.g., ER stress-responsive cis-acting elements with the consensus sequence TGACGTGG/A (SEQ ID NO:XXX) (Wang, Y., et al. 2000. *J. Biol. Chem.* 275:27013-27020; Yoshida, H., et al. 2001.

Cell 107:881-891). Such elements are suitable for use in the screening assays of the invention.

As used herein, the term "ER stress" includes conditions such as the presence of reducing agents, depletion of ER lumenal Ca2+, inhibition of glycosylation or interference with the secretory pathway (by preventing transfer to the Golgi system), which lead to an accumulation of misfolded protein intermediates and increase the demand on the chaperoning capacity, and induce ER-specific stress response pathways. ER stress pathways involved with protein processing include the Unfolded Protein Response (UPR) and the Endoplasmic Reticulum Overload Response (EOR) which is triggered by certain of the same conditions known to activate UPR (e.g. glucose deprivation, glycosylation inhibition), as well as by heavy overexpression of proteins within the ER. The distinguishing feature of EOR is its association with the activation of the transcription factor NF-κB. Modulation of both the UPR and the EOR can be accomplished using the methods and compositions of the invention. ER stress can be induced, for example, by inhibiting the ER Ca2+ ATPase, e.g., with thapsigargin. As used herein, the term "protein folding or transport" encompasses posttranslational processes including folding, glycosylation, subunit assembly and transfer to the Golgi compartment of nascent polypeptide chains entering the secretory pathway, as well as extracytosolic portions of proteins destined for the external or internal cell membranes, that take place in the ER lumen. Proteins in the ER are destined to be secreted or expressed on the surface of a cell. Accordingly, expression of a protein on the cell surface or secretion of a protein can be used as indicators of protein folding or transport.

As used herein, the term "IRE-1" refers to an ER transmembrane endoribonuclease and kinase called inositol requiring enzyme, that oligomerizes and is activated by autophosphorylation upon sensing the presence of unfolded proteins, see, e.g., Shamu et al., (1996) EMBO J. 15: 3028-3039. In *Saccharomyces cerevisiae*, the UPR is controlled by IREp. In the mammalian genome, there are two homologs of IRE-1, IRE1α and IRE1β. IRE1α is expressed in all cells and tissue whereas IRE1β is primarily expressed in intestinal tissue. The endoribonucleases of either IRE1α and IRE1β are sufficient to activate the UPR. Accordingly, as used herein, the term "IRE-1" includes, e.g., IRE1α, IRE1β and IREp. In a preferred embodiment, IRE-1 refers to IRE1α.

IRE-1 is a large protein having a transmembrane segment anchoring the protein to the ER membrane. A segment of the IRE-1 protein has homology to protein kinases and the C-terminal has some homology to RNAses. Over-expression of the IRE-1 gene leads to constitutive activation of the UPR. Phosphorylation of the IRE-1 protein occurs at specific serine or threonine residues in the protein.

IRE-1 senses the overabundance of unfolded proteins in the lumen of the ER. The oligomerization of this kinase leads to the activation of a C-terminal endoribonuclease by trans-autophosphorylation of its cytoplasmic domains. IRE-1 uses its endoribonuclease activity to excise an intron from XBP-1 mRNA. Cleavage and removal of a small intron is followed by re-ligation of the 5' and 3' fragments to produce a processed mRNA that is translated more efficiently and encodes a more stable protein (Calfon et al. (2002) Nature 415(3): 92-95). The nucleotide specificity of the cleavage reaction for splicing XBP-1 is well documented and closely resembles that for IRE-p mediated cleavage of HAC1 mRNA (Yoshida et al. (2001) Cell 107:881-891). In particular, IRE-1 mediated cleavage of murine XBP-1 cDNA occurs at nucleotides 506 and 532 and results in the excision of a 26 base pair fragment (e.g., CAGCACTCAGACTACGTGCACCTCTG (SEQ ID NO:1) for mouse XBP-1). IRE-1 mediated cleavage of XBP-1 derived from other species, including humans, occurs at nucleotides corresponding to nucleotides 506 and 532 of murine XBP-1 cDNA, for example, between nucleotides 502 and 503 and 528 and 529 of human XBP-1.

There are two transcript variants of human IRE-1, the sequence of which are known in the art and can be found at, e.g., at GenBank accession numbers: gi:50345998 and gi:153946420. The nucleotide and amino acid sequences of mouse and rat IRE-1 nay be found at, e.g., at GenBank accession numbers: gi:15284149 and gi:109489193, respectively.

XBP-1 controls expression of several other genes, for example, ERdj4, p58ipk, EDEM, PDI-P5, RAMP4, HEDJ, BiP, ATF6α, XBP-1, Armet and DNAJB9, which encodes the 222 amino acid protein, mDj7 (GenBank Accession Number NM-013760 [gi:31560494]). These genes are important in a variety of cellular functions. For example, Hsp70 family proteins including BiP/Grp78 which is a representative ER localizing HSP70 member, function in protein folding in mammalian cells. A family of mammalian DnaJ/Hsp40-like proteins has recently been identified that are presumed to carry out the accessory folding functions. Two of them, Erdj4 and p58ipk, were shown to be induced by ER stress, localize to the ER, and modulate HSP70 activity (Chevalier et al. 2000 J Biol Chem 275: 19620-19627; Ohtsuka and Hata 2000 Cell Stress Chaperones 5: 98-112; Yan et al. 2002 Proc Natl Acad Sci USA 99: 15920-15925). ERdj4 has recently been shown to stimulate the ATPase activity of BiP, and to suppress ER stress-induced cell death (Kurisu et al. 2003 Genes Cells 8: 189-202; Shen et al. 2003 J Biol Chem 277: 15947-15956). ERdj4, p58IPK, EDEM, RAMP-4, PDI-P5 and HEDJ, all appear to act in the ER. ERdj4 (Shen et al. 2003), p58IPK (Melville et al. 1999 J Biol Chem 274: 3797-3803) and HEDJ (Yu et al. 2000 Mol Cell 6: 1355-1364) are localized to the ER and display Hsp40-like ATPase augmenting activity for the HspTO family chaperone proteins. EDEM was shown to be critically involved in the ERAD pathway by facilitating the degradation of ERAD substrates (Hosokawa et al. 2001 EMBO Rep 2:415-422; Molinari et al. 2003 Science 299 1397-1400; Oda et al. 2003 Science 299:1394-1397; Yoshida et al. 2003 Dev. Cell. 4:265-271). RAMP4 is a recently identified protein implicated in glycosylation and stabilization of membrane proteins in response to stress (Schroder et al. 1999 EMBO J. 18:4804-4815; Wang and Dobberstein 1999 Febs Lett 457:316-322; Yamaguchi et al. 1999 J. Cell Biol 147:1195-1204). PDI-P5 has homology to protein disulfide isomerase, which is thought to be involved in disulfide bond formation (Kikuchi et al. 2002 J. Biochem (Tokyo) 132:451-455). Collectively, these results show that the IRE1/XBP-1 pathway is required for efficient protein folding, maturation and degradation in the ER.

Another UPR signaling pathway is activated by the PERK protein kinase. PERK phosphorylates eIF2α, which induces a transient suppression of protein translation accompanied by induction of transcription factor(s) such as ATF4 (Harding et al. 2000 Mol Cell 6: 1099-1108). eIF2α is also phosphorylated under various cellular stress conditions by specific kinases, double strand RNA activated protein kinase PKR, the amino acid control kinase GCN2 and the heme regulated inhibitor HRI (Samuel 1993 J. Biol. Chem. 268: 7603-76-6; Kaufman 1999 Genes Dev. 13: 1211-1233). Since genes that are induced by the PERK pathway are also induced by other stress signals, such as amino acid deprivation, it is likely that PERK dependent UPR target genes carry out common cellular defense mechanisms, such as cellular homeostasis, apoptosis and cell cycle (Harding et al. 2003 Mol. Cell. 11619-633). Collectively, ER stress activates IRE/XBP-1 and PERK/eIF2α pathways to ensure proper maturation and degradation of secretory proteins and to effect common cellular defense mechanisms, respectively.

The reliance of p58IPK gene expression on XBP-1 connects two of the UPR signaling pathways, IRE1/XBP-1 and PERK. P58IPK was originally identified as a 58 kD inhibitor of PKR in influenza virus-infected kidney cells (Lee et al. 1990 Proc Natl Acad Sci USA 87: 6208-6212) and described to downregulate the activity of PKR by binding to its kinase domain (Katze 1995 Trends Microbiol 3: 75-78). It also has a J domain in the C-terminus which has been shown to participate in interactions with Hsp70 family proteins Melville et al. 1999 J Biol Chem 274: 3797-380). Recently Katze and colleagues have demonstrated that p58IPK interacts with ERK which is structurally similar to PKR, inhibits its eIF2α kinase activity and that it is induced during the UPR by virtue of an ER stress-response element in its promoter region (Yan et al. 2002 Proc Natl Acad Sci USA 99: 15920-15925).

As used herein the term "activating transcription factors 6" include ATF6α and ATF6β. ATF6 is a member of the basic-leucine zipper family of transcription factors. It contains a transmembrane domain and is located in membranes of the endoplasmic reticulum. ATF6 is constitutively expressed in an inactive form in the membrane of the ER. Activation in response to ER stress results in proteolytic cleavage of its N-terminal cytoplasmic domain by the S2P serine protease to produce a potent transcriptional activator of chaperone genes (Yoshida et al. 1998 *J. Biol. Chem.* 273: 33741-33749; Li et al. 2000 *Biochem J* 350 Pt 1: 131-138; Ye et al. 2000 *Mol Cell* 6: 1355-1364; Yoshida et al. 2001 *Cell* 107: 881-891; Shen et al. 2002 *Dev Cell* 3: 99-111). The recently described ATF6β is closely related structurally to ATF6α and posited to be involved in the UPR (Haze et al. 2001 *Biochem J* 355: 19-28; Yoshida et al. 2001b *Mol Cell Biol* 21: 1239-1248). The third pathway acts at the level of posttranscriptional control of protein synthesis. An ER transmembrane component, PEK/PERK, related to PKR (interferon-induced double-stranded RNA-activated protein kinase) is a serine/threonine protein kinase that acts in the cytoplasm to phosphorylate eukaryotic initiation factor-2α (eIF2α). Phosphorylation of eIF2α results in translation attenuation in response to ER stress (Shi et al. 1998 *Mol. Cell. Biol.* 18: 7499-7509; Harding et al. 1999 *Nature* 397: 271-274).

The nucleotide and amino acid sequences of ATF6 are known in the art and can be found at, e.g., at GenBank accession number: gi:56786156, gi:124486810, gi:157821878 (human, mouse, rat, respectively).

As used herein, the various forms of the term "modulate" include stimulation (e.g., increasing or upregulating a particular response or activity) and inhibition (e.g., decreasing or downregulating a particular response or activity).

As used herein, the terms "a modulator of XBP-1" and "a modulator of IRE-1" include modulators of XBP-1 and/or IRE-1 expression, processing, post-translational modification, stability, and/or activity. The term includes agents, for example which bind to and directly activate IRE-1 and, thereby, increase the activity of XBP-1.

The term "interact" or "bind" as used herein is meant to include detectable interactions between molecules, such as can be detected using, for example, by virtue of the effect they have on a molecule to which they bind or by structural modeling methods. The term interact is also meant to include "binding" interactions between molecules. Binding interations can be determined, e.g., by isothermal titration calorimetry (ITC) and is read out as a change in the thermodynamic enthalpy of the reaction.

As used herein, the term "contacting" (i.e., contacting a cell e.g. a cell, with a compound) includes incubating the compound and the cell together in vitro (e.g., adding the compound to cells in culture) as well as administering the compound to a subject such that the compound and cells of the subject are contacted in vivo. The term "contacting" does not include exposure of cells to an XBP-1 and/or IRE-1 modulator that may occur naturally in a subject (i.e., exposure that may occur as a result of a natural physiological process).

As used herein, the term "test compound" refers to a compound that has not previously been identified as, or recognized to be, a modulator of the activity being tested. The term "library of test compounds" refers to a panel comprising a multiplicity of test compounds.

As used herein with respect to screening methods and methods of modulating innate immune responses, the term "cell" includes mammalian cells. In a preferred embodiment, a cell of the invention is a murine or human cell.

As used herein, the term "engineered" (as in an engineered cell) refers to a cell into which a nucleic acid molecule e.g., encoding a heterologous protein, e.g., an XBP-1 protein (e.g., a spliced and/or unspliced form of XBP-1) has been introduced.

As used herein, the term "reporter gene" refers to any gene that expresses a detectable gene product, e.g., RNA or protein. As used herein the term "reporter protein" refers to a protein encoded by a reporter gene. Preferred reporter genes are those that are readily detectable. The reporter gene can also be included in a construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864-869) luciferase, and other enzyme detection systems, such as beta-galactosidase; firefly luciferase (deWet et al. (1987), *Mol. Cell. Biol.* 7:725-737); bacterial luciferase (Engebrecht and Silverman (1984), *PNAS* 1: 4154-4158; Baldwin et al. (1984), *Biochemistry* 23: 3663-3667); alkaline phosphatase (Toh et al. (1989) *Eur. J. Biochem.* 182: 231-238, Hall et al. (1983) *J. Mol. Appl. Gen.* 2: 101), human placental secreted alkaline phosphatase (Cullen and Malim (1992) *Methods in Enzymol.* 216:362-368) and green fluorescent protein (U.S. Pat. No. 5,491,084; WO 96/23898).

As used herein, the term "XBP-1-responsive element" refers to a DNA sequence that is directly or indirectly regulated by the activity of the XBP-1 (whereby activity of XBP-1 can be monitored, for example, via transcription of a reporter gene).

In one embodiment, small molecules can be used as test compounds. The term "small molecule" is a term of the art and includes molecules that are less than about 7500, less than about 5000, less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., Cane et al. 1998. Science 282:63), and natural product extract libraries. In another embodiment, the compounds are small, organic non-peptidic compounds. In a further embodiment, a small molecule is not biosynthetic. For example, a small molecule is preferably not itself the product of transcription or translation. In one embodiment, small molecule compounds are present on a microarray, see, e.g., Bradner J E, et al. 2006. Chem. Biol. 13(5): 493-504.

As used herein the term "antigen" refers to a molecule to which an immune response is desired. Such antigens may be purified or may be crude preparations comprising multiple antigens or may be whole organisms (e.g., inactivated or attenuated virus particles or non-lethal bacteria). In one embodiment, an antigen comprises a protein. In another embodiment, an antigen is administered in the form of a nucleic acid molecule encoding a protein.

As used herein the term "costimulatory molecule" refers to membrane-bound or secreted product of accessory cells that is required for activation of T or B cells.

As used herein the term macrophage refers to white blood cells produced by the differentiation of monocytes in tissues. Human macrophages are about 21 micrometers (0.00083 in) in diameter. Monocytes and macrophages are phagocytes. Macrophages function in both non-specific defense (innate immunity) as well as help initiate specific defense mechanisms (adaptive immunity) of vertebrate animals. Macrophages can be identified by specific expression of a number of proteins including CD14, CD11b, F4/80 (mice)/EMR1 (human), Lysozyme M, MAC-1/MAC-3 and CD68 by flow cytometry or immunohistochemical staining.

Various aspects of the present invention are described in further detail in the following subsections.

II. Agents that Directly Bind to and Activate Ire-1

In one embodiment, agents that directly bind to and activate IRE-1 can be used to activate XBP-1 in cells that comprise both IRE-1 and XBP-1. In one embodiment, such cells endogenously express one or both of these molecules. In another embodiment, such cells express exogenous or heterologous IRE-1 and/or XBP-1 molecules. In one embodiment, such agents bind to a site at the interface of the two subunits of the IRE-1 dimer, i.e., at the dimerization interface. In one embodiment, such agents do not bind to the portion of the IRE-1 dimer that is bound by the IRE-1 inhibitor quercetin. In another embodiment, such agents bind to the portion of the IRE-1 dimer that is bound by quercetin. In one embodiment, such agents contain a synthetic analog of the phenylalanine-proline sequence found at positions 167 and 168 of retroviral gag-pol polyprotein.

In one embodiment, agents that bind to and selectively activate IRE-1 do not activate PERK and ATF6, the two other branches of the UPR.

In one embodiment such agents are HIV protease inhibitors that prevent cleavage of gag and gag-pol protein precursors in acutely and chronically infected cells, arresting maturation and thereby blocking the infectivity of nascent virions. Exemplary such inhibitors include indinavir (Crixivan), nelfinavir (Viracept), ritonavir (Norvir), and saquinavir (Invirase and Fortovase), etazanavir (Reyataz) and the investigational protease inhibitor amprenavir.

In one embodiment, these agents may be administered to a subject at the same approximate dose currently used for HIV therapy (e.g., approximately between 600-800 mg every 8 hours, two time a day, or three times a day). In another embodiment, such agents may be administered at a lower dose than than currently administered for treatment of HIV, thereby reducing potential side effects associated with such administration. For example, such agents may be used at doses of about 1 mg, 3 mg, 10 mg, 30 mg, 100 mg, 300 mg, 400 mg, 500 mg, 600 mg, 700 mg, 800 mg, 900 mg, 1000 mg. Agents may be administered multiple times (e.g., multiple times per day, multiple times per week, multiple times per month).

III TLR Agonists

In one embodiment, an agent that binds to and activates IRE-1 can be used in combination with a TLR agonist, e.g., for contacting cells in vitro or in vivo. Exemplary TLR agonists are known in the art.

TLR2 mediates cellular responses to a large number of microbial products including peptidoglycan, bacterial lipopeptides, lipoteichoic acid, mycobacterial lipoarabinomannan and yeast cell wall components In another embodiment, an agonist of TLR2 can be used in combination with an agent that binds to and directly activates IRE-1. Exemplary such TLR2 agonists include mycobacterial cell wall glycolipids, lipoarabinomannan (LAM) and mannosylated phosphatidylinositol (PIIM), MALP-2 and Pam3Cys and synthetic variants thereof.

In another embodiment, an agonist of TLR4 can be used in combination with an agent that binds to and directly activates IRE-1. Exemplary such TLR4 agonists include lipopolysaccharide or synthetic variants thereof (e.g., MPL and RC529) and lipid A or synthetic variants thereof (e.g., aminoalkyl glucosaminide 4-phosphates). See, e.g., Cluff et al. 2005 Infection and Immunity, p. 3044-3052:73; Lembo et al. *The Journal of Immunology,* 2008, 180, 7574-7581; Evans et al. 2003. *Expert Rev Vaccines* 2:219-29. Many such agents are commercially available.

In another embodiment, an agonist of TLR5 can be used in combination with an agent that binds to and directly activates IRE-1. Exemplary such TLR5 agonists include flagellin or synthetic variants thereof (e.g., A pharmacologically optimized TLR5 agonist with reduced immunogenicity (such as CBLB502) made by deleting portions of flagellin that are non-essential for TLR5 activation).

IV. Methods of Activating XBP-1

Activation of XBP-1 has been shown to have a variety of effects in numerous cell types. For example, XBP-1 activation increases de novo hepatic lipogenesis, increases hepatocyte growth, increases plasma cell differentiation, increases T cell activation, increases IL-6 production, increases the unfolded protein response, and increases protein folding and transport to thereby increase protein expression in cells. The subject methods employ agents that directly bind to IRE-1 and thereby increase XBP-1 activity. These agents may be used to increase XBP-1 activity in cells in which it is desirable to do so.

In one embodiment, XBP-1 can be activated in cells using an IRE-1 agonist of the invention to treat a disorder associated with protein trafficking. In one embodiment, the disorder is a synucleinopathy. Synucleins are a family of small, presynaptic neuronal proteins composed of alpha-, beta-, and gamma-synucleins, of which only alpha-synuclein aggregates have been associated with several neurological diseases (Ian et al., Clinical Neurosc. Res. 1:445-455, 2001; Trojanowski and Lee, Neutrotoxicology 23:457-460, 2002). The role of synucleins (and in particular, alpha-synuclein) in the etiology of a number of neurodegenerative and/or amyloid diseases has developed from several observations. Pathologically, alpha-synuclein was identified as a major component of Lewy bodies, the hallmark inclusions of Parkinson's disease, and a fragment thereof was isolated from amyloid plaques of a different neurological disease, Alzheimer's disease. Biochemically, recombinant alpha-synuclein was shown to form amyloid-like fibrils that recapitulated the ultrastructural features of alpha-synuclein isolated from patients with dementia with Lewy bodies, Parkinson's disease and multiple system atrophy. Additionally, the identification of mutations within the alpha-synuclein gene, albeit in rare cases of familial Parkinson's disease, demonstrated an unequivocal link between synuclein pathology and neurodegenerative diseases. The common involvement of alpha-synuclein in a spectrum of diseases such as Parkinson's disease, dementia with Lewy bodies, multiple system atrophy and the Lewy body variant of Alzheimer's disease has led to the classification of these diseases under the umbrella term of "synucleinopathies."

In some embodiments, the disorder characterized by impaired protein trafficking is a lysosomal storage disorder such as Fabry disease, Farber disease, Gaucher disease, $GM_1$-gangliosidosis, Tay-Sachs disease, Sandhoff disease, $GM_2$ activator disease, Krabbe disease, metachromatic leukodystrophy, Niemann-Pick disease (types A, B, and C), Hurler disease, Scheie disease, Hunter disease, Sanfilippo disease, Morquio disease, Maroteaux-Lamy disease, hyaluronidase deficiency, aspartylglucosaminuria, fucosidosis, mannosidosis, Schindler disease, sialidosis type 1, Pompe disease, Pycnodysostosis, ceroid lipofuscinosis, cholesterol ester storage disease, Wolman disease, Multiple sulfatase, galactosialidosis, mucolipidosis (types II, III, and IV), cystinosis, sialic acid storage disorder, chylomicron retention disease with Marinesco-Sjogren syndrome, Hermansky-Pudlak syndrome, Chediak-Higashi syndrome, Danon disease, or Geleophysic dysplasia. Lysosomal storage disorders are reviewed in, e.g., Wilcox (2004) J. Pediatr 144:S3-S14.

In some embodiments, the disorder characterized by impaired protein trafficking is characterized by an impaired delivery of cargo to a cellular compartment.

In some embodiments, the disorder characterized by impaired protein trafficking is characterized by a Rab27a mutation or a deficiency of Rab27a. The disorder can be, e.g., Griscelli syndrome.

In some embodiments, the disorder characterized by impaired protein trafficking is cystic fibrosis.

In some embodiments, the disorder characterized by impaired protein trafficking is diabetes (e.g., diabetes mellitus).

In some embodiments, the disorder characterized by impaired protein trafficking is hereditary emphysema, hereditary hemochromatosis, oculocutaneous albinism, protein C deficiency, type I hereditary angioedema, congenital sucrase-isomaltase deficiency, Crigler-Najjar type II, Laron syndrome, hereditary Myeloperoxidase, primary hypqthyroidism, congenital long QT syndrome, tyroxine binding globulin deficiency, familial hypercholesterolemia, familial chylomicronemia, abeta-lipoproteinema, low plasma lipoprotein a levels, hereditary emphysema with liver injury, congenital hypothyroidism, osteo genesis imperfecta, hereditary hypofibrinogenemia, alpha-lantichymotrypsin deficiency, nephrogenic diabetes insipidus, neurohypophyseal diabetes, insipidus, Charcot-Marie-Tooth syndrome, Pelizaeus Merzbacher disease, von Willebrand disease type IIA, combined factors V and VIII deficiency, spondyloepiphyseal dysplasia tarda, choroideremia, I cell disease, Batten disease, ataxia telangiectasias, acute lymphoblastic leukemia, acute myeloid leukemia, myeloid leukemia, ADPKD-autosomal dominant polycystic kidney disease, microvillus inclusion disease, tuberous sclerosis, oculocerebro-renal syndrome of Lowe, amyotrophic lateral sclerosis, myelodysplastic syndrome, Bare lymphocyte syndrome, Tangier disease, familial intrahepatic cholestasis, X-linked adreno-leukodystrophy, Scott syndrome, Hermansky-Pudlak syndrome types 1 and 2, Zellweger syndrome, rhizomelic chondrodysplasia puncta, autosomal recessive primary hyperoxaluria, Mohr Tranebjaerg syndrome, spinal and bullar muscular atrophy, primary ciliary diskenesia (Kartagener's syndrome), Miller Dieker syndrome, lissencephaly, motor neuron disease, Usher's syndrome, Wiskott-Aldrich syndrome, Optiz syndrome, Huntington's disease, hereditary pancreatitis, anti-phospholipid syndrome, overlap connective tissue disease, Sjogren's syndrome, stiff-man syndrome, Brugada syndrome, congenital nephritic syndrome of the Finnish type, Dubin-Johnson syndrome, X-linked hypophosphosphatemia, Pendred syndrome, persistent hyperinsulinemic hypoglycemia of infancy, hereditary spherocytosis, aceruloplasminemia, infantile neuronal ceroid lipofuscinosis, pseudoachondroplasia and multiple epiphyseal, Stargardt-like macular dystrophy, X-linked Charcot-Marie-Tooth disease, autosomal dominant retinitis pigmentosa, Wolcott-Rallison syndrome, Cushing's disease, limb-girdle muscular dystrophy, mucoploy-saccharidosis type IV, hereditary familial amyloidosis of Finish, Anderson disease, sarcoma, chronic myelomonocytic leukemia, cardiomyopathy, faciogenital dysplasia, Torsion disease, Huntington and spinocerebellar ataxias, hereditary hyperhomosyteinemia, polyneuropathy, lower motor neuron disease, pigmented retinitis, seronegative polyarthritis, interstitial pulmonary fibrosis, Raynaud's phenomenon, Wegner's granulomatosis, preoteinuria, CDG-Ia, CDG-Ib, CDG-Ic, CDG-Id, CDG-Ie, CDG-If, CDG-IIa, CDG-IIb, CDG-IIc, CDG-IId, Ehlers-Danlos syndrome, multiple exostoses, Griscelli syndrome (type 1 or type 2), or X-linked non-specific mental retardation. Disorders characterized by impaired protein trafficking are reviewed in Aridor et al. (2000) Traffic 1:836-51 and Aridor et al. (2002) Traffic 3:781-90.

In one embodiment, the subject IRE-1 agonists can be used to activate XBP-1 in a cell expressing an endogenous protein to thereby increase production of properly folded protein molecules. In one embodiment, the agonists can be used to activate XBP-1 in a cell expressing an exogenous protein (e.g., one that has been transfected into the cell) to thereby increase production of a commercially valuable properly folded protein molecule. The protein molecule can be obtained by culture of the cell in vitro and recovery of the protein molecule from the medium or from the cells.

XBP-1 also plays a key role in TLR-mediated signaling in cells of the innate immune system. Accordingly, in one embodiment, the invention features methods for enhancing the TLR-mediated activation of cells of the innate immune system or of enhancing an innate immune response in a subject.

The claimed methods are not meant to include naturally occurring events. For example, the step of contacting includes administering the modulator in a treatment protocol and, in one embodiment the term "agent" or "modulator" is not meant to embrace endogenous mediators produced by the cells of a subject.

The methods can be practiced either in vitro or in vivo. For practicing the method in vitro, cells can be obtained from a subject by standard methods and incubated (i.e., cultured) in vitro with an agent that binds directly to IRE-1 and, optionally a TLR agonist. Methods for isolating immune cells are known in the art.

Cells treated in vitro can be administered to a subject. For administration of cells to a subject, it may be preferable to first remove residual compounds in the culture from the cells before administering them to the subject. This can be done for example by gradient centrifugation of the cells or by washing.

In one embodiment, the cell is a mammalian cell. In another embodiment, the cell is a human cell.

The term "subject" is intended to include living organisms but preferred subjects are mammals. Examples of subjects include mammals such as, e.g., humans, monkeys, dogs, cats, mice, rats cows, horses, goats, and sheep.

In one embodiment, the subject does not have HIV and is not undergoing therapy with HIV protease inhibitors to reduce retroviral proliferation.

Vaccination

In one embodiment, agents that bind to and directly activate IRE-1 can be used as part of a vaccine. As used herein, "vaccine" means an organism or material that contains an antigen in an innocuous form. The vaccine is designed to trigger an immunoprotective response. The vaccine may be recombinant or non-recombinant. When inoculated into a non-immune host, the vaccine will provoke active immunity to the organism or material, but will not cause disease. Vaccines may take the form, for example, of a toxoid, which is defined as a toxin that has been detoxified but that still retains its major immunogenic determinants; or a killed organism, such as typhoid, cholera and poliomyelitis; or attenuated organisms, that are the live, but non-virulent, forms of pathogens, or it may be antigen encoded by such organism, or it may be a live tumor cell or an antigen present on a tumor cell. Vaccines may also take the form, for example, of nucleic acid which, when administered to a subject, specifies an antigenic determinant to which an immune response is desired.

In one embodiment, the invention provides for the use of an effective amount of an agent that directly binds to and activates IRE-1 (e.g., an HIV protease inhibitor) to increase XBP-1 activation in cells. In one embodiment, the agent increases the activation of immune cells or the production of proteins (e.g., cytokines or antibodies) by immune cells, e.g., B cells or macrophages. In one embodiment, the agent is administered in combination with an antigen. In yet another embodiment, such an agent is administered with a TLR agonist. In yet another embodiment, the agent is administered with an antigen and a TLR agonist. As a vaccine adjuvant, IRE-1 activating agents (with or without TLR agonists) improve the activation of the immune system (e.g., the innate immune system and/or the acquired immune system) and result, e.g., in enhanced activation of T and/or B cells as well as macrophages.

Natural Infection

In one embodiment, the invention provides for the use of an effective amount of an agent that directly binds to and activates IRE-1 (e.g., an HIV protease inhibitor) to increase the activation of immune cells, e.g., macrophages and/or B cells in the context of an infection. In one embodiment, such an agent is administered with a TLR agonist to a subject having an infection. As an agent for use in treating infection, IRE-1 activating agents (with or without TLR agonists) improve the activation of the immune cells and result, e.g., in enhanced clearance of and/or response to the infectious agent. Exemplary infectious agents include viruses (other than HIV), bacteria, and parasites.

Cancer

In one embodiment, the subject agents that bind to and activate IRE-1 can be used to improve the immune response to cancer cells. For example, in one embodiment, agents that activate IRE-1 can be administered to a subject to increase immune responses to cancer cells or molecules associated with cancer cells. Such agents may be administered with or without a TLR agonist or with or without a cancer antigen or with or without a cancer antigen and a TLR agonist.

Cancer antigens include antigens or antigenic determinant which is present on (or associated with) a tumor cell and not typically on normal cells, or an antigen or antigenic determinant which is present on or associated with tumor cells in greater amounts than on normal (non-tumor) cells, or an antigen or antigenic determinant which is present on tumor cells in a different form than that found on normal (non-tumor) cells. Such antigens include tumor-specific antigens, including tumor-specific membrane antigens, tumor-associated antigens, including tumor-associated membrane antigens, embryonic antigens on tumors, growth factor receptors, growth factor ligands, and any other type of antigen that is associated with cancer. A tumor antigen may be, for example, an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen. For example, the antigen may include a tumor antigen, such as βhCG, gp100 or Pmel17, CEA, gp100, TRP-2, NY-BR-1, NY-CO-58, MN (gp250), idiotype, Tyrosinase, Telomerase, SSX2, MUC-1, MAGE-A3, and high molecular weight-melanoma associated antigen (HMW-MAA) MART1, melan-A, NY-ESO-1, MAGE-1, MAGE-3, WT1, Her2, mesothelin or high molecular weight-melanoma associated antigen (HMW-MAA). In another embodiment, a tumor antigen may be a composition which comprises a number of such molecules, e.g., in unpurified form or may be administered in the form of tumor cells or extract thereof.

III. Pharmaceutical Compositions

In one embodiment, agents that directly bind to IRE-1 (e.g., with or without a TLR agonist or with our without an antigen) can be administered to a subject as a pharmaceutical composition. In another embodiment, such an agent can be formulated with an acceptable carrier to be compatable with mammalian cells for use in vitro. Pharmaceutically acceptable carriers and methods of administration to a subject are described herein.

A pharmaceutical composition is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid; buffers such as acetates, citrates or phosphates and compounds for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition will preferably be sterile and should be fluid to the extent that easy syringability exists. It will preferably be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal compounds, for example, parabens, chlorobutanol, phenol, ascorbic acid, thimerosal, and the like. In many cases, it will be preferable to include isotonic compounds, for example, sugars, polyalcohols such as manitol, sorbitol, sodium chloride in the composition. Prolonged absorption of the injectable compositions can be brought about by including in the composition an compound which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

In one embodiment, preparations comprising carriers that will protect the compound against rapid elimination from the body, such as a controlled release formulation, including implants and microencapsulated delivery systems are used. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from, e.g., Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

V. Methods of Identifying Agents

Screening Methods

In one embodiment, the invention provides methods (also referred to herein as "screening assays") for identifying agents that enhance the innate immune response. In one embodiment, such methods comprise, a) providing an immune cell comprising an IRE-1 and an XBP-1 polypeptide;

b) contacting the immune cell with each member of a library of compounds;

c) determining the ability of the compound to directly bind to IRE-1 and activate XBP-1 in the absence of activation of PERK or ATF6, d) the effect of the compound on at least one parameter of activation of the immune cell;

e) selecting a compound of interest that increases at least one parameter of activation of the immune cell to thereby identify the compound as useful in enhancing the innate immune response. In one embodiment, compounds are selected based on their ability to synergize with a TLR agonist in the activation of immune cells In one embodiment a cell that naturally expresses or, more preferably, a cell that has been engineered to express the IRE-1 protein by introducing into the cell an expression vector encoding the protein is used. Preferably, the cell is a mammalian cell, e.g., a human cell. In another embodiment, the cell is a cell of the innate immune system, e.g., a hematopoietic cell. In one embodiment, the cell is a macrophage or a dendritic cell. In one embodiment, the cell is under ER stress. In another embodiment, the cell is stimulated with a TLR agonist, e.g., lipopolysaccharide (LPS), lipoteichoic acid, PAM3CSK4, and FSL1.

Compounds identified in the assays described herein are useful in modulating IRE-1 activity, and thereby modulating XBP-1 activity, in cells comprising IRE-1 and XBP-1. XBP-1 has been shown to play a role in numerous cell types.

In one embodiment, compounds identified the assays described herein are useful for modulating activation in cells of the innate immune system.

The subject screening assays can be performed in the presence or absence of other agents. In one embodiment, the subject assays are performed in the presence of an agent that affects the unfolded protein response, e.g., tunicamycin, which evokes the UPR by inhibiting N-glycosylation, or thapsigargin, or HIV protease inhibitors. In another embodiment, the subject assays are performed in the presence of an agent that inhibits degradation of proteins by the ubiquitin-proteasome pathway (e.g., peptide aldehydes, such as MG132). In another embodiment, the screening assays can be performed in the presence or absence of a molecule that enhances cell activation.

A modulating agent can be identified using an assay, and the ability of the agent to modulate the activity of XBP-1 or a molecule in a signal transduction pathway involving XBP-1 can be confirmed in vivo, e.g., in an animal model for immune cell activation or inflammation.

In another embodiment, modulation of the UPR or ER stress can also be determined and used as an indicator of modulation of XBP-1 and/or IRE-1 activity. Transcription of genes encoding molecular chaperones and folding enzymes in the endoplasmic reticulum (ER) is induced by accumulation of unfolded proteins in the ER. This intracellular signaling, known as the unfolded protein response (UPR), is mediated by the cis-acting ER stress response element (ERSE) or unfolded protein response element (UPRE) in mammals.

The activation of the kinase PERK can also be measured to determine whether an agent moduleates ER stress by measuring the induction of CHOP. The processing of ATF6 alpha can also be measured to determine whether an agent modulates ER stress. The basic leucine zipper protein ATF6 alpha isolated as a CCACG-binding protein is synthesized as a transmembrane protein in the ER, and ER stress-induced proteolysis produces a soluble form of ATF6 alpha that translocates into the nucleus.

In one embodiment, compounds that modulate TLR-mediated signaling and do not activate ER stress and/or the UPR are identified. In another embodiment, compounds that modulate TLR-mediated signaling and do activate ER stress and/or the UPR are identified.

In one embodiment, the ability of a compound to modulate proinflammatory cytokine production, e.g., IL-6, IFNβ, ISG15, can be determined. Production of proinflammatory cytokine can be monitored, for example, using RT-PCR, Northern or Western blotting. Proinflammatory cytokine can also be detected using an ELISA assay or in a bioassay, e.g., employing cells which are responsive to proinflammatory cytokine (e.g., cells which proliferate in response to the cytokine or which survive in the presence of the cytokine), such as plasma cells or multiple myeloma cells using standard techniques.

In one embodiment, the effect of a test compound on sustained production of a proinflammatory cytokine may be determined. For example, the production of a proinflammatory cytokine may be determined at multiple time points, e.g., a time course assay, e.g., at about 0, 0.5, 1. 1.5, 2, 2.5, 3, 3.5, 4, 4.5, 5. 5.5, 6, 6.5, 7, 7.5, 8, 8.5, 9, 9.5, 10, 10.5, 11, 11.5, 12, 13, 14, 15, 16, 17, 18, 19, 20, 21, 22, 23, 24 hours, following exposure to a test compound.

The techniques for assessing the ratios of unspliced to spliced XBP-1 and spliced to unspliced XBP-1 are routine in the art. For example, the two forms can be distinguished based on their size, e.g., using northern blots or western blots. Because the spliced form of XBP-1 comprises an exon not found in the unspliced form, in another embodiment, antibodies that specifically recognize the spliced or unspliced form of XBP-1 can be developed using techniques well known in the art (Yoshida et al. 2001. Cell. 107:881). In addition, PCR can be used to distinguish spliced from unspliced XBP-1. For example, as described herein, primer sets can be used to amplify XBP-1 where the primers are derived from positions 410 and 580 of murine XBP-1, or corresponding positions in related XBP-1 molecules, in order to amplify the region that encompasses the splice junction. A fragment of 171 base pairs corresponds to unspliced XBP-1 mRNA. An additional band of 145 by corresponds to the spliced form of XBP-1. The ratio of the different forms of XBP-1 can be determined using these or other art recognized methods.

Compounds that alter the ratio of unspliced to spliced XBP-1 or spliced to unspliced XBP-1 can be useful to modulate TLR-mediated signaling and/or the activity of XBP-1, and the levels of these different forms of XBP-1 can be measured using various techniques described above, or known in the art, and a ratio determined.

The cells of the invention can express endogenous XBP-1 and/or IRE-1, or can be engineered to do so. For example, a cell that has been engineered to express the XBP-1 protein and/or a non XBP-1 protein can be produced by introducing into the cell an expression vector encoding the protein.

A variety of test compounds can be evaluated using the screening assays described herein. The term "test compound" includes any reagent or test agent which is employed in the assays of the invention and assayed for its ability to influence the expression and/or activity of XBP-1 and/or IRE-1. More than one compound, e.g., a plurality of compounds, can be tested at the same time for their ability to modulate the expression and/or activity of, e.g., XBP-1, in a screening assay. The term "screening assay" preferably refers to assays which test the ability of a plurality of compounds to influence the readout of choice rather than to tests which test the ability of one compound to influence a readout. Preferably, the subject assays identify compounds not previously known to have the effect that is being screened for. In one embodiment, high throughput screening can be used to assay for the activity of a compound.

In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin et al. (1992). *J. Am. Chem. Soc.* 114:10987; DeWitt et al. (1993). *Proc. Natl. Acad. Sci. USA* 90:6909) peptoids (Zuckermann. (1994). *J. Med. Chem.* 37:2678) oligocarbamates (Cho et al. (1993). *Science.* 261:1303), and hydantoins (DeWitt et al. supra). An approach for the synthesis of molecular libraries of small organic molecules with a diversity of 104-105 as been described (Carell et al. (1994). *Angew. Chem. Int. Ed. Engl.* 33:2059-; Carell et al. (1994) Angew. *Chem. Int. Ed. Engl.* 33:2061-).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145). Other exemplary methods for the synthesis of molecular libraries can be found in the art, for example in: Erb et al. (1994). *Proc. Natl. Acad. Sci. USA* 91:11422; Horwell et al. (1996) *Immunopharmacology* 33:68-; and in Gallop et al. (1994); *J. Med. Chem.* 37:1233-.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310). In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

Candidate/test compounds include, for example, 1) peptides such as soluble peptides, including Ig-tailed fusion peptides and members of random peptide libraries (see, e.g., Lam, K. S. et al. (1991) *Nature* 354:82-84; Houghten, R. et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthatases, isomerases, polymerases, kinases, phosphatases, oxido-reductases and ATPases), and 6) mutant forms of XBP-1 (or e.g., IRE-1 molecules, e.g., dominant negative mutant forms of the molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222: 301-310; Ladner supra.).

Compounds identified in the subject screening assays can be used in methods of modulating one or more of the biological responses regulated by XBP-1. It will be understood that it may be desirable to formulate such compound(s) as pharmaceutical compositions (described supra) prior to contacting them with cells.

Once a test compound is identified that directly or indirectly modulates, e.g., XBP-1 expression or activity, by one of the variety of methods described hereinbefore, the selected test compound (or "compound of interest") can then be further evaluated for its effect on cells, for example by contacting the compound of interest with cells either in vivo (e.g., by administering the compound of interest to a subject) or ex vivo (e.g., by isolating cells from the subject and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate the biological response).

Computer Based Design of IRE-1 Inhibitors/HIV Protease Inhibitors

Computer-based analysis of IRE-1 can also be used to identify molecules which bind to the protein or to identify variants of HIV protease inhibitors with improved binding, e.g., with improved binding to IRE-1 and reduced binding to HIV protease or with improved binding to HIV protease and reduced binding to IRE-1.

Molecular modeling may use computers to model the molecular structure of IRE-1 and/or HIV protease and/or HIV protease inhibitors. Non-limiting examples of such methods include molecular graphics (i.e., 3-D representations) to computational chemistry (i.e., calculations of the physical and chemical properties). Using molecular modeling, rational drug design programs can look at a range of molecular structures that may fit into an active site of the enzyme or interact at the interface between the IRE-1 subunits. By using computer programs, for example, a determination can be made as to which compounds actually fit into or bind a given site. U.S. patents that provide additional information on molecular modeling include U.S. Pat. Nos. 6,093,573; 6,080,576; 5,612,894; 5,583,973; 5,030,103; 4,906,122; and 4,812,128, each of which is incorporated herein by reference in its entirety. As used in the methods described herein, the term "computer fitting analysis" or "modeling" refers to a schematic or other work that is prepared using a computer algorithms or computer programs that can process and provide information about protein structure and conformation. A number of such programs and algorithms are readily available and known to those of skill in the art. They can configure a protein sequence into a 3-dimensional molecule and additionally configure it with a ligand or other substrate.

For example, using a 3-D database, a program such as DOCK can be used to identify molecules which will bind to XBP-1 or a molecule in a signal transduction pathway involving XBP-1. See DesJarlias et al. (1988) J. Med. Chem. 31:722; Meng et al. (1992) J. Computer Chem. 13:505; Meng et al. (1993) Proteins 17:266; Shoichet et al. (1993) Science 259:1445. In addition, the electronic complementarity of a molecule to a targeted protein can also be analyzed to identify molecules which bind to the target. This can be determined using, for example, a molecular mechanics force field as described in Meng et al. (1992) J. Computer Chem. 13:505 and Meng et al. (1993) Proteins 17:266. Other programs which can be used include CLIX which uses a GRID force field in docking of putative ligands. See Lawrence et al. (1992) Proteins 12:31; Goodford et al. (1985) J. Med. Chem. 28:849; Boobbyer et al. (1989) J. Med. Chem. 32:1083

This invention is further illustrated by the following examples which should not be construed as limiting. The contents of all references, patents and published patent applications cited throughout this application are hereby incorporated by reference.

EXAMPLES

Example 1

HIV-protease inhibitors (PIs) trigger robust IRE1 and XBP1 activation and synergize with TLR4 activation to produce cytokines and co-stimulatory molecules.

XBP1 mRNA maturation (XBP1s) in J774 cells stimulated with dose dependent concentrations of HIV-PIs (similar data were obtained in primary mouse M0s, and various M0 cell lines of human and mouse origin) see FIG. 1, panel A. Cell extracts of cells stimulated with Tunicamycin (TM) or HIV-protease inhibitors were monitored for IRE1 activation by phosphorylation in a Phos-tag SDS-PAGE gel, CHOP induction and ATF6a processing, see FIG. 1, panel B. Realtime PCR of CHOP induction by the ER-stress inducer TM and the HIV-PI Nelfinavir (NFR) was analyzed in PERK proficient and deficient MEFs see FIG. 1, panel C. J774 cells were stimulated with HIV-PIs or TM as indicated in presence or absence of LPS and analyzed for IL-6 production by rtPCR, see FIG. 1, panel D. Increased IL-6 production and co-stimulatory ligand (CD86 and CD40) expression were observed in the presence of Nelfinavir and the synthetic TLR4 agonist MPLA compared to TLR4 agonist alone, see FIG. 1, panel E.

Example 2

In vitro fluorescent splicing reporter assay with recombinant IRE1 protein reveals marked induction of xbp1 splicing with ritonivir and nelfinivir but not amprenivir at doses of PIs ranging from 20 uM to 0.63 uM, see FIG. 2. As shown in FIG. 3, these PIs also induce XBP-1 splicing in mouse embryonic fibroblasts.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

What is claimed is:

1. A method for increasing activation of immune cells in a subject, comprising administering at least one toll-like receptor (TLR) agonist and a human immunodeficiency virus (HIV) protease inhibitor that activates IRE-1 in the subject thereby increasing activation of immune cells in the subject, wherein the toll-like receptor (TLR) agonist stimulates TLR4; and contacting the immune cells with an antigen to which an immune response is desired.

2. The method of claim 1, wherein the subject has cancer.

3. The method of claim 1, wherein production of a proinflammatory cytokine by the immune cells is increased.

4. The method of claim 3, wherein the proinflammatory cytokine is interleukin-6 (IL-6).

5. The method of claim 1, wherein the expression of at least one costimulatory molecule is increased.

6. The method of claim 5, wherein the expression of cluster of differentiation 40 (CD40) is increased.

7. The method of claim 1, wherein the immune cells comprise macrophages.

8. The method of claim 1, wherein the HIV protease inhibitor is selected from the group consisting of: Atazanavir, Lopinavir, Nelfinavir and Ritonavir.

9. The method of claim 8, wherein the HIV protease inhibitor is Nelfinavir.

10. The method of claim 1, wherein the activation of immune cells is increased in vivo.

* * * * *

UNITED STATES PATENT AND TRADEMARK OFFICE
CERTIFICATE OF CORRECTION

| | | |
|---|---|---|
| PATENT NO. | : 9,956,236 B2 | Page 1 of 5 |
| APPLICATION NO. | : 13/983180 | |
| DATED | : May 1, 2018 | |
| INVENTOR(S) | : Glimcher et al. | |

It is certified that error appears in the above--identified patent and that said Letters Patent is hereby corrected as shown below:

On the Title Page

In Column 2, item (56), under "Other Publications", Line 2, delete "IRE1 α" and insert --IRE1α-- therefor On page 3, in Column 2, item (56), under "Other Publications", Line 10, delete "Fonnation" and insert --Formation-- therefor On page 3, in Column 2, item (56), under "Other Publications", Line 12, delete "60. And 6p" and insert --6α and 6β-- therefor On page 3, in Column 2, item (56), under "Other Publications", Line 71, delete ""CoCl2," and insert --"$CoCl_2$,-- therefor On page 4, in Column 1, item (56), under "Other Publications", Line 44, delete "REgulator" and insert --Regulator-- therefor On page 4, in Column 2, item (56), under "Other Publications", Line 43, delete "Phosphplipid-Linked" and insert --Phospholipid-Linked-- therefor On page 4, in Column 2, item (56), under "Other Publications", Line 58, delete "a-Subunit" and insert --α-Subunit-- therefor On page 4, in Column 2, item (56), under "Other Publications", Line 62, delete "Irelp" and insert --IRE1p-- therefor On page 4, in Column 2, item (56), under "Other Publications", Line 65, delete ""RNA" and insert --"tRNA-- therefor Signed and Sealed this
Twenty-eighth Day of April, 2020

Andrei Iancu
*Director of the United States Patent and Trademark Office*

On page 5, in Column 1, item (56), under "Other Publications", Lines 28-29, delete "OfInhibitors OfThymidylate" and insert --of Inhibitors of Thymidylate-- therefor On page 5, in Column 1, item (56), under "Other Publications", Line 60, delete "IREI" and insert --IRE1-- therefor On page 5, in Column 2, item (56), under "Other Publications", Line 5, delete ""IREI" and insert --"IRE1-- therefor On page 5, in Column 2, item (56), under "Other Publications", Line 38, delete "21 ras" and insert --p21$^{ras}$-- therefor On page 6, in Column 2, item (56), under "Other Publications", Line 38, delete "Biocactive" and insert --Bioactive-- therefor On page 7, in Column 1, item (56), under "Other Publications", Line 17, delete "Drig" and insert --Drug-- therefor On page 7, in Column 2, item (56), under "Other Publications", Line 19, delete ".alpha.-Fetoprotein,"" and insert --α-Fetoprotein,"-- therefor On page 7, in Column 2, item (56), under "Other Publications", Line 56, delete "Mismathces" and insert --Mismatches-- therefor On page 8, in Column 2, item (56), under "Other Publications", Line 28, delete "Intra-nd" and insert --Intra-and-- therefor On page 9, in Column 1, item (56), under "Other Publications", Line 14, delete "(991)." and insert --(1991).-- therefor On page 9, in Column 1, item (56), under "Other Publications", Line 62, delete "CompoundsFrom" and insert --Compounds From-- therefor On page 9, in Column 2, item (56), under "Other Publications", Line 60, delete "HI V-I" and insert --HIV-1-- therefor On page 9, in Column 2, item (56), under "Other Publications", Line 61, delete "HIV-I" and insert --HIV-1-- therefor On page 9, in Column 2, item (56), under "Other Publications", Line 64, delete "CellsIn" and insert --Cells In-- therefor On page 9, in Column 2, item (56), under "Other Publications", Line 68, delete ""Tranjent" and insert --"Transient-- therefor

CERTIFICATE OF CORRECTION (continued)
U.S. Pat. No. 9,956,236 B2

On page 10, in Column 2, item (56), under "Other Publications", Line 5, delete "Ire1 alpha" and insert --IRE1alpha-- therefor On page 11, in Column 2, item (56), under "Other Publications", Line 15, delete "Matruation"" and insert --Maturation"-- therefor On page 11, in Column 2, item (56), under "Other Publications", Line 33, delete "Ire 1p" and insert --IRE1p-- therefor On page 12, in Column 1, item (56), under "Other Publications", Line 34, delete "Ofp53" and insert --Of p53-- therefor On page 12, in Column 2, item (56), under "Other Publications", Line 54, delete "elF2a" and insert --elF2α-- therefor On page 12, in Column 2, item (56), under "Other Publications", Line 55, delete "P58IPK."" and insert --P58$^{IPK}$."-- therefor On page 13, in Column 1, item (56), under "Other Publications", Line 4, delete "IREI" and insert --IRE1-- therefor On page 13, in Column 2, item (56), under "Other Publications", Line 1, delete "elF-2a" and insert --elF-2α-- therefor On page 13, in Column 2, item (56), under "Other Publications", Line 8, delete "Cy" and insert --by-- therefor On page 13, in Column 2, item (56), under "Other Publications", Line 33, delete "Dnaj" and insert --DnaJ-- therefor On page 14, in Column 1, item (56), under "Other Publications", Line 18, delete ""P58IPK," and insert --"P58$^{IPK}$,-- therefor On page 14, in Column 2, item (56), under "Other Publications", Line 5, delete "IRE1" and insert --IRE1α-- therefor On page 14, in Column 2, item (56), under "Other Publications", Line 8, delete "IRE1 alpha,"" and insert --IRE1alpha,"-- therefor On page 14, in Column 2, item (56), under "Other Publications", Line 17, delete ".beta.1" and insert --β1-- therefor On page 14, in Column 2, item (56), under "Other Publications", Line 22, delete "a-mannosidase-like" and insert --α-mannosidase-like-- therefor

CERTIFICATE OF CORRECTION (continued)
U.S. Pat. No. 9,956,236 B2

On page 14, in Column 2, item (56), under "Other Publications", Line 50, delete "IRE1 alpha" and insert --IRE1alpha-- therefor On page 15, in Column 1, item (56), under "Other Publications", Line 12, delete "Factor.beta.," and insert --Factor β,-- therefor On page 15, in Column 1, item (56), under "Other Publications", Line 21, delete "accumuilation" and insert --accumulation-- therefor On page 15, in Column 1, item (56), under "Other Publications", Line 69, delete "interferoninduced" and insert --interferon-induced-- therefor On page 15, in Column 1, item (56), under "Other Publications", Line 69, delete "M," and insert --$M_r$-- therefor On page 16, in Column 2, item (56), under "Other Publications", Line 16, delete "1" and insert --1α-- therefor On page 16, in Column 2, item (56), under "Other Publications", Line 37, delete "NF-kappa.B"" and insert --NF-kappaB."-- therefor On page 16, in Column 2, item (56), under "Other Publications", Line 58, delete ".alpha.-Fetoprotein"" and insert --α-Fetoprotein"-- therefor On page 16, in Column 2, item (56), under "Other Publications", Line 68, delete "Dna" and insert --DnaJ-- therefor On page 17, in Column 1, item (56), under "Other Publications", Line 25, delete ".beta.1" and insert --β1-- therefor On page 18, in Column 1, item (56), under "Other Publications", Line 57, delete "IL-I 0" and insert --IL-10-- therefor On page 18, in Column 1, item (56), under "Other Publications", Line 63, delete ""IL-I 0" and insert --"IL-10-- therefor On page 18, in Column 2, item (56), under "Other Publications", Line 15, delete "2-a" and insert --2-α-- therefor On page 18, in Column 2, item (56), under "Other Publications", Line 15, delete "Wolcotl-Rallison" and insert --Wolcott-Rallison-- therefor On page 19, in Column 1, item (56), under "Other Publications", Line 12, delete "Helix-Fonning" and insert --Helix-Forming-- therefor

CERTIFICATE OF CORRECTION (continued)
U.S. Pat. No. 9,956,236 B2

In the Claims

In Column 26, Line 15, in Claim 1, after "and", insert --¶--